(12) United States Patent
Carson et al.

(10) Patent No.: US 7,956,068 B2
(45) Date of Patent: Jun. 7, 2011

(54) INHIBITORS OF HUMAN IMMUNODEFICIENCY VIRUS REPLICATION

(75) Inventors: Rebekah J. Carson, Mascouche (CA); Lee Fader, St-Lazare (CA); Stephen Kawai, Montreal (CA); Serge R. Landry, St-Jerome (CA); Youla S. Tsantrizos, Montreal (CA); Christian Brochu, Blainville (CA); Sebastien Morin, Montreal (CA); Mathieu Parisien, Montreal (CA); Bruno Simoneau, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/743,143

(22) PCT Filed: Nov. 3, 2008

(86) PCT No.: PCT/CA2008/001935
§ 371 (c)(1), (2), (4) Date: Aug. 2, 2010

(87) PCT Pub. No.: WO2009/062288
PCT Pub. Date: May 22, 2009

(65) Prior Publication Data
US 2010/0305115 A1    Dec. 2, 2010

Related U.S. Application Data

(60) Provisional application No. 60/988,342, filed on Nov. 15, 2007.

(51) Int. Cl.
*C07D 495/04* (2006.01)
*A61K 31/4365* (2006.01)

(52) U.S. Cl. .................................. 514/301; 546/114
(58) Field of Classification Search ................ 546/114; 514/301
See application file for complete search history.

(56) References Cited

FOREIGN PATENT DOCUMENTS

| CA | 2600832 A1 | 10/2006 |
|----|------------|---------|
| CA | 2606282 A1 | 11/2006 |
| CA | 2622639 A1 | 4/2007 |
| CA | 2626956 A1 | 5/2007 |

OTHER PUBLICATIONS

International Search Report, Form PCT/ISA/210, for corresponding PCT/CA2008/001935; date of mailing: Jan. 26, 2009.

*Primary Examiner* — Kahsay T Habte
(74) *Attorney, Agent, or Firm* — Michael P. Morris; Alan R. Stempel

(57) ABSTRACT

The present invention relates to compounds of formula (I)

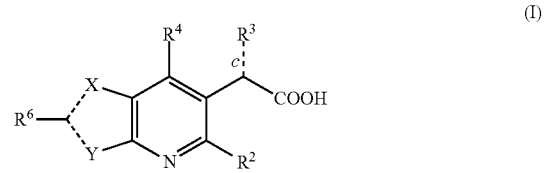

wherein c, X, Y, $R^2$, $R^3$, $R^4$ and $R^6$ are as defined herein, compositions and uses thereof for treating human immunodeficiency virus (HIV) infection. In particular, the present invention provides novel inhibitors of HIV integrase, pharmaceutical compositions containing such compounds and methods for using these compounds in the treatment of HIV infection.

13 Claims, No Drawings

US 7,956,068 B2

INHIBITORS OF HUMAN IMMUNODEFICIENCY VIRUS REPLICATION

RELATED APPLICATIONS

This application claims benefit of U.S. Ser. No. 60/988,342, filed Nov. 15, 2007, which is herein incorporated by reference.

FIELD OF THE INVENTION

The present invention relates to compounds, compositions and methods for the treatment of human immunodeficiency virus (HIV) infection. In particular, the present invention provides novel inhibitors of HIV replication, pharmaceutical compositions containing such compounds and methods for using these compounds in the treatment of HIV infection. More specifically, the present invention provides novel inhibitors of the HIV integrase enzyme, pharmaceutical compositions containing such compounds and methods for using these compounds to reduce HIV replication and in the treatment of HIV infection.

BACKGROUND OF THE INVENTION

Acquired immune deficiency syndrome (AIDS) is caused by the human immunodeficiency virus (HIV), particularly the HIV-1 strain. Most currently approved therapies for HIV infection target the viral reverse transcriptase and protease enzymes. There is additionally one approved drug targeting gp41 to inhibit viral entry and one approved drug targeting the integrase enzyme. Within the reverse transcriptase inhibitor and protease inhibitor classes, resistance of HIV to existing drugs is a problem. Therefore, it is important to discover and develop new antiretroviral compounds.

SUMMARY OF THE INVENTION

The present invention provides a novel series of compounds having inhibitory activity against HIV replication. Furthermore, representative compounds of the invention have activity as inhibitors in a cell-based HIV replication assay. The compounds of the present invention have an affinity for the HIV integrase enzyme. Therefore, the compounds of the invention may be used to inhibit the activity of HIV integrase and may be used to reduce HIV replication. Further objects of this invention arise for the one skilled in the art from the following description and the examples.

One aspect of the invention provides an isomer, racemate, enantiomer or diastereomer of a compound of formula (I):

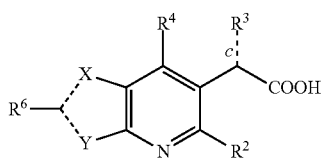

(I)

wherein
------ represents either a single or double bond;
X is S or $CR^5$;
Y is S or $CR^7$;
wherein one of X or Y is S;
$R^2$, $R^5$, $R^6$ and $R^7$ are each independently selected from:
a) halo;
b) $R^8$, $-C(=O)-R^8$, $-C(=O)-O-R^8$, $-O-R^8$, $-S-R^8$, $SO-R^8$, $-SO_2-R^8$, $-(C_{1-6})$alkylene-$R^8$, $-(C_{1-6})$alkylene-$C(=O)-R^8$, $-(C_{1-6})$alkylene-$C(=O)-O-R^8$, $-(C_{1-6})$alkylene-$SO-R^8$ or $-(C_{1-6})$alkylene-$SO_2-R^8$, $-(C_{1-6})$alkylene-$O-R^8$ or $-(C_{1-6})$alkylene-$S-R^8$;
wherein $R^8$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het;
and
wherein each of the aryl and Het is optionally substituted with 1 to 3 substituents each independently selected from:
i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, $-OH$, $-O(C_{1-6})$alkyl, $-O$ $(C_{1-6})$haloalkyl, $-SH$, $-S(C_{1-6})$alkyl, $-SO(C_{1-6})$alkyl, $-SO_2(C_{1-6})$alkyl, $-NH_2$, $-NH(C_{1-6})$alkyl and $-N((C_{1-6})$alkyl$)_2$;
ii) $(C_{1-6})$alkyl optionally substituted with $-OH$, $-O-(C_{1-6})$haloalkyl, or $-O-(C_{1-6})$alkyl; and
iii) aryl or Het, wherein each of the aryl and Het is optionally substituted with halo or $(C_{1-6})$alkyl; and
c) $-N(R^9)R^{10}$, $-C(=O)-N(R^9)R^{10}$, $-O-C(=O)-N(R^9)R^{10}$, $-SO_2-N(R^9)R^{10}$, $-(C_{1-6})$alkylene-$N(R^9)R^{10}$, $-(C_{1-6})$alkylene-$C(=O)-N(R^9)R^{10}$, $-(C_{1-6})$alkylene-$O-C(=O)-N(R^9)R^{10}$, or $-(C_{1-6})$alkylene-$SO_2-N(R^9)R^{10}$
wherein
$R^9$ is in each instance independently selected from H, $(C_{1-6})$alkyl and $(C_{3-7})$cycloalkyl; and
$R^{10}$ is in each instance independently selected from $R^8$, $-(C_{1-6})$alkylene-$R^8$, $-SO_2-R^8$, $-C(=O)-R^8$, $-C(=O)OR^8$ and $-C(=O)N(R^9)R^8$; wherein $R^8$ and $R^9$ are as defined above;
$R^3$ is $(C_{1-6})$alkyl, $(C_{1-6})$haloalkyl, $(C_{2-6})$alkenyl, $(C_{2-6})$alkynyl, $(C_{3-7})$cycloalkyl-$(C_{1-6})$alkyl-, aryl-$(C_{1-6})$alkyl, -Het-$(C_{1-6})$alkyl- or $-W-R^{31}$, and bond c is a single bond; or
$R^3$ is $(C_{1-6})$alkylidene and bond c is a double bond;
wherein W is O or S and $R^{31}$ is $(C_{1-6})$alkyl, $(C_{1-6})$haloalkyl, $(C_{2-6})$alkenyl, $(C_{2-6})$alkynyl, $(C_{3-7})$cycloalkyl, aryl, $(C_{3-7})$cycloalkyl-$(C_{1-6})$alkyl-, aryl-$(C_{1-6})$alkyl- or Het-$(C_{1-6})$alkyl-;
wherein each of the $(C_{1-6})$alkylidene, $(C_{1-6})$alkyl, $(C_{1-6})$haloalkyl, $(C_{2-6})$alkenyl, $(C_{2-6})$alkynyl, $(C_{3-7})$cycloalkyl-$(C_{1-6})$alkyl-, aryl-$(C_{1-6})$alkyl-, Het-$(C_{1-6})$alkyl- and $-W-R^{31}$ is optionally substituted with 1 to 3 substituents each independently selected from $(C_{1-6})$alkyl, halo, cyano, oxo and $-O(C_{1-6})$alkyl;
$R^4$ is aryl or Het, wherein each of the aryl and Het is optionally substituted with 1 to 5 substituents each independently selected from halo, $(C_{1-6})$alkyl, $(C_{2-6})$alkenyl, $(C_{1-6})$haloalkyl, $(C_{3-7})$cycloalkyl, $(C_{3-7})$cycloalkyl-$(C_{1-6})$alkyl-, $-OH$, $-O(C_{1-6})$alkyl, $-SH$, $-S(C_{1-6})$alkyl, $-NH_2$, $-NH(C_{1-6})$alkyl and $-N((C_{1-6})$alkyl$)_2$; wherein the $(C_{1-6})$alkyl is optionally substituted with hydroxy, $-O(C_{1-6})$alkyl, cyano or oxo;
and
wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$;
or a salt or an ester thereof.

Another aspect of this invention provides a compound of formula (I) or a pharmaceutically acceptable salt or ester thereof, as a medicament.

Still another aspect of this invention provides a pharmaceutical composition comprising a therapeutically effective amount of a compound of formula (I) or a pharmaceutically acceptable salt or ester thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of an HIV infection in a mammal having or at risk of having the infection.

A further aspect of the invention involves a method of treating an HIV infection in a mammal having or at risk of having the infection, the method comprising administering to the mammal a therapeutically effective amount of a compound of formula (I), a pharmaceutically acceptable salt or ester thereof, or a composition thereof as described hereinabove.

Another aspect of the invention involves a method of treating an HIV infection in a mammal having or at risk of having the infection, the method comprising administering to the mammal a therapeutically effective amount of a combination of a compound of formula (I) or a pharmaceutically acceptable salt or ester thereof, and at least one other antiviral agent; or a composition thereof.

Also within the scope of this invention is the use of a compound of formula (I) as described herein, or a pharmaceutically acceptable salt or ester thereof, for the treatment of an HIV infection in a mammal having or at risk of having the infection.

Another aspect of this invention provides the use of a compound of formula (I) as described herein, or a pharmaceutically acceptable salt or ester thereof, for the manufacture of a medicament for the treatment of an HIV infection in a mammal having or at risk of having the infection.

An additional aspect of this invention refers to an article of manufacture comprising a composition effective to treat an HIV infection; and packaging material comprising a label which indicates that the composition can be used to treat infection by HIV; wherein the composition comprises a compound of formula (I) according to this invention or a pharmaceutically acceptable salt or ester thereof.

Still another aspect of this invention relates to a method of inhibiting the replication of HIV comprising exposing the virus to an effective amount of the compound of formula (I), or a salt or ester thereof, under conditions where replication of HIV is inhibited.

Further included in the scope of the invention is the use of a compound of formula (I) to inhibit the activity of the HIV integrase enzyme.

Further included in the scope of the invention is the use of a compound of formula (I), or a salt or ester thereof, to inhibit the replication of HIV.

DETAILED DESCRIPTION OF THE INVENTION

Definitions

As used herein, the following definitions apply unless otherwise noted:

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "$(C_{1-n})$alkyl" as used herein, wherein n is an integer, either alone or in combination with another radical, is intended to mean acyclic, straight or branched chain alkyl radicals containing from 1 to n carbon atoms. "$(C_{1-6})$alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "$(C_{1-n})$alkylene" as used herein, wherein n is an integer, either alone or in combination with another radical, is intended to mean acyclic, straight or branched chain divalent alkyl radicals containing from 1 to n carbon atoms. "$(C_{1-6})$alkylene" includes, but is not limited to, $—CH_2—$, $—CH_2CH_2—$,

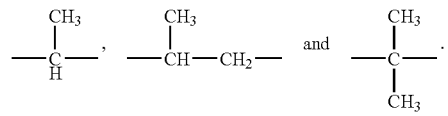

The term "$(C_{1-n})$alkylidene" as used herein, wherein n is an integer, either alone or in combination with another radical, is intended to mean acyclic, straight or branched chain alkyl radicals containing from 1 to n carbon atoms which are bonded to a molecule or fragment thereof, as a substituent thereof, by a double bond. "$(C_{1-6})$alkylidene" includes, but is not limited to, $CH_2=$, $CH_3CH=$, $CH_3CH_2CH=$,

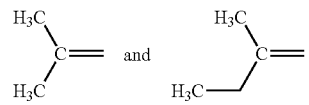

groups. Unless specified otherwise, the term "$(C_{2-n})$alkylidene" is understood to encompass individual stereoisomers where possible, including but not limited to (E) and (Z) isomers, and mixtures thereof. When a $(C_{2-n})$alkylidene group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{3-m})$cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl.

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of $(C_{3-7})$cycloalkyl-$(C_{1-6})$alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise, such that the substitution would give rise to a chemically stable compound, such as are recognized by those skilled in the art.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-n})$alkyl- include, but are not limited to, phenylmethyl (benzyl), 1-phenylethyl, 2-phenylethyl and phenylpropyl. When an aryl-$(C_{1-n})$alkyl- group is substituted, it is understood that substituents may be attached to either the aryl or the alkyl portion thereof or both, unless specified otherwise, such that the substitution would give rise to a chemically stable compound, such as are recognized by those skilled in the art.

The term "carbocycle" as used herein, either alone or in combination with another radical, is intended to mean a cyclic compound, either aromatic or non-aromatic, saturated or unsaturated, in which all of the ring members are carbon atoms. The carbocycle group may be containing 5 or 6 carbon atom and may be further fused to a second 5- or 6-membered carbocyclic group which may be aromatic, saturated or unsaturated. The carbocycle may be substituted. When the carbocycle is substituted, it is understood that substituents may be attached to any carbon atom which would otherwise bear a hydrogen atom, unless specified otherwise, such that the substitution would give rise to a chemically stable compound, such as are recognized by those skilled in the art.

The term "Het" as used herein, either alone or in combination with another radical, is intended to mean a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S, wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$, unless specified otherwise. When a Het group is substituted, it is understood that substituents may be attached to any carbon atom or heteroatom thereof which would otherwise bear a hydrogen atom, unless specified otherwise, such that the substitution would give rise to a chemically stable compound, such as are recognized by those skilled in the art.

The term "Het-$(C_{1-n})$alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-$(C_{1-n})$alkyl- include, but are not limited to, thienylmethyl, furylmethyl, piperidinylethyl, 2-pyridinylmethyl, 3-pyridinylmethyl, 4-pyridinylmethyl, quinolinylpropyl, and the like. When an Het-$(C_{1-n})$alkyl- group is substituted, it is understood that substituents may be attached to either the Het or the alkyl portion thereof or both, unless specified otherwise, such that the substitution would give rise to a chemically stable compound, such as are recognized by those skilled in the art.

The term "heteroatom" as used herein is intended to mean O, S or N.

The term "heterocycle" as used herein and unless specified otherwise, either alone or in combination with another radical, is intended to mean a 3- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine and pyrimidine, and saturated, unsaturated and aromatic derivatives thereof.

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, isoindole, benzimidazole, benzothiophene, benzofuran, benzopyran, benzodioxole, benzodioxane, benzothiazole, quinoline, isoquinoline, and naphthyridine, and saturated, unsaturated and aromatic derivatives thereof.

The term "halo" as used herein is intended to mean a halogen substituent selected from fluoro, chloro, bromo or iodo.

The term "$(C_{1-n})$haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of $(C_{1-n})$haloalkyl include but are not limited to chloromethyl, chloroethyl, dichloroethyl, bromomethyl, bromoethyl, dibromoethyl, fluoromethyl, difluoromethyl, trifluoromethyl, fluoroethyl and difluoroethyl.

The terms "—O—$(C_{1-n})$alkyl" or "$(C_{1-n})$alkoxy" as used herein interchangeably, wherein n is an integer, either alone or in combination with another radical, is intended to mean an oxygen atom further bonded to an alkyl radical having 1 to n carbon atoms as defined above. Examples of —O—$(C_{1-n})$alkyl include but are not limited to methoxy ($CH_3O$—), ethoxy ($CH_3CH_2O$—), propoxy ($CH_3CH_2CH_2O$—), 1-methylethoxy (iso-propoxy; $(CH_3)_2CH$—O—) and 1,1-dimethylethoxy (tert-butoxy; $(CH_3)_3C$—O—). When an —O—$(C_{1-n})$alkyl radical is substituted, it is understood to be substituted on the $(C_{1-n})$alkyl portion thereof, such that the substitution would give rise to a chemically stable compound, such as are recognized by those skilled in the art.

The term "—O—$(C_{1-n})$haloalkyl", wherein n is an integer, either alone or in combination with another radical, is intended to mean an oxygen atom further bonded to a haloalkyl radical having 1 to n carbon atoms as defined above. When an —O—$(C_{1-n})$haloalkyl radical is substituted, it is understood to be substituted on the $(C_{1-n})$alkyl portion thereof.

The terms "—S—$(C_{1-n})$alkyl" or "$(C_{1-n})$alkylthio" as used herein interchangeably, wherein n is an integer, either alone or in combination with another radical, is intended to mean an sulfur atom further bonded to an alkyl radical having 1 to n carbon atoms as defined above. Examples of —S—$(C_{1-n})$alkyl include but are not limited to methylthio ($CH_3S$—), ethylthio ($CH_3CH_2S$—), propylthio ($CH_3CH_2CH_2S$—), 1-methylethylthio (isopropylthio; $(CH_3)_2CH$—S—) and 1,1-dimethylethylthio (tert-butylthio; $(CH_3)_3C$—S—). When —S—$(C_{1-n})$alkyl radical, or an oxidized derivative thereof, such as an —SO—$(C_{1-n})$alkyl radical or an —$SO_2$—$(C_{1-n})$alkyl radical, is substituted, each is understood to be substituted on the $(C_{1-n})$alkyl portion thereof, such that the substitution would give rise to a chemically stable compound, such as are recognized by those skilled in the art.

The term "oxo" as used herein is intended to mean an oxygen atom attached to a carbon atom as a substituent by a double bond (=O).

The term "thioxo" as used herein is intended to mean a sulfur atom attached to a carbon atom as a substituent by a double bond (=S).

The term "cyano" as used herein is intended to mean a carbon atom attached to a nitrogen atom as a substituent by a triple bond.

The term "COOH" as used herein is intended to mean a carboxyl group (—C(=O)—OH). It is well known to one skilled in the art that carboxyl groups may be substituted by functional group equivalents. Examples of such functional group equivalents contemplated in this invention include, but are not limited to, esters, amides, imides, boronic acids, phosphonic acids, phosphoric acids, tetrazoles, triazoles, N-acylsulfamides ($RCONHSO_2NR_2$), and N-acylsulfonamides ($RCONHSO_2R$).

The term "functional group equivalent" as used herein is intended to mean an atom or group that may replace another atom or group which has similar electronic, hybridization or bonding properties.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof, herein incorporated by reference.

The following designation ⌐ is used in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Berge et al., J. Pharm. Sci., 1977, 66, pp. 1-19, herein incorporated by reference.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "ester thereof" as used herein is intended to mean any ester of a compound according to the invention in which any of the —COOH substituents of the molecule is replaced by a —COOR substituent, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl, each of which being optionally further substituted. The term "ester thereof" includes but is not limited to pharmaceutically acceptable esters thereof.

The term "pharmaceutically acceptable ester" as used herein is intended to mean esters of the compound according to the invention in which any of the COOH substituents of the molecule are replaced by a —COOR substituent, in which the R moiety of the ester is selected from alkyl (including, but not limited to, methyl, ethyl, propyl, 1-methylethyl, 1,1-dimethylethyl, butyl); alkoxyalkyl (including, but not limited to methoxymethyl); acyloxyalkyl (including, but not limited to acetoxymethyl); arylalkyl (including, but not limited to, benzyl); aryloxyalkyl (including, but not limited to, phenoxymethyl); and aryl (including, but not limited to phenyl) optionally substituted with halogen, $(C_{1-4})$alkyl or $(C_{1-4})$alkoxy. Other suitable esters can be found in Design of Prodrugs, Bundgaard, H. Ed. Elsevier (1985), herein incorporated by reference. Such pharmaceutically acceptable esters are usually hydrolyzed in vivo when injected into a mammal and transformed into the acid form of the compound according to the invention. With regard to the esters described above, unless otherwise specified, any alkyl moiety present preferably contains 1 to 16 carbon atoms, more preferably 1 to 6 carbon atoms. Any aryl moiety present in such esters preferably comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "mammal" as used herein is intended to encompass humans, as well as non-human mammals which are susceptible to infection by HIV. Non-human mammals include but are not limited to domestic animals, such as cows, pigs, horses, dogs, cats, rabbits, rats and mice, and non-domestic animals.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

The term "antiviral agent" as used herein is intended to mean an agent that is effective to inhibit the formation and/or replication of a virus in a mammal, including but not limited to agents that interfere with either host or viral mechanisms necessary for the formation and/or replication of a virus in a mammal.

The term "inhibitor of HIV replication" as used herein is intended to mean an agent capable of reducing or eliminating the ability of HIV to replicate in a host cell, whether in vitro, ex vivo or in vivo.

The term "HIV integrase" or "integrase", used herein interchangeably, means the integrase enzyme encoded by the human immunodeficiency virus type 1.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Preferred Embodiments

In the following preferred embodiments, groups and substituents of the compounds of formula (I):

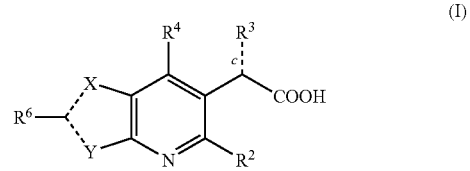

(I)

according to this invention are described in detail.

Core:

Core-A: In this embodiment, the compounds of the invention are represented by formula (Ia):

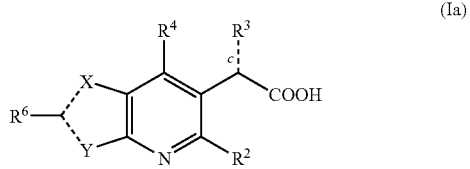

(Ia)

wherein c, X, Y, $R^2$, $R^3$, $R^4$ and $R^6$ are as defined herein.

It will be apparent to a person skilled in the art that, when bond c is a single bond, the carbon atom bonded to the —COOH and $R^3$ substituents can exist in two possible stereochemical configurations, as shown in formulas (Ib) and (Ic) below:

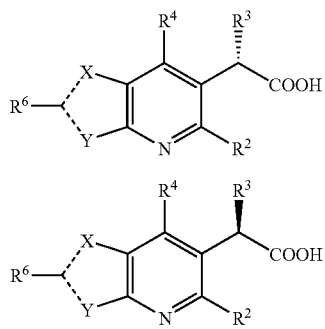

wherein X, Y, $R^2$, $R^3$, $R^4$ and $R^6$ are as defined herein.

It has been found that compounds of formula (Ib) have improved activity over compounds of formula (Ic).

Core-B: Therefore, in one embodiment, the compounds of the present invention are represented by formula (Ib):

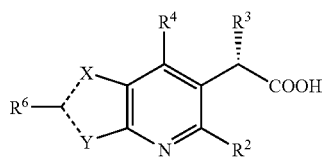

wherein X, Y, $R^2$, $R^3$, $R^4$ and $R^6$ are as defined herein.

Core-C: In another embodiment, the compounds of the present invention are represented by formula (Ic):

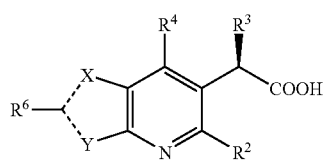

wherein X, Y, $R^2$, $R^3$, $R^4$ and $R^6$ are as defined herein.

Core-D: In another embodiment, the compounds of the invention are represented by formula (Id):

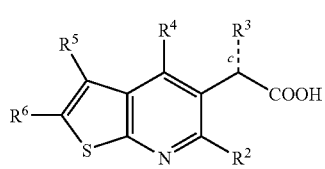

wherein c, $R^2$, $R^3$, $R^4$, $R^5$ and $R^6$ are as defined herein.

It will be apparent to a person skilled in the art that, when bond c is a single bond, the carbon atom bonded to the —COOH and $R^3$ substituents can exist in two possible stereochemical configurations, as shown in formulas (Ie) and (If) below:

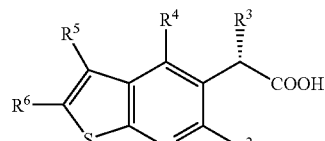

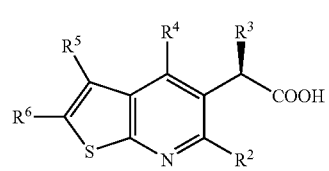

wherein $R^2$, $R^3$, $R^4$, $R^5$ and $R^6$ are as defined herein.

Core-E: In another embodiment, the compounds of the invention are represented by formula (Ie):

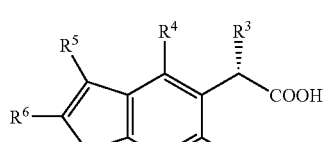

wherein $R^2$, $R^3$, $R^4$, $R^5$ and $R^6$ are as defined herein.

Core-F: In another embodiment, the compounds of the invention are represented by formula (If):

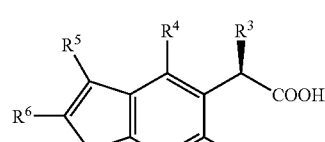

wherein $R^2$, $R^3$, $R^4$, $R^5$ and $R^6$ are as defined herein.

Core-G: In another embodiment, the compounds of the invention are represented by formula (Ig):

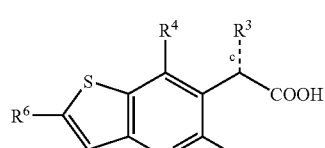

wherein c, $R^2$, $R^3$, $R^4$, $R^6$ and $R^7$ are as defined herein.

It will be apparent to a person skilled in the art that, when bond c is a single bond, the carbon atom bonded to the —COOH and $R^3$ substituents can exist in two possible stereochemical configurations, as shown in formulas (Ih) and (Ii) below:

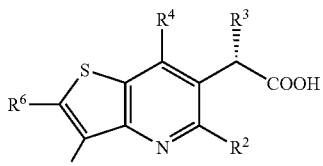

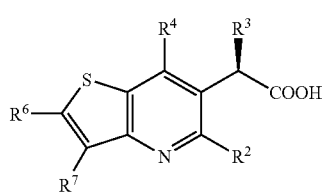

wherein $R^2$, $R^3$, $R^4$, $R^6$ and $R^7$ are as defined herein.

Core-H: In one embodiment, the compounds of the invention are represented by formula (Ih):

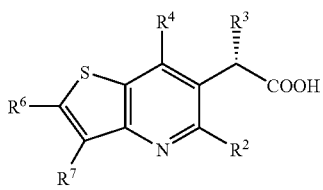

wherein $R^2$, $R^3$, $R^4$, $R^6$ and $R^7$ are as defined herein.

Core-I: In an alternative embodiment, the compounds of the invention are represented by formula (Ii):

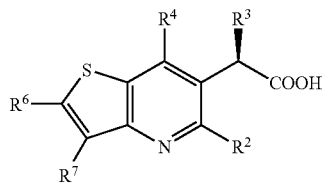

wherein $R^2$, $R^3$, $R^4$, $R^6$ and $R^7$ are as defined herein.

Any and each individual definition of the Core as set out herein may be combined with any and each individual definition of c, X, Y, $R^2$, $R^3$, $R^4$, $R^5$, $R^6$ and $R^7$ as set out herein.

$R^2$:

$R^2$-A: In one embodiment, $R^2$ is selected from:
a) halo;
b) $R^8$, —C(=O)—$R^8$, —C(=O)—O—$R^8$, —O—$R^8$, —S—$R^8$, SO—$R^8$, —SO$_2$—$R^8$, —(C$_{1-6}$)alkylene-$R^8$, —(C$_{1-6}$)alkylene-C(=O)—$R^8$, —(C$_{1-6}$)alkylene-C(=O)—O—$R^8$, —(C$_{1-6}$)alkylene-SO—$R^8$ or —(C$_{1-6}$)alkylene-SO$_2$—$R^8$, —(C$_{1-6}$)alkylene-O—$R^8$ or —(C$_{1-6}$)alkylene-S—$R^8$;
wherein $R^8$ is in each instance independently selected from H, (C$_{1-6}$)alkyl, (C$_{2-6}$)alkenyl, (C$_{2-6}$)alkynyl, (C$_{1-6}$)haloalkyl, (C$_{3-7}$)cycloalkyl, aryl and Het; and
wherein each of the aryl and Het is optionally substituted with 1 to 3 substituents each independently selected from:
i) halo, oxo, thioxo, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —O (C$_{1-6}$)haloalkyl, —SH, —S(C$_{1-6}$)alkyl, —SO(C$_{1-6}$)alkyl, —SO$_2$(C$_{1-6}$)alkyl, —NH$_2$, —NH(C$_{1-6}$)alkyl and —N((C$_{1-6}$)alkyl)$_2$;
ii) (C$_{1-6}$)alkyl optionally substituted with —OH, —O—(C$_{1-6}$)haloalkyl, or —O—(C$_{1-6}$)alkyl; and
iii) aryl or Het, wherein each of the aryl and Het is optionally substituted with halo or (C$_{1-6}$)alkyl; and
c) —N($R^9$)$R^{10}$, —C(=O)—N($R^9$)$R^{10}$, —O—C(=O)—N($R^9$)$R^{10}$, —SO$_2$—N($R^9$)$R^{10}$, —(C$_{1-6}$)alkylene-N($R^9$)$R^{10}$, —(C$_{1-6}$)alkylene-C(=O)—N($R^9$)$R^{10}$, —(C$_{1-6}$)alkylene-O—C(=O)—N($R^9$)$R^{10}$, or —(C$_{1-6}$)alkylene-SO$_2$—N($R^9$)$R^{10}$ wherein
$R^9$ is in each instance independently selected from H, (C$_{1-6}$)alkyl and (C$_{3-7}$)cycloalkyl; and
$R^{10}$ is in each instance independently selected from $R^8$, —(C$_{1-6}$)alkylene-$R^8$, —SO$_2$—$R^8$, —C(=O)—$R^8$, —C(=O)O$R^8$ and —C(=O)N($R^9$)$R^8$; wherein $R^8$ and $R^9$ are as defined above.

$R^2$-B: In an alternative embodiment, $R^2$ is (C$_{1-6}$)alkyl or —O(C$_{1-6}$)alkyl.

$R^2$-C: In another embodiment, $R^2$ is (C$_{1-4}$)alkyl.

$R^2$-D: In another embodiment, $R^2$ is selected from (C$_{1-6}$)alkyl, (C$_{1-6}$)haloalkyl, (C$_{3-7}$)cycloalkyl, (C$_{1-6}$)alkyl-(C$_{3-7}$)cycloalkyl, Het, aryl, (C$_{1-6}$)alkyl-Het and (C$_{1-6}$)alkyl-aryl.

$R^2$-E: In another embodiment, $R^2$ is selected from (C$_{1-6}$)alkyl, (C$_{1-6}$)haloalkyl, (C$_{3-7}$)cycloalkyl, (C$_{1-6}$)alkyl-(C$_{3-7}$)cycloalkyl, —S(C$_{1-6}$)alkyl, —NH$_2$, —NH(C$_{1-6}$)alkyl, —N((C$_{1-6}$)alkyl)$_2$, Het, aryl, (C$_{1-6}$)alkyl-Het and (C$_{1-6}$)alkyl-aryl.

$R^2$-F: In another embodiment, $R^2$ is —CH$_3$, —CH$_2$CH$_3$, —CH(CH$_3$)$_2$, or —OCH$_3$.

$R^2$-G: In another embodiment, $R^2$ is —CH$_3$ or —CH$_2$CH$_3$.

$R^2$-H: In another embodiment, $R^2$ is —CH$_3$.

Any and each individual definition of $R^2$ as set out herein may be combined with any and each individual definition of the Core, c, X, Y, $R^3$, $R^4$, $R^5$, $R^6$ and $R^7$ as set out herein.

$R^3$:

$R^3$-A: In one embodiment, $R^3$ is (C$_{1-6}$)alkyl, (C$_{1-6}$)haloalkyl, (C$_{2-6}$)alkenyl, (C$_{2-6}$)alkynyl, (C$_{3-7}$)cycloalkyl-(C$_{1-6}$)alkyl-, aryl-(C$_{1-6}$)alkyl-, Het-(C$_{1-6}$)alkyl- or —W—$R^{31}$, and bond c is a single bond; or
$R^3$ is (C$_{1-6}$)alkylidene and bond c is a double bond;
wherein W is O or S and $R^{31}$ is (C$_{1-6}$)alkyl, (C$_{1-6}$)haloalkyl, (C$_{2-6}$)alkenyl, (C$_{2-6}$)alkynyl, (C$_{3-7}$)cycloalkyl, aryl, (C$_{3-7}$)cycloalkyl-(C$_{1-6}$)alkyl-, aryl-(C$_{1-6}$)alkyl- or Het-(C$_{1-6}$)alkyl-;
wherein each of the (C$_{1-6}$)alkylidene, (C$_{1-6}$)alkyl, (C$_{1-6}$)haloalkyl, (C$_{2-6}$)alkenyl, (C$_{2-6}$)alkynyl, (C$_{3-7}$)cycloalkyl-(C$_{1-6}$)alkyl-, Het-(C$_{1-6}$)alkyl- and —W—$R^{31}$ is optionally substituted with 1 to 3 substituents each independently selected from (C$_{1-6}$)alkyl, halo, cyano, oxo and —O(C$_{1-6}$)alkyl.

$R^3$-B: In one embodiment, $R^3$ is (C$_{1-6}$)alkyl, (C$_{1-6}$)haloalkyl, (C$_{2-6}$)alkenyl, (C$_{2-6}$)alkynyl, (C$_{3-7}$)cycloalkyl-(C$_{1-6}$)alkyl-, aryl-(C$_{1-6}$)alkyl- or Het-(C$_{1-6}$)alkyl-;
wherein each of the (C$_{1-6}$)alkyl, (C$_{1-6}$)haloalkyl, (C$_{2-6}$)alkenyl, (C$_{2-6}$)alkynyl, (C$_{3-7}$)cycloalkyl-(C$_{1-6}$)alkyl-, aryl-(C$_{1-6}$)alkyl- and Het-(C$_{1-6}$)alkyl- is optionally substituted with 1 to 3 substituents each independently selected from (C$_{1-6}$)alkyl, halo, cyano, oxo and —O(C$_{1-6}$)alkyl; and
bond c is a single bond.

$R^3$-C: In another embodiment, $R^3$ is (C$_{1-6}$)alkyl or (C$_{2-6}$)alkenyl; and
bond c is a single bond.

R³-D: In an alternative embodiment, R³ is —W—(C$_{1-6}$)alkyl, —W—(C$_{1-6}$)haloalkyl, —W—(C$_{2-6}$)alkenyl, —W—(C$_{2-6}$)alkynyl, —W—(C$_{3-7}$)cycloalkyl, —W-aryl, (C$_{3-7}$)cycloalkyl-(C$_{1-6}$)alkyl-W—, aryl-(C$_{1-6}$)alkyl-W— or Het-(C$_{1-6}$)alkyl-W—;
wherein W is O or S; and
wherein each of the —W—(C$_{1-6}$)alkyl, —W—(C$_{2-6}$)alkenyl, —W—(C$_{2-6}$)alkynyl, —W—(C$_{3-7}$)cycloalkyl, —W-aryl, (C$_{3-7}$)cycloalkyl-(C$_{1-6}$)alkyl-W—, aryl-(C$_{1-6}$)alkyl-W— and Het-(C$_{1-6}$)alkyl-W— is optionally substituted with 1 to 3 substituents each independently selected from (C$_{1-6}$)alkyl, halo, cyano, oxo and —O(C$_{1-6}$)alkyl;
and
bond c is a single bond.

R³-E: In another embodiment, R³ is —O—(C$_{1-6}$)alkyl, —O—(C$_{1-6}$)haloalkyl, —O—(C$_{2-6}$)alkenyl, —O—(C$_{2-6}$)alkynyl, —O—(C$_{3-7}$)cycloalkyl, —O-aryl, (C$_{3-7}$)cycloalkyl-(C$_{1-6}$)alkyl-O—, aryl-(C$_{1-6}$)alkyl-O— or Het-(C$_{1-6}$)alkyl-O—;
wherein each of the —O—(C$_{1-6}$)alkyl, —O—(C$_{2-6}$)alkenyl, —O—(C$_{2-6}$)alkynyl, —O—(C$_{3-7}$)cycloalkyl, —O-aryl, (C$_{3-7}$)cycloalkyl-(C$_{1-6}$)alkyl-O—, aryl-(C$_{1-6}$)alkyl-O— and Het-(C$_{1-6}$)alkyl-O— is optionally substituted with 1 to 3 substituents each independently selected from (C$_{1-6}$)alkyl, halo, cyano, oxo and —O(C$_{1-6}$)alkyl;
and
bond c is a single bond.

R³-F: In another embodiment, R³ is —O(C$_{1-6}$)alkyl, —O—(C$_{2-6}$)alkenyl, —O(C$_{2-6}$)alkynyl, —O—(C$_{3-7}$)cycloalkyl, —O-aryl, (C$_{3-7}$)cycloalkyl-(C$_{1-3}$)alkyl-O— or Het-(C$_{1-3}$)alkyl-O—;
wherein Het is a 5- or 6-membered heterocycle having 1 to 3 heteroatoms each independently selected from N, O and S; and
wherein each of the —O(C$_{1-6}$)alkyl, —O—(C$_{3-7}$)cycloalkyl and Het-(C$_{1-3}$)alkyl-O— is optionally substituted with 1 to 3 substituents each independently selected from (C$_{1-3}$)alkyl, cyano, oxo and —O(C$_{1-6}$)alkyl; and
bond c is a single bond.

R³-G: In another embodiment, R³ is —O(C$_{1-6}$)alkyl, —O—(C$_{1-6}$)haloalkyl, —O(C$_{2-6}$)alkenyl, —O(C$_{2-6}$)alkynyl or —O—(C$_{3-7}$)cycloalkyl;
wherein each of the —O(C$_{1-6}$)alkyl and —O—(C$_{3-7}$)cycloalkyl is optionally substituted with 1 to 3 substituents each independently selected from (C$_{1-3}$)alkyl, cyano, oxo and —O(C$_{1-6}$)alkyl; and
bond c is a single bond.

R³-H: In another embodiment, R³ is —O(C$_{1-4}$)alkyl; wherein the —O(C$_{1-4}$)alkyl is optionally substituted with 1 to 2 substituents each independently selected from cyano, oxo and —O(C$_{1-6}$)alkyl; and
bond c is a single bond.

R³-I: In another embodiment, R³ is —OC(CH$_3$)$_3$; and bond c is a single bond.

R³-J: In another embodiment, R³ is selected from:

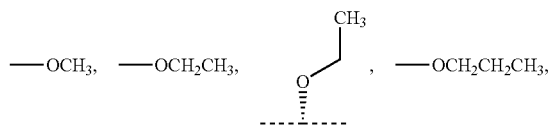

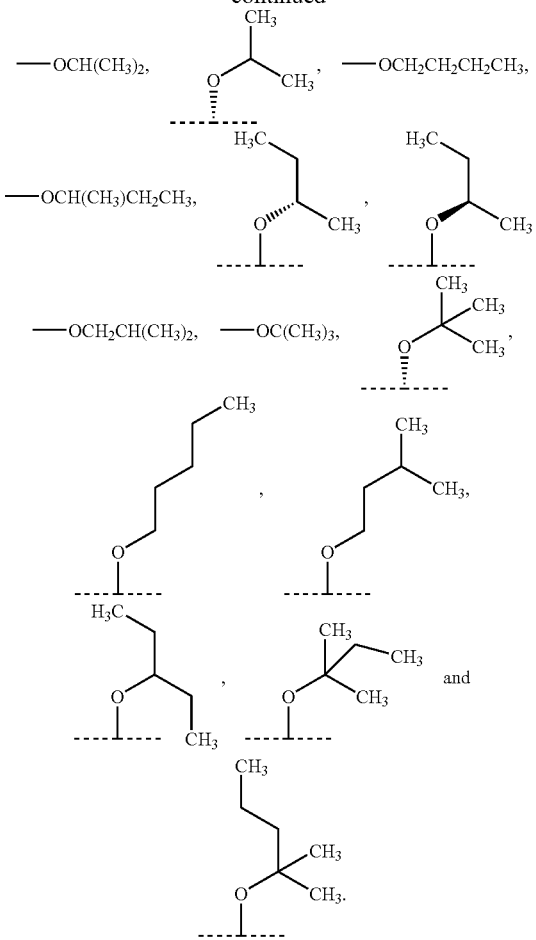

Any and each individual definition of c and R³ as set out herein may be combined with any and each individual definition of the Core, X, Y, R², R⁴, R⁵, R⁶ and R⁷ as set out herein.

R⁴:

R⁴-A: In one embodiment, R⁴ is aryl or Het, wherein each of the aryl and Het is optionally substituted with 1 to 5 substituents each independently selected from halo, (C$_{1-6}$)alkyl, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —SH, —S(C$_{1-6}$)alkyl, —NH$_2$, —NH(C$_{1-6}$)alkyl and —N((C$_{1-6}$)alkyl)$_2$; wherein the (C$_{1-6}$)alkyl is optionally substituted with hydroxy, —O(C$_{1-6}$)alkyl, cyano or oxo.

R⁴-B: In one embodiment, R⁴ is aryl optionally substituted with 1 to 3 substituents each independently selected from halo, (C$_{1-6}$)alkyl, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —SH, —S(C$_{1-6}$)alkyl, —NH$_2$, —NH(C$_{1-6}$)alkyl and —N((C$_{1-6}$)alkyl)$_2$; wherein the (C$_{1-6}$)alkyl is optionally substituted with hydroxy, —O(C$_{1-6}$)alkyl, cyano or oxo.

R⁴-C: In another embodiment, R⁴ is phenyl optionally substituted with 1 to 3 substituents each independently selected from halo, (C$_{1-4}$)alkyl, (C$_{2-4}$)alkenyl, (C$_{1-4}$)haloalkyl, (C$_{3-7}$)cycloalkyl, —OH, —O(C$_{1-4}$)alkyl, —SH, —S(C$_{1-4}$)alkyl, —NH$_2$, —NH(C$_{1-4}$)alkyl and —N((C$_{1-4}$)alkyl)$_2$.

R⁴-D: In another embodiment, R⁴ is phenyl optionally substituted with 1 to 3 substituents each independently selected from F, Cl, Br, NH$_2$, —CH$_3$, —CH$_2$CH$_3$, —CH$_2$CH$_2$CH$_3$, CH$_2$F, CF$_3$ and —CH$_2$CH$_2$F.

R⁴-E: In another embodiment, R⁴ is selected from:

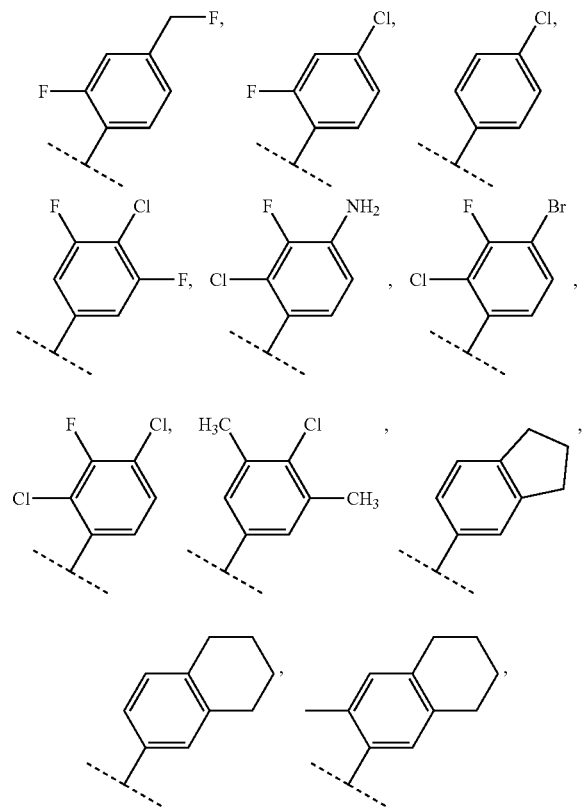

R⁴-F: In an alternative embodiment, R⁴ is Het optionally substituted with 1 to 3 substituents each independently selected from halo, (C₁₋₆)alkyl, (C₂₋₆)alkenyl, (C₁₋₆)haloalkyl, (C₃₋₇)cycloalkyl, —OH, —O(C₁₋₆)alkyl, —SH, —S(C₁₋₆)alkyl, —NH₂, —NH(C₁₋₆)alkyl and —N((C₁₋₆)alkyl)₂; wherein the (C₁₋₆)alkyl is optionally substituted with hydroxyl or —O(C₁₋₆)alkyl.

R⁴-G: In another alternative embodiment, R⁴ is Het optionally substituted with 1 or 2 substituents each independently selected from halo, (C₁₋₆)alkyl and —O(C₁₋₆)alkyl;
wherein the Het is a 5- or 6-membered heterocycle having 1 to 3 heteroatoms each independently selected from N, O and S; or the Het is a 9- or 10-membered heteropolycycle having 1 to 3 heteroatoms each independently selected from N, O and S.

R⁴-H: In another alternative embodiment, R⁴ is aryl or Het optionally substituted with 1 to 3 substituents each independently selected from halo, (C₁₋₆)alkyl, (C₁₋₆)haloalkyl, NH₂ and —O(C₁₋₆)alkyl;

wherein the aryl is selected from:

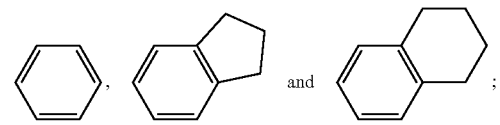

and
wherein the Het is selected from:

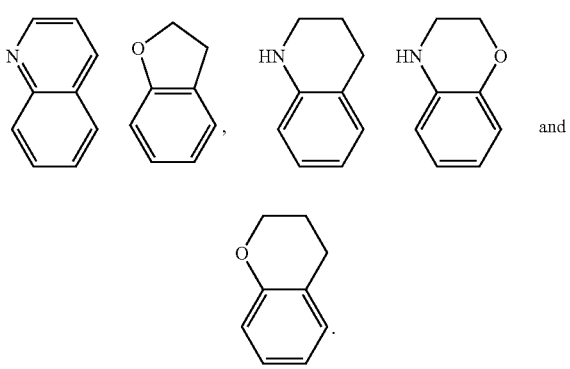

R⁴-I: In another alternative embodiment, R⁴ is selected from:

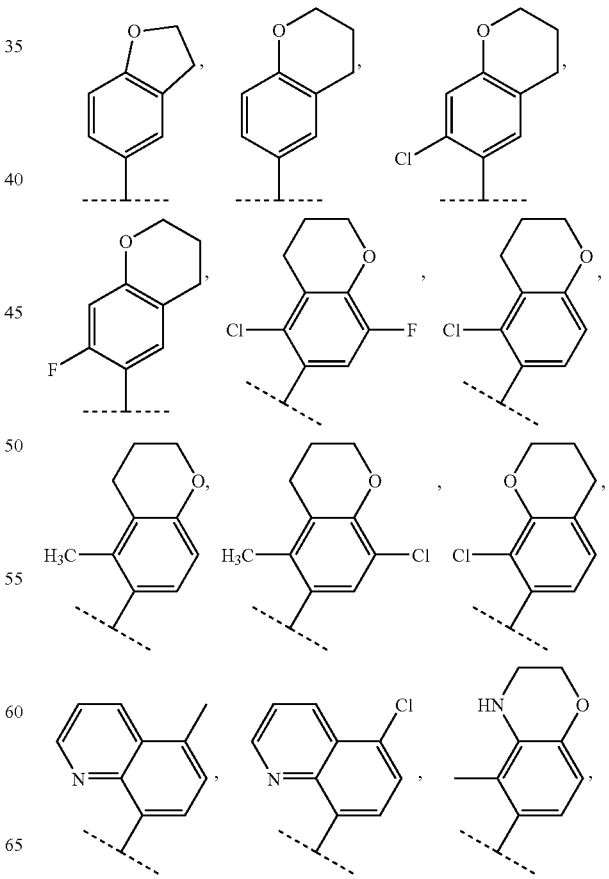

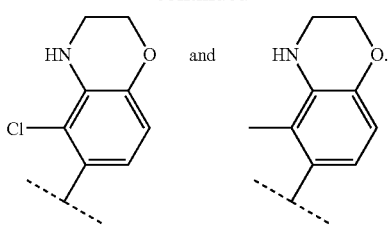

One skilled in the art will recognize that when the $R^4$ substituent is not symmetrically substituted about the axis of rotation of the bond attaching $R^4$ to Core, rotational isomers or atropisomers are possible. Compounds of the invention in which the $R^4$ substituent is not symmetrically substituted about the axis of rotation of the bond attaching $R^4$ to Core and in which the carbon atom bonded to the —COOH and $R^3$ substituents is chiral, as described above, will have two chiral centers, a chiral carbon atom and a rotational axis of asymmetry, and thus the atropisomers will exist as diastereomers. However, individual diastereomeric atropisomers may or may not be detectable and/or separable, depending upon the relative amounts of each atropisomer formed during synthesis, present at equilibrium, and the degree of steric hindrance to rotation about the C-4 chiral axis, and therefore, the rate at which interconversion between these atropoisomers occurs. Once separated, individual atropoisomers may be very stable or interconvert, rapidly or slowly, with each other to form an equilibrium mixture of atropoisomers.

$R^4$-J: In another alternative embodiment, $R^4$ is selected from:

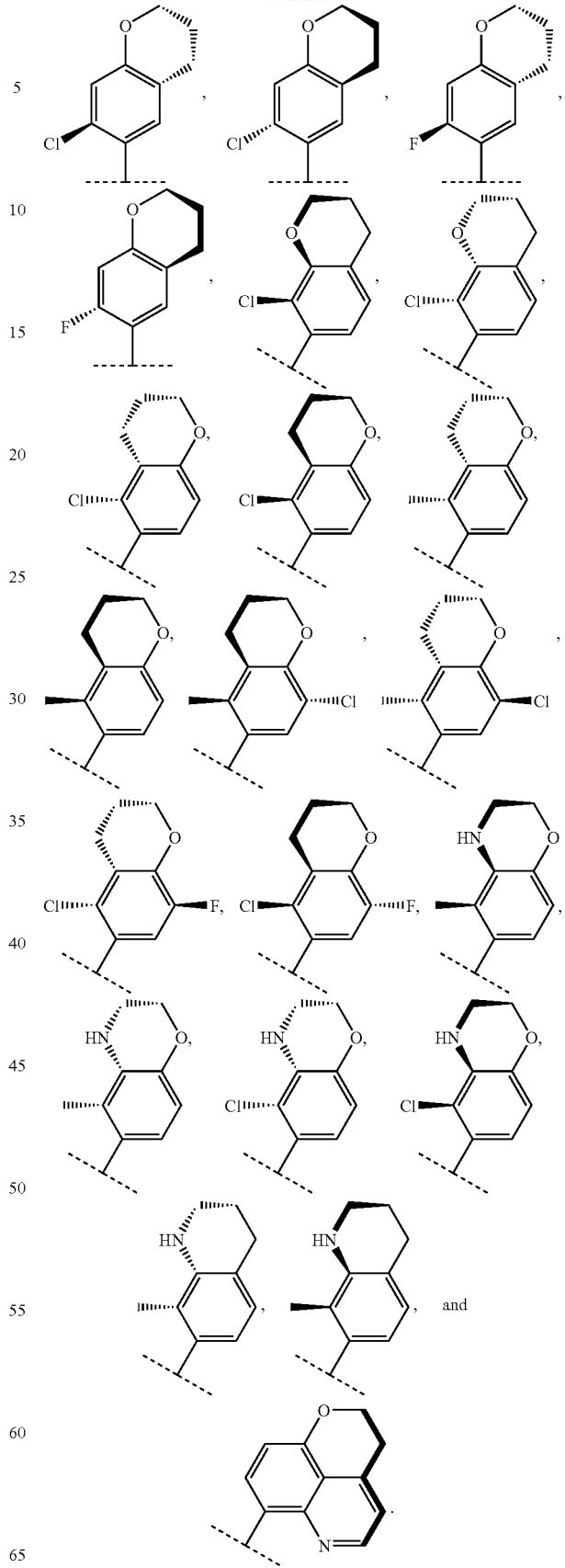

$R^4$-K: In another alternative embodiment, $R^4$ is selected from:
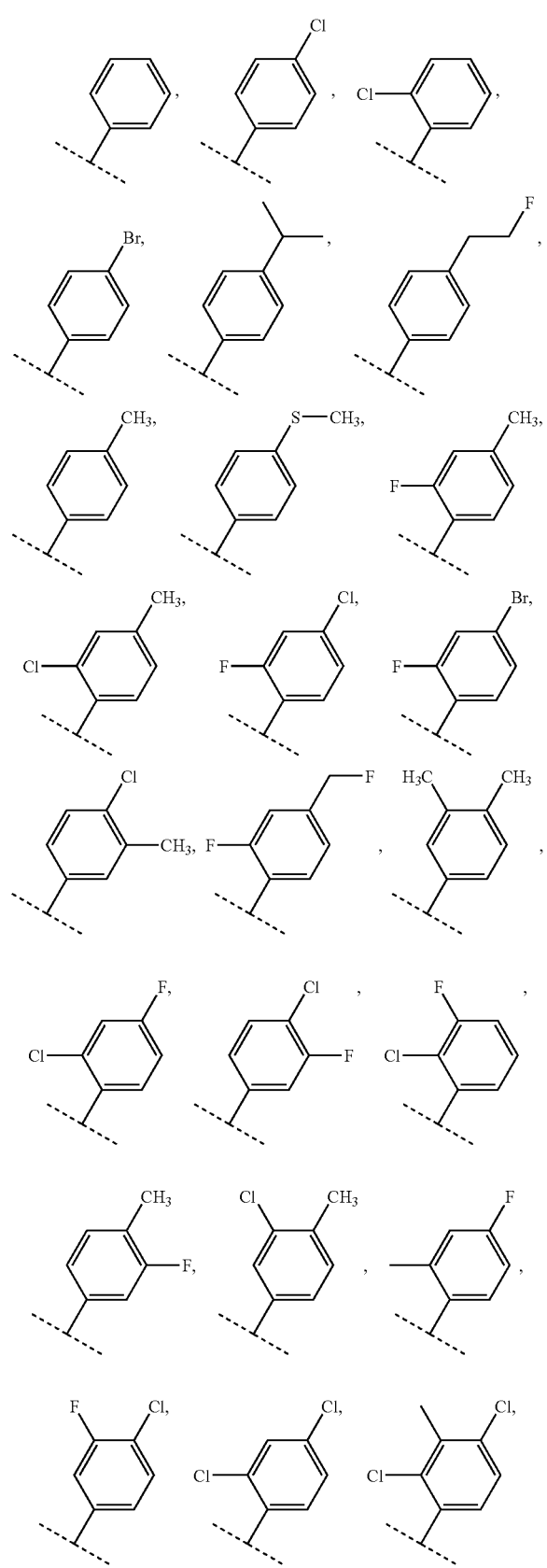
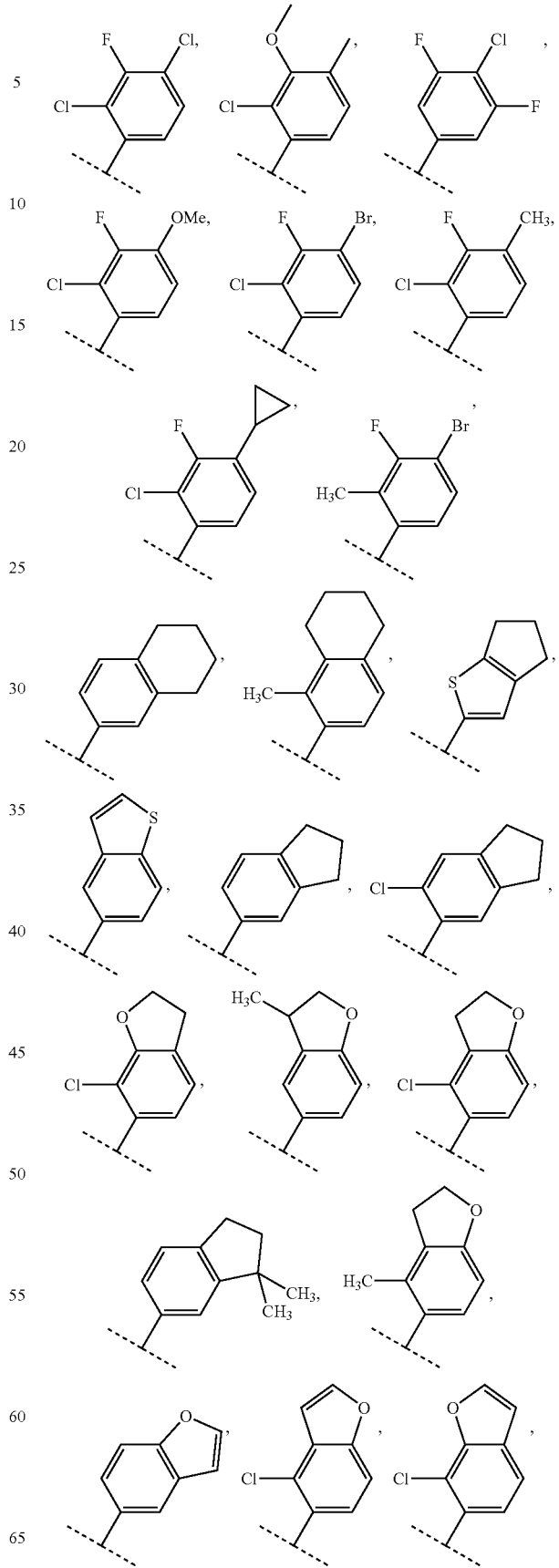

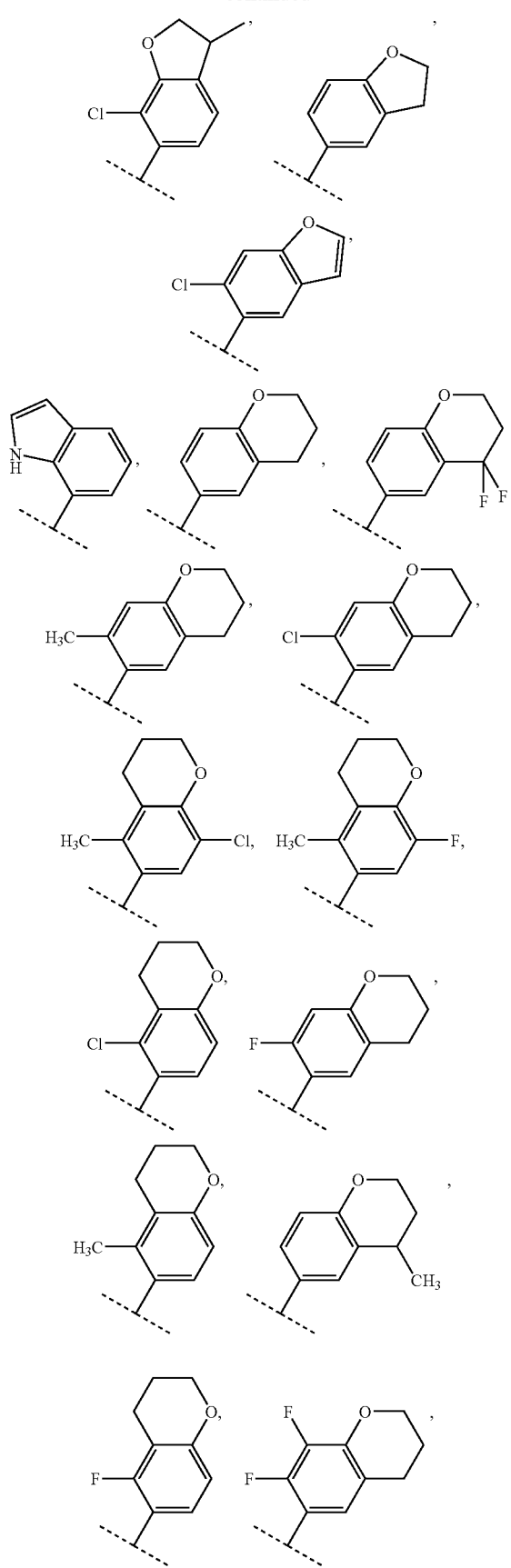
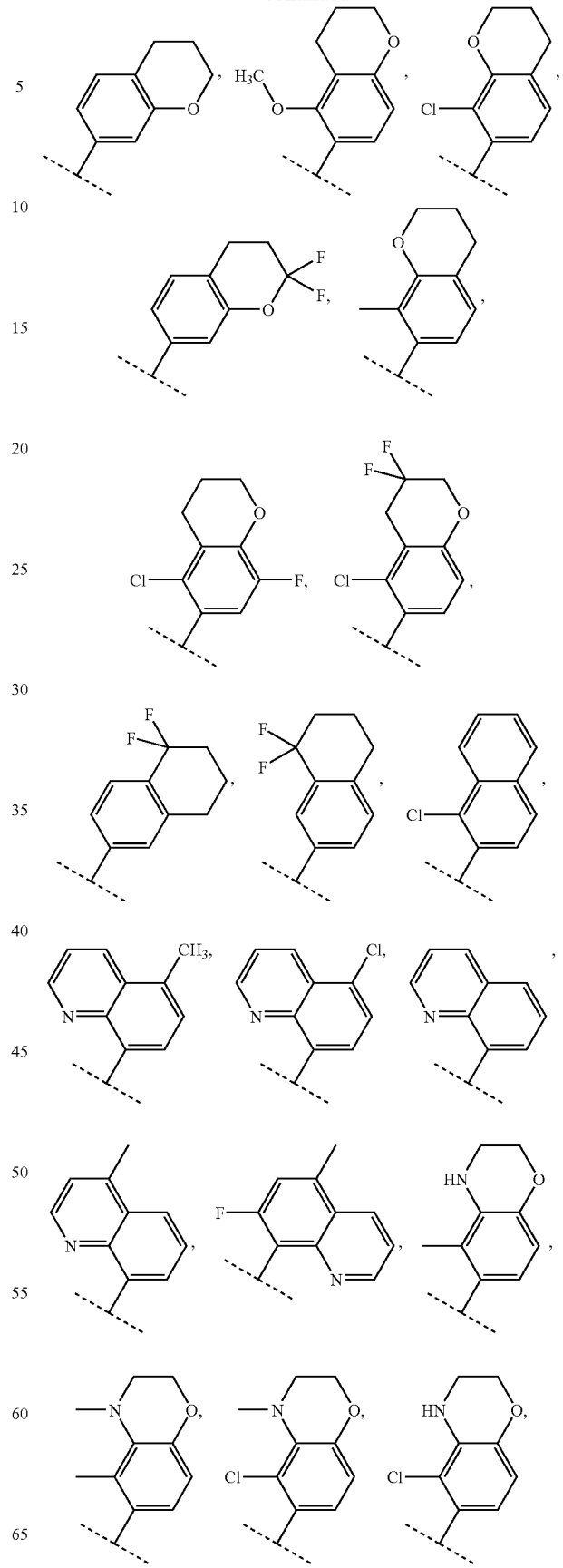

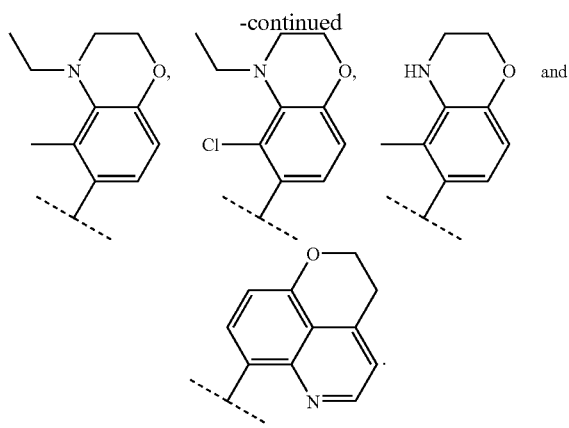

Any and each individual definition of $R^4$ as set out herein may be combined with any and each individual definition of the Core, c, X, Y, $R^2$, $R^3$, $R^5$, $R^6$ and $R^7$ as set out herein.

$R^5$:

$R^5$-A: In one embodiment, $R^5$ is selected from:
a) halo;
b) $R^8$, —C(=O)—$R^8$, —C(=O)—O—$R^8$, —O—$R^8$, —S—$R^8$, SO—$R^8$, —SO$_2$—$R^8$, —(C$_{1-6}$)alkylene-$R^8$, —(C$_{1-6}$)alkylene-C(=O)—$R^8$, —(C$_{1-6}$)alkylene-C(=O)—O—$R^8$, —(C$_{1-6}$)alkylene-SO—$R^8$ or —(C$_{1-6}$)alkylene-SO$_2$—$R^8$, —(C$_{1-6}$)alkylene-O—$R^8$ or —(C$_{1-6}$)alkylene-S—$R^8$;
 wherein $R^8$ is in each instance independently selected from H, (C$_{1-6}$)alkyl, (C$_{2-6}$)alkenyl, (C$_{2-6}$)alkynyl, (C$_{1-6}$)haloalkyl, (C$_{3-7}$)cycloalkyl, aryl and Het;
 and
 wherein each of the aryl and Het is optionally substituted with 1 to 3 substituents each independently selected from:
  i) halo, oxo, thioxo, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —O (C$_{1-6}$)haloalkyl, —SH, —S(C$_{1-6}$)alkyl, —SO(C$_{1-6}$)alkyl, —SO$_2$(C$_{1-6}$)alkyl, —NH$_2$, —NH(C$_{1-6}$)alkyl and —N((C$_{1-6}$)alkyl)$_2$;
  ii) (C$_{1-6}$)alkyl optionally substituted with —OH, —O—(C$_{1-6}$)haloalkyl, or —O—(C$_{1-6}$)alkyl;
  iii) aryl or Het, wherein each of the aryl and Het is optionally substituted with halo or (C$_{1-6}$)alkyl; and
c) —N($R^9$)$R^{10}$, —C(=O)—N($R^9$)$R^{10}$, —O—C(=O)—N($R^9$)$R^{10}$, —SO$_2$—N($R^9$)$R^{10}$, —(C$_{1-6}$)alkylene-N($R^9$)$R^{10}$, —(C$_{1-6}$)alkylene-C(=O)—N($R^9$)$R^{10}$, —(C$_{1-6}$)alkylene-O—C(=O)—N($R^9$)$R^{10}$, or —(C$_{1-6}$)alkylene-SO$_2$—N($R^9$)$R^{10}$ wherein
 $R^9$ is in each instance independently selected from H, (C$_{1-6}$)alkyl and (C$_{3-7}$)cycloalkyl; and
 $R^{10}$ is in each instance independently selected from $R^8$, —(C$_{1-6}$)alkylene-$R^8$, —SO$_2$—$R^8$, —C(=O)—$R^8$, —C(=O)O$R^8$ and —C(=O)N($R^9$)$R^8$; wherein $R^8$ and $R^9$ are as defined above.

$R^5$-C: In another embodiment, $R^5$ is (C$_{1-4}$)alkyl.
$R^5$-D: In another embodiment, $R^5$ is H or (C$_{1-4}$)alkyl.
$R^5$-E: In another embodiment, $R^5$ is H or CH$_3$.
$R^5$-F: In another embodiment, $R^5$ is H, (C$_{1-6}$)alkyl or (C$_{1-6}$)haloalkyl.

Any and each individual definition of $R^5$ as set out herein may be combined with any and each individual definition of the Core, c, X, Y, $R^2$, $R^3$, $R^4$ and $R^6$ as set out herein.

$R^6$:

$R^6$-A: In one embodiment, $R^6$ is selected from:
a) halo;
b) $R^8$, —C(=O)—$R^8$, —C(=O)—O—$R^8$, —O—$R^8$, —S—$R^8$, SO—$R^8$, —SO$_2$—$R^8$, —(C$_{1-6}$)alkylene-$R^8$, —(C$_{1-6}$)alkylene-C(=O)—$R^8$, —(C$_{1-6}$)alkylene-C(=O)—O—$R^8$, —(C$_{1-6}$)alkylene-SO—$R^8$ or —(C$_{1-6}$)alkylene-SO$_2$—$R^8$, —(C$_{1-6}$)alkylene-O—$R^8$ or —(C$_{1-6}$)alkylene-S—$R^8$;
 wherein $R^8$ is in each instance independently selected from H, (C$_{1-6}$)alkyl, (C$_{2-6}$)alkenyl, (C$_{2-6}$)alkynyl, (C$_{1-6}$)haloalkyl, (C$_{3-7}$)cycloalkyl, aryl and Het;
 and
 wherein each of the aryl and Het is optionally substituted with 1 to 3 substituents each independently selected from:
  i) halo, oxo, thioxo, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —O (C$_{1-6}$)haloalkyl, —SH, —S(C$_{1-6}$)alkyl, —SO(C$_{1-6}$)alkyl, —SO$_2$(C$_{1-6}$)alkyl, —NH$_2$, —NH(C$_{1-6}$)alkyl and —N((C$_{1-6}$)alkyl)$_2$;
  ii) (C$_{1-6}$)alkyl optionally substituted with —OH, —O—(C$_{1-6}$)haloalkyl, or —O—(C$_{1-6}$)alkyl;
  iii) aryl or Het, wherein each of the aryl and Het is optionally substituted with halo or (C$_{1-6}$)alkyl; and
c) —N($R^9$)$R^{10}$, —C(=O)—N($R^9$)$R^{10}$, —O—C(=O)—N($R^9$)$R^{10}$, —SO$_2$—N($R^9$)$R^{10}$, —(C$_{1-6}$)alkylene-N($R^9$)$R^{10}$, —(C$_{1-6}$)alkylene-C(=O)—N($R^9$)$R^{10}$, —(C$_{1-6}$)alkylene-O—C(=O)—N($R^9$)$R^{10}$, or —(C$_{1-6}$)alkylene-SO$_2$—N($R^9$)$R^{10}$ wherein
 $R^9$ is in each instance independently selected from H, (C$_{1-6}$)alkyl and (C$_{3-7}$)cycloalkyl; and
 $R^{10}$ is in each instance independently selected from $R^8$, —(C$_{1-6}$)alkylene-$R^8$, —SO$_2$—$R^8$, —C(=O)—$R^8$, —C(=O)O$R^8$ and —C(=O)N($R^9$)$R^8$; wherein $R^8$ and $R^9$ are as defined above.

$R^6$-B: In another embodiment, $R^6$ is H, (C$_{1-6}$)alkyl, (C$_{3-7}$)cycloalkyl or —O(C$_{1-6}$)alkyl.
$R^6$-C: In another embodiment, $R^6$ is (C$_{1-4}$)alkyl.
$R^6$-D: In another embodiment, $R^6$ is H or (C$_{1-4}$)alkyl.
$R^6$-E: In another embodiment, $R^6$ is H or CH$_3$.
$R^6$-F: In another embodiment, $R^6$ is H, (C$_{1-6}$)alkyl or (C$_{1-6}$)haloalkyl.

Any and each individual definition of $R^6$ as set out herein may be combined with any and each individual definition of the Core, c, X, Y, $R^2$, $R^3$, $R^4$, $R^5$ and $R^7$ as set out herein.

$R^7$:

$R^7$-A: In one embodiment, $R^7$ is selected from:
a) halo;
b) $R^8$, —C(=O)—$R^8$, —C(=O)—O—$R^8$, —O—$R^8$, —S—$R^8$, SO—$R^8$, —SO$_2$—$R^8$, —(C$_{1-6}$)alkylene-$R^8$, —(C$_{1-6}$)alkylene-C(=O)—$R^8$, —(C$_{1-6}$)alkylene-C(=O)—O—$R^8$, —(C$_{1-6}$)alkylene-SO—$R^8$ or —(C$_{1-6}$)alkylene-SO$_2$—$R^8$, —(C$_{1-6}$)alkylene-O—$R^8$ or —(C$_{1-6}$)alkylene-S—$R^8$;
 wherein $R^8$ is in each instance independently selected from H, (C$_{1-6}$)alkyl, (C$_{2-6}$)alkenyl, (C$_{2-6}$)alkynyl, (C$_{1-6}$)haloalkyl, (C$_{3-7}$)cycloalkyl, aryl and Het;
 and
 wherein each of the aryl and Het is optionally substituted with 1 to 3 substituents each independently selected from:
  i) halo, oxo, thioxo, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —O (C$_{1-6}$)haloalkyl, —SH, —SO(C$_{1-6}$)alkyl, —SO$_2$(C$_{1-6}$)alkyl, —NH$_2$, —NH(C$_{1-6}$)alkyl and —N((C$_{1-6}$)alkyl)$_2$;

ii) $(C_{1-6})$alkyl optionally substituted with —OH, —O—$(C_{1-6})$haloalkyl, or —O—$(C_{1-6})$alkyl; and iii) aryl or Het, wherein each of the aryl and Het is optionally substituted with halo or $(C_{1-6})$alkyl; and c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —$(C_{1-6})$alkylene-N(R$^9$)R$^{10}$, —$(C_{1-6})$alkylene-C(=O)—N(R$^9$)R$^{10}$, —$(C_{1-6})$alkylene-O—C(=O)—N(R$^9$)R$^{10}$, or —$(C_{1-6})$alkylene-SO$_2$—N(R$^9$)R$^{10}$ wherein R$^9$ is in each instance independently selected from H, $(C_{1-6})$alkyl and $(C_{3-7})$cycloalkyl; and R$^{10}$ is in each instance independently selected from R$^8$, —$(C_{1-6})$alkylene-R$^8$, —SO$_2$—R$^8$, —C(=O)—R$^8$, —C(=O)OR$^8$ and —C(=O)N(R$^9$)R$^8$; wherein R$^8$ and R$^9$ are as defined above.

R$^7$-B: In another embodiment, R$^7$ is H, $(C_{1-6})$alkyl, $(C_{3-7})$cycloalkyl or —O$(C_{1-6})$alkyl.

R$^7$-C: In another embodiment, R$^7$ is $(C_{1-4})$alkyl.

R$^7$-D: In another embodiment, R$^7$ is H or $(C_{1-4})$alkyl.

R$^7$-E: In another embodiment, R$^7$ is H or CH$_3$.

R$^7$-F: In another embodiment, R$^7$ is H, $(C_{1-6})$alkyl or $(C_{1-6})$haloalkyl.

Any and each individual definition of R$^7$ as set out herein may be combined with any and each individual definition of the Core, c, X, Y, R$^2$, R$^3$, R$^4$ and R$^6$ as set out herein.

Examples of preferred subgeneric embodiments of the present invention are set forth in the following table, wherein each substituent group of each embodiment is defined according to the definitions set forth above:

| Embodiment | Core | R$^2$ | R$^3$ | R$^4$ | R$^5$ | R$^6$ | R$^7$ |
|---|---|---|---|---|---|---|---|
| E-1 | Core-A | R$^2$-B | R$^3$-C | R$^4$-B | — | R$^6$-D | R$^7$-B |
| E-2 | Core-A | R$^2$-B | R$^3$-D | R$^4$-C | — | R$^6$-F | R$^7$-A |
| E-3 | Core-A | R$^2$-E | R$^3$-B | R$^4$-E | — | R$^6$-C | R$^7$-C |
| E-4 | Core-A | R$^2$-B | R$^3$-I | R$^4$-E | — | R$^6$-F | R$^7$-F |
| E-5 | Core-A | R$^2$-C | R$^3$-D | R$^4$-G | — | R$^6$-B | R$^7$-B |
| E-6 | Core-A | R$^2$-B | R$^3$-I | R$^4$-J | — | R$^6$-D | R$^7$-D |
| E-7 | Core-A | R$^2$-H | R$^3$-I | R$^4$-J | — | R$^6$-E | R$^7$-E |
| E-8 | Core-A | R$^2$-B | R$^3$-C | R$^4$-B | R$^5$-E | R$^6$-D | — |
| E-9 | Core-A | R$^2$-B | R$^3$-D | R$^4$-C | R$^5$-B | R$^6$-F | — |
| E-10 | Core-A | R$^2$-E | R$^3$-B | R$^4$-E | R$^5$-C | R$^6$-C | — |
| E-11 | Core-A | R$^2$-B | R$^3$-I | R$^4$-E | R$^5$-C | R$^6$-F | — |
| E-12 | Core-A | R$^2$-C | R$^3$-D | R$^4$-G | R$^5$-F | R$^6$-B | — |
| E-13 | Core-A | R$^2$-H | R$^3$-I | R$^4$-K | R$^5$-D | R$^6$-D | — |
| E-14 | Core-A | R$^2$-H | R$^3$-I | R$^4$-K | R$^5$-E | R$^6$-E | — |
| E-15 | Core-A | R$^2$-H | R$^3$-I | R$^4$-J | R$^5$-D | R$^6$-D | — |
| E-16 | Core-A | R$^2$-H | R$^3$-I | R$^4$-J | R$^5$-E | R$^6$-E | — |
| E-17 | Core-B | R$^2$-D | R$^3$-G | R$^4$-A | — | R$^6$-B | R$^7$-F |
| E-18 | Core-B | R$^2$-F | R$^3$-B | R$^4$-G | — | R$^6$-E | R$^7$-A |
| E-19 | Core-B | R$^2$-C | R$^3$-E | R$^4$-D | — | R$^6$-C | R$^7$-C |
| E-20 | Core-B | R$^2$-H | R$^3$-I | R$^4$-J | — | R$^6$-D | R$^7$-D |
| E-21 | Core-B | R$^2$-H | R$^3$-I | R$^4$-J | — | R$^6$-E | R$^7$-E |
| E-22 | Core-B | R$^2$-D | R$^3$-G | R$^4$-A | R$^5$-B | R$^6$-B | — |
| E-23 | Core-B | R$^2$-F | R$^3$-B | R$^4$-G | R$^5$-A | R$^6$-E | — |
| E-24 | Core-B | R$^2$-C | R$^3$-E | R$^4$-D | R$^5$-D | R$^6$-C | — |
| E-25 | Core-B | R$^2$-H | R$^3$-I | R$^4$-J | R$^5$-D | R$^6$-D | — |
| E-26 | Core-B | R$^2$-H | R$^3$-I | R$^4$-J | R$^5$-E | R$^6$-E | — |
| E-27 | Core-B | R$^2$-H | R$^3$-I | R$^4$-K | R$^5$-D | R$^6$-D | — |
| E-28 | Core-B | R$^2$-H | R$^3$-I | R$^4$-K | R$^5$-E | R$^6$-E | — |
| E-29 | Core-C | R$^2$-A | R$^3$-H | R$^4$-C | — | R$^6$-E | R$^7$-E |
| E-30 | Core-C | R$^2$-D | R$^3$-B | R$^4$-A | — | R$^6$-B | R$^7$-F |
| E-31 | Core-C | R$^2$-A | R$^3$-H | R$^4$-C | R$^5$-A | R$^6$-E | — |
| E-32 | Core-C | R$^2$-D | R$^3$-B | R$^4$-A | R$^5$-D | R$^6$-B | — |
| E-33 | Core-D | R$^2$-G | R$^3$-I | R$^4$-E | R$^5$-D | R$^6$-D | — |
| E-34 | Core-D | R$^2$-H | R$^3$-J | R$^4$-H | R$^5$-E | R$^6$-E | — |
| E-35 | Core-D | R$^2$-G | R$^3$-I | R$^4$-I | R$^5$-D | R$^6$-E | — |
| E-36 | Core-D | R$^2$-H | R$^3$-J | R$^4$-H | R$^5$-D | R$^6$-E | — |
| E-37 | Core-D | R$^2$-C | R$^3$-I | R$^4$-A | R$^5$-B | R$^6$-E | — |
| E-38 | Core-D | R$^2$-A | R$^3$-F | R$^4$-E | R$^5$-A | R$^6$-E | — |
| E-39 | Core-D | R$^2$-G | R$^3$-H | R$^4$-H | R$^5$-F | R$^6$-D | — |
| E-40 | Core-D | R$^2$-F | R$^3$-E | R$^4$-C | R$^5$-B | R$^6$-B | — |
| E-41 | Core-D | R$^2$-H | R$^3$-J | R$^4$-B | R$^5$-A | R$^6$-D | — |
| E-42 | Core-D | R$^2$-H | R$^3$-I | R$^4$-J | R$^5$-D | R$^6$-D | — |
| E-43 | Core-D | R$^2$-H | R$^3$-I | R$^4$-J | R$^5$-E | R$^6$-E | — |
| E-44 | Core-D | R$^2$-H | R$^3$-I | R$^4$-K | R$^5$-D | R$^6$-D | — |
| E-45 | Core-D | R$^2$-H | R$^3$-I | R$^4$-K | R$^5$-E | R$^6$-E | — |
| E-46 | Core-E | R$^2$-G | R$^3$-I | R$^4$-E | R$^5$-D | R$^6$-D | — |
| E-47 | Core-E | R$^2$-H | R$^3$-J | R$^4$-H | R$^5$-E | R$^6$-E | — |
| E-48 | Core-E | R$^2$-G | R$^3$-I | R$^4$-I | R$^5$-D | R$^6$-E | — |
| E-49 | Core-E | R$^2$-H | R$^3$-J | R$^4$-I | R$^5$-E | R$^6$-D | — |
| E-50 | Core-E | R$^2$-A | R$^3$-C | R$^4$-B | R$^5$-E | R$^6$-A | — |
| E-51 | Core-E | R$^2$-D | R$^3$-F | R$^4$-F | R$^5$-C | R$^6$-C | — |
| E-52 | Core-E | R$^2$-E | R$^3$-J | R$^4$-G | R$^5$-E | R$^6$-D | — |
| E-53 | Core-E | R$^2$-H | R$^3$-I | R$^4$-D | R$^5$-E | R$^6$-C | — |
| E-54 | Core-E | R$^2$-E | R$^3$-G | R$^4$-C | R$^5$-B | R$^6$-F | — |
| E-55 | Core-E | R$^2$-H | R$^3$-I | R$^4$-J | R$^5$-D | R$^6$-D | — |
| E-56 | Core-E | R$^2$-H | R$^3$-I | R$^4$-J | R$^5$-E | R$^6$-E | — |
| E-57 | Core-E | R$^2$-H | R$^3$-I | R$^4$-K | R$^5$-D | R$^6$-D | — |
| E-58 | Core-E | R$^2$-C | R$^3$-I | R$^4$-K | R$^5$-D | R$^6$-D | — |
| E-59 | Core-F | R$^2$-A | R$^3$-H | R$^4$-C | R$^5$-A | R$^6$-B | — |
| E-60 | Core-F | R$^2$-D | R$^3$-B | R$^4$-A | R$^5$-D | R$^6$-E | — |
| E-61 | Core-G | R$^2$-G | R$^3$-I | R$^4$-E | — | R$^6$-D | R$^7$-E |
| E-62 | Core-G | R$^2$-H | R$^3$-J | R$^4$-H | — | R$^6$-E | R$^7$-D |
| E-63 | Core-G | R$^2$-H | R$^3$-I | R$^4$-I | — | R$^6$-D | R$^7$-D |
| E-64 | Core-G | R$^2$-G | R$^3$-I | R$^4$-E | — | R$^6$-E | R$^7$-D |
| E-65 | Core-G | R$^2$-B | R$^3$-A | R$^4$-C | — | R$^6$-D | R$^7$-D |
| E-66 | Core-G | R$^2$-G | R$^3$-D | R$^4$-G | — | R$^6$-F | R$^7$-E |
| E-67 | Core-G | R$^2$-D | R$^3$-B | R$^4$-F | — | R$^6$-B | R$^7$-A |
| E-68 | Core-G | R$^2$-B | R$^3$-F | R$^4$-A | — | R$^6$-E | R$^7$-E |
| E-69 | Core-G | R$^2$-H | R$^3$-J | R$^4$-D | — | R$^6$-D | R$^7$-F |
| E-70 | Core-G | R$^2$-H | R$^3$-I | R$^4$-J | — | R$^6$-D | R$^7$-D |
| E-71 | Core-G | R$^2$-H | R$^3$-I | R$^4$-J | — | R$^6$-E | R$^7$-E |
| E-72 | Core-G | R$^2$-H | R$^3$-I | R$^4$-K | — | R$^6$-D | R$^7$-D |
| E-73 | Core-G | R$^2$-H | R$^3$-I | R$^4$-K | — | R$^6$-E | R$^7$-E |
| E-74 | Core-H | R$^2$-G | R$^3$-I | R$^4$-E | — | R$^6$-D | R$^7$-E |
| E-75 | Core-H | R$^2$-H | R$^3$-J | R$^4$-H | — | R$^6$-E | R$^7$-D |
| E-76 | Core-H | R$^2$-H | R$^3$-I | R$^4$-I | — | R$^6$-D | R$^7$-D |
| E-77 | Core-H | R$^2$-G | R$^3$-I | R$^4$-H | — | R$^6$-D | R$^7$-E |
| E-78 | Core-H | R$^2$-G | R$^3$-J | R$^4$-D | — | R$^6$-F | R$^7$-A |
| E-79 | Core-H | R$^2$-C | R$^3$-H | R$^4$-H | — | R$^6$-A | R$^7$-B |
| E-80 | Core-H | R$^2$-H | R$^3$-I | R$^4$-E | — | R$^6$-C | R$^7$-C |
| E-81 | Core-H | R$^2$-G | R$^3$-C | R$^4$-B | — | R$^6$-E | R$^7$-F |
| E-82 | Core-H | R$^2$-H | R$^3$-I | R$^4$-E | — | R$^6$-E | R$^7$-C |
| E-83 | Core-H | R$^2$-H | R$^3$-I | R$^4$-J | — | R$^6$-D | R$^7$-D |
| E-84 | Core-H | R$^2$-H | R$^3$-I | R$^4$-J | — | R$^6$-E | R$^7$-E |
| E-85 | Core-H | R$^2$-H | R$^3$-I | R$^4$-K | — | R$^6$-D | R$^7$-D |
| E-86 | Core-H | R$^2$-C | R$^3$-I | R$^4$-K | — | R$^6$-D | R$^7$-D |
| E-87 | Core-I | R$^2$-C | R$^3$-E | R$^4$-D | — | R$^6$-C | R$^7$-A |
| E-88 | Core-I | R$^2$-D | R$^3$-G | R$^4$-A | — | R$^6$-B | R$^7$-F |

Examples of most preferred compounds according to this invention are each single compound listed in the following Tables 1 to 4.

In general, all tautomeric and isomeric forms and mixtures thereof, for example, individual tautomers, geometric isomers, stereoisomers, atropoisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer.

Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000, herein incorporated by reference. Furthermore, there are equally well-known methods for the quantitation of enantiomeric excess or purity, for example, GC, HPLC, CE, or NMR, and assignment of absolute configuration and conformation, for example, CD, ORD, X-ray crystallography, or NMR.

Pharmaceutical Composition

Compounds of the present invention may be administered to a mammal in need of treatment for HIV infection as a pharmaceutical composition comprising a therapeutically effective amount of a compound according to the invention or a pharmaceutically acceptable salt or ester thereof; and one or more conventional non-toxic pharmaceutically-acceptable carriers, adjuvants or vehicles. The specific formulation of the composition is determined by the solubility and chemical nature of the compound, the chosen route of administration and standard pharmaceutical practice. The pharmaceutical composition according to the present invention may be administered orally or systemically.

When one enantiomer of a chiral active ingredient has a different biological activity than the other, it is contemplated that the pharmaceutical composition according to the invention may comprise a racemic mixture of the active ingredient, a mixture enriched in one enantiomer of the active ingredient or a pure enantiomer of the active ingredient. The mixture enriched in one enantiomer of the active ingredient is contemplated to contain from more than 50% to about 100% of one enantiomer of the active ingredient and from about 0% to less than 50% of the other enantiomer of the active ingredient. Preferably, when the composition comprises a mixture enriched in one enantiomer of the active ingredient or a pure enantiomer of the active ingredient, the composition comprises from more than 50% to about 100% of, or only, the more physiologically active enantiomer and/or the less toxic enantiomer. It is well known that one enantiomer of an active ingredient may be the more physiologically active for one therapeutic indication while the other enantiomer of the active ingredient may be the more physiologically active for a different therapeutic indication; therefore the preferred enantiomeric makeup of the pharmaceutical composition may differ for use of the composition in treating different therapeutic indications.

For oral administration, the compound, or a pharmaceutically acceptable salt or ester thereof, can be formulated in any orally acceptable dosage form including but not limited to aqueous suspensions and solutions, capsules, powders, syrups, elixirs or tablets. For systemic administration, including but not limited to administration by subcutaneous, intracutaneous, intravenous, intramuscular, intra-articular, intrasynovial, intrasternal, intrathecal, and intralesional injection or infusion techniques, it is preferred to use a solution of the compound, or a pharmaceutically acceptable salt or ester thereof, in a pharmaceutically acceptable sterile aqueous vehicle.

Pharmaceutically acceptable carriers, adjuvants, diluents, vehicles, excipients and additives as well as methods of formulating pharmaceutical compositions for various modes of administration are well-known to those of skill in the art and are described in pharmaceutical texts such as Remington: The Science and Practice of Pharmacy, 21st Edition, Lippincott Williams & Wilkins, 2005; and L. V. Allen, N. G. Popovish and H. C. Ansel, Pharmaceutical Dosage Forms and Drug Delivery Systems, 8th ed., Lippincott Williams & Wilkins, 2004, herein incorporated by reference.

The dosage administered will vary depending upon known factors, including but not limited to the activity and pharmacodynamic characteristics of the specific compound employed and its mode, time and route of administration; the age, diet, gender, body weight and general health status of the recipient; the nature and extent of the symptoms; the severity and course of the infection; the kind of concurrent treatment; the frequency of treatment; the effect desired; and the judgment of the treating physician. In general, the compound is most desirably administered at a dosage level that will generally afford antivirally effective results without causing any harmful or deleterious side effects.

A daily dosage of active ingredient can be expected to be about 0.001 to about 100 milligrams per kilogram of body weight, with the preferred dose being about 0.01 to about 50 mg/kg. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Therefore, according to one embodiment, the pharmaceutical composition according to the invention comprises a racemic mixture of the compound of formula (I), or a pharmaceutically acceptable salt or ester thereof.

An alternative embodiment provides a pharmaceutical composition comprising a mixture enriched in one enantiomer of the compound of formula (I), or a pharmaceutically acceptable salt or ester thereof.

A further embodiment provides a pharmaceutical composition comprising a pure enantiomer of the compound of formula (I), or a pharmaceutically acceptable salt or ester thereof.

Combination Therapy

Combination therapy is contemplated wherein a compound according to the invention, or a pharmaceutically acceptable salt or ester thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt or ester thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from:

NRTIs (nucleoside or nucleotide reverse transcriptase inhibitors) including but not limited to zidovudine (AZT), didanosine (ddI), zalcitabine (ddC), stavudine (d4T), lamivudine (3TC), emtricitabine, abacavir succinate, elvucitabine, adefovir dipivoxil, lobucavir (BMS-180194) lodenosine (FddA) and tenofovir including tenofovir disoproxil and tenofovir disoproxil fumarate salt, COMBIVIR™ (contains 3TC and AZT), TRIZIVIR™ (contains abacavir, 3TC and AZT), TRUVADA™ (contains tenofovir and emtricitabine), EPZICOM™ (contains abacavir and 3TC);

NNRTIs (non-nucleoside reverse transcriptase inhibitors) including but not limited to nevirapine, delaviradine, efavirenz, etravirine and rilpivirine;

protease inhibitors including but not limited to ritonavir, tipranavir, saquinavir, nelfinavir, indinavir, amprenavir, fosamprenavir, atazanavir, lopinavir, darunavir (TMC-114), lasinavir and brecanavir (VX-385);

entry inhibitors including but not limited to
  CCR5 antagonists (including but not limited to maraviroc, vicriviroc, INCB9471 and TAK-652),
  CXCR4 antagonists (including but not limited to AMD-11070),
  fusion inhibitors (including but not limited to enfuvirtide (T-20), TR1-1144 and TR1-999) and
  others (including but not limited to BMS-488043);

integrase inhibitors (including but not limited to raltegravir (MK-0518), BMS-707035 and elvitegravir (GS 9137));

TAT inhibitors;

maturation inhibitors (including but not limited to berivimat (PA-457));

immunomodulating agents (including but not limited to levamisole); and other antiviral agents including hydroxyurea, ribavirin, IL-2, IL-12 and pensafuside.

Furthermore, a compound according to the invention can be used with at least one other compound according to the invention or with one or more antifungal or antibacterial agents (including but not limited to fluconazole).

Therefore, according to one embodiment, the pharmaceutical composition of this invention additionally comprises one or more antiviral agents.

A further embodiment provides the pharmaceutical composition of this invention wherein the one or more antiviral agent comprises at least one NNRTI.

According to another embodiment of the pharmaceutical composition of this invention, the one or more antiviral agent comprises at least one NRTI.

According to yet another embodiment of the pharmaceutical composition of this invention, the one or more antiviral agent comprises at least one protease inhibitor.

According to still another embodiment of the pharmaceutical composition of this invention, the one or more antiviral agent comprises at least one entry inhibitor.

According to a further embodiment of the pharmaceutical composition of this invention, the one or more antiviral agent comprises at least one integrase inhibitor.

A compound according to the present invention may also be used as a laboratory reagent or a research reagent. For example, a compound of the present invention may be used as positive control to validate assays, including but not limited to surrogate cell-based assays and in vitro or in vivo viral replication assays.

Furthermore, a compound according to the present invention may be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

Derivatives Comprising a Detectable Label

Another aspect of the invention provides a derivative of a compound of formula (I), the derivative comprising a detectable label. Such a label allows recognition either directly or indirectly of the derivative such that it can be detected, measured or quantified. The detectable label may itself be detectable, measurable or quantifiable, or it may interact with one or more other moieties which themselves comprise one or more detectable labels, so that the interaction therebetween allows the derivative to be detected, measured or quantified.

Such derivatives may be used as probes to study HIV replication, including but not limited to study of the mechanism of action of viral and host proteins involved in HIV replication, study of conformational changes undergone by such viral and host proteins under various conditions and study of interactions with entities which bind to or otherwise interact with these viral and host proteins. Derivatives according to this aspect of the invention may be used in assays to identify compounds which interact with viral and host proteins, the assays including but not limited to displacement assays which measure the extent to which the derivative is displaced from interacting with the viral and host proteins. A preferred use of derivatives according to this aspect of the invention is in displacement assays to identify HIV integrase inhibitors. Such derivatives may also be used to form covalent or non-covalent interactions with the viral and host proteins or to identify residues of the viral and host proteins which interact with the compounds of the invention.

Detectable labels contemplated for use with derivatives of the compounds of the invention include, but are not limited to, fluorescent labels, chemiluminescent labels, chromophores, antibodies, enzymatic markers, radioactive isotopes, affinity tags and photoreactive groups.

A fluorescent label is a label which fluoresces, emitting light of one wavelength upon absorption of light of a different wavelength. Fluorescent labels include but are not limited to fluorescein; Texas Red; aminomethylcoumarin; rhodamine dyes, including but not limited to tetramethylrhodamine (TAMRA); Alexa dyes including but not limited to Alexa Fluor® 555; cyanine dyes including but not limited to Cy3; europium or lanthanide series based fluorescent molecules; and the like.

A chemiluminescent label is a label which can undergo a chemical reaction which produces light. Chemiluminescent labels include but are not limited to luminol, luciferin, lucigenin, and the like.

A chromophore is a label which selectively absorbs certain wavelengths of visible light while transmitting or reflecting others, thereby causing the compounds which contain the chromophore to appear colored. Chromophores include but are not limited to natural and synthetic dyes.

An antibody is a protein produced by a mammalian immune system in response to a specific antigen, which binds specifically to that antigen. Antibodies contemplated for use as detectable labels according to the invention include but are not limited to antibodies against the following: polyhistidine tags, glutathione-S-transferase (GST), hemagglutinin (HA), FLAG® epitope tags, Myc tag, maltose binding protein (MBP), green fluorescent protein (GFP) and the like.

An enzymatic marker is an enzyme whose presence may be detected by means of an assay specific to the catalytic activity of the enzyme. Enzymatic markers contemplated for use as detectable labels according to the invention include but are not limited to luciferase, horseradish peroxidase (HRP), β-galactosidase and the like.

A radioactive isotope is an isotope of an atom which produces radiation upon radioactive decay. Radioactive isotopes include but are not limited to $^{14}C$, $^{3}H$, $^{31}P$ $^{121}I$, $^{125}I$ and the like.

An affinity tag is a label which has a strong affinity for another moiety, designated herein as a binding partner. Such an affinity tag can be used to form a complex with the binding partner so that the complex may be selectively detected or separated from a mixture. Affinity tags include but are not limited to biotin or a derivative thereof, a histidine polypeptide, a polyarginine, an amylose sugar moiety or a defined epitope recognizable by a specific antibody; suitable epitopes include but are not limited to glutathione-S-transferase (GST), hemagglutinin (HA), FLAG® epitope tags, Myc tag, maltose binding protein (MBP), green fluorescent protein (GFP) and the like.

Furthermore, compounds of the invention used as probes may be labelled with a photoreactive group which is transformed, upon activation by light, from an inert group to a reactive species, such as a free radical. Such a group may be used to activate the derivative so that it can form a covalent bond with one or more residues of a viral or host protein. Photoreactive groups include but are not limited to photoaffinity labels such as benzophenone and azide groups.

Methodology and Synthesis

The synthesis of compounds of formula (I) according to this invention is conveniently accomplished following the general procedure outlined in the schemes below wherein c, X, Y, $R^2$, $R^3$, $R^4$, $R^5$, $R^6$ and $R^7$ are as defined herein. Further instruction is provided to one skilled in the art by the specific examples set out herein below.

Scheme 1: Assembly of inhibitors

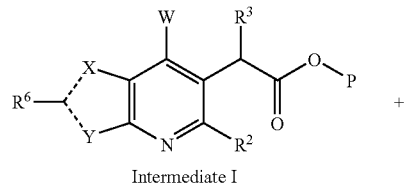

Intermediate I

+

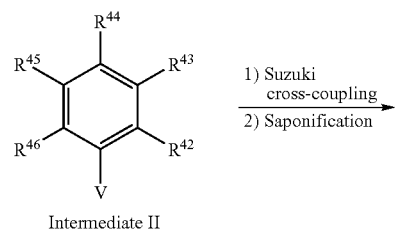

Intermediate II

-continued

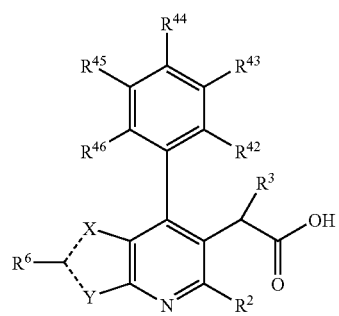

wherein $R^{42}$, $R^{43}$, $R^{44}$, $R^{45}$ and $R^{46}$ may either be substituents on the phenyl moiety or ($R^{42}$ and $R^{43}$), ($R^{43}$ and $R^{44}$), ($R^{44}$ and $R^{45}$) or ($R^{45}$ and $R^{46}$) may be linked so to as to form a carbocycle or heterocycle, W is iodo, bromo, chloro or OTf, V is $B(OH)_2$ or boronate esters such as $B(OCH_3)_2$ and $B(OC(CH_3)_2C(CH_3)_2O)$, iodo, $SnR_3$ wherein R is $(C_{1-6})$alkyl, ZnX wherein X is halo, and P is a protecting group, such as commonly used protecting groups for carboxylic acids, including, but not limited to a methyl or ethyl ester.

Several coupling methods between the intermediate (I) (i.e. thienopyridine scaffold) and the intermediate II (i.e. $R^4$ substituent) can be contemplated by those skilled in the art. For examples, but not limited to, Suzuki cross-coupling between the boronic acid or boronate ester derivative of intermediate II and the halo or triflate derivative of intermediate I, copper catalyzed Ullmann cross-coupling between the iodo derivatives of intermediates I and II, Negishi cross-coupling between the arylzinc reagent of the intermediate II and the iodo or triflate derivative of intermediate I, and Stille coupling between the arylltin reagent of intermediate II and the bromo or iodo derivative of intermediate I as shown above can lead, after saponification, to the compounds of the invention of formula (I).

Alternatively, the same cross-coupling methods can be used by interchanging the coupling partners as shown below. For examples, Suzuki, Negishi, and Stille type cross-coupling between boronic acid or boronate ester derivative, the arylzinc reagent or the arylltin reagent of thienopyridine intermediate III and the required iodo, bromo, chloro or triflate derivative of intermediate IV can also lead, after saponification, to the compounds of formula (I).

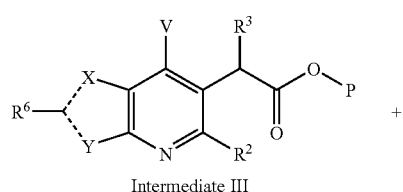

Intermediate III

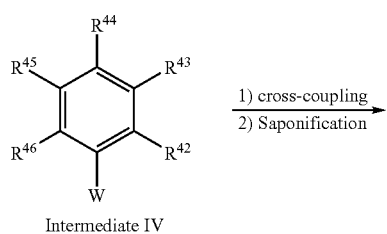

Intermediate IV 1) cross-coupling
2) Saponification →

-continued

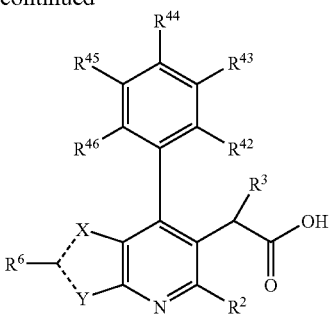

wherein $R^{42}$, $R^{43}$, $R^{44}$, $R^{45}$ and, $R^{46}$ and P are as defined above and W is iodo, bromo, chloro or OTf, V is $B(OH)_2$ or boronate esters such as $B(OCH_3)_2$ and $B(OC(CH_3)_2C(CH_3)_2O)$, $SnR_3$ wherein R is $(C_{1-6})$alkyl, and ZnX wherein X is halo.

Furthermore, downstream modifications to the product can be contemplated, such as conversion of an aniline-type amine to a chloro or bromo substituent via Sandmeyer reaction or alkylation, or dehalogenation via reduction.

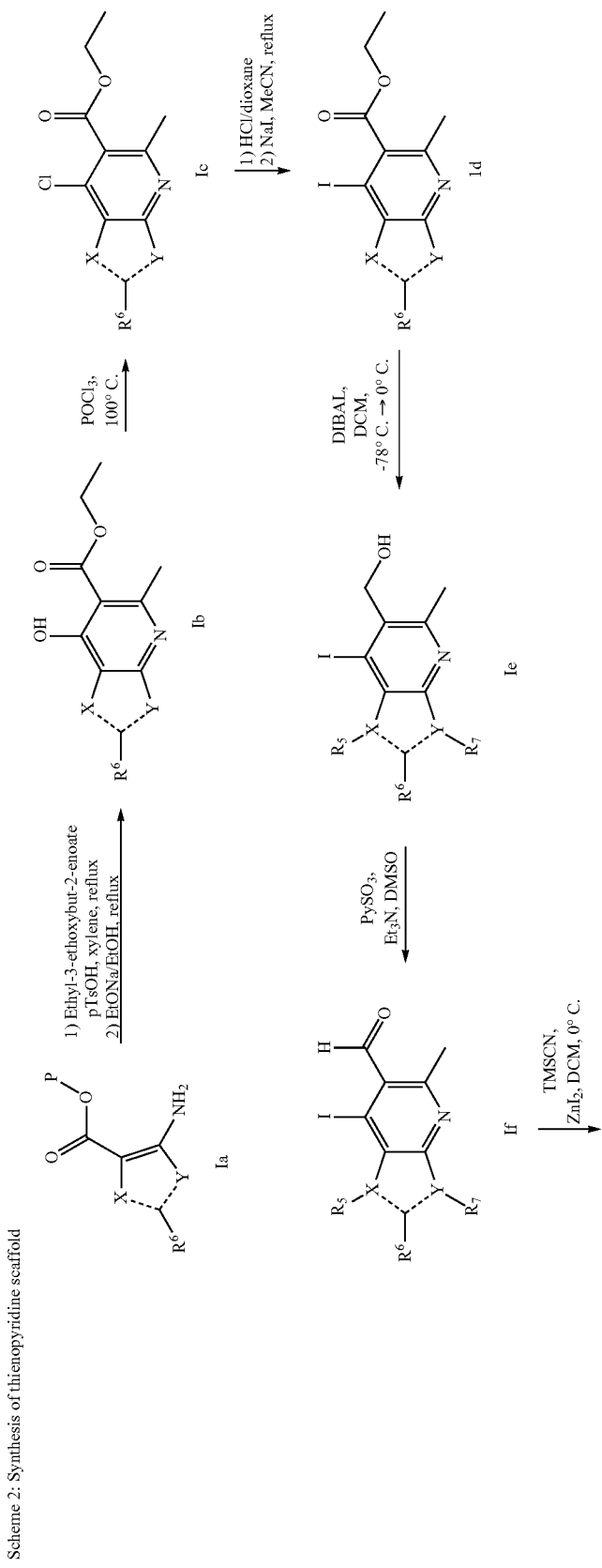
Scheme 2: Synthesis of thienopyridine scaffold

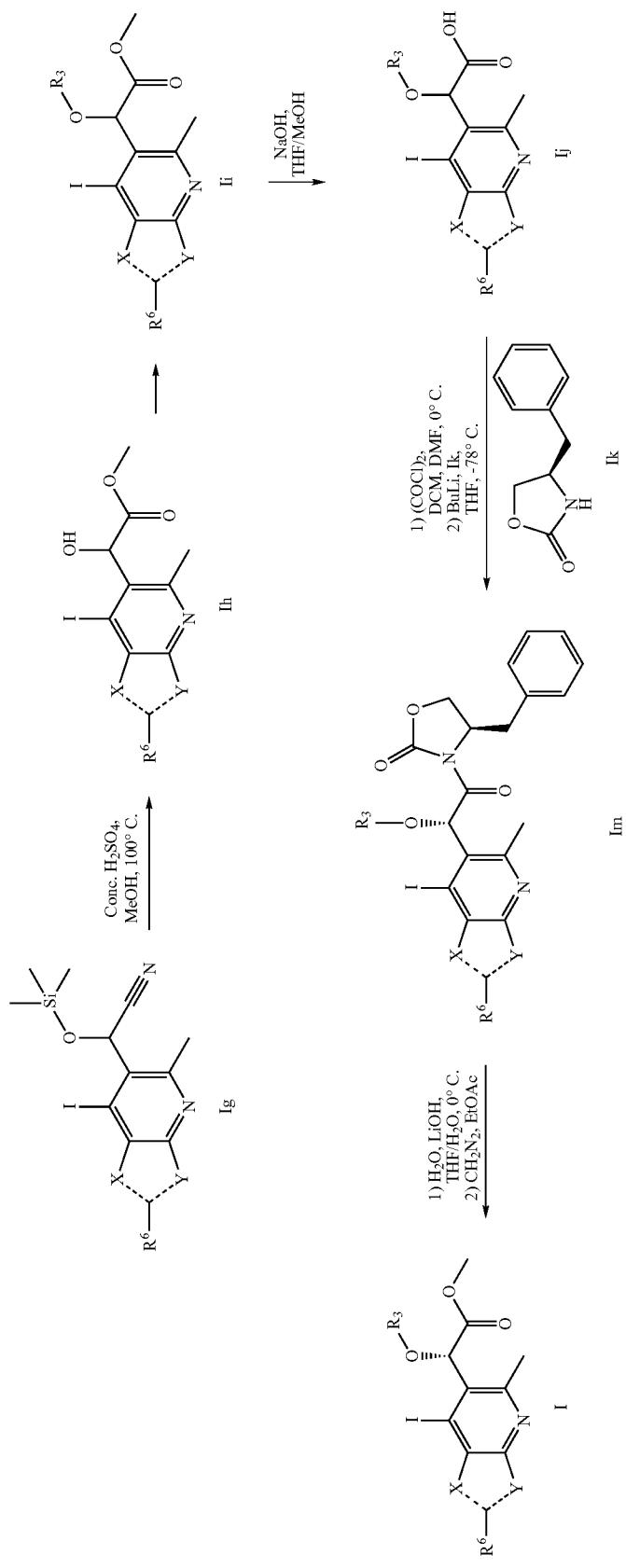

In an alternative route to compounds of general formula I, a thiophene that is 1,2-disubstituted with an amino group and a protected carboxylate, exemplified by compound Ia, is condensed with ethyl-3-ethoxybut-2-enoate to give an imine that then undergoes ring annulation to give thienopyridine Ib. It will be obvious to those skilled in the art that a very large number of possible reaction conditions can be used to effect this condensation-annulation process. The phenol moiety is then exchanged for a chloro group by treatment with $POCl_3$ and the chloro is subsequently exchanged for an iodo group under acidic conditions in the presence of NaI to give aryl iodide Id. Those skilled in the art will recognize that the phenol functionality can be transformed to a number of different functionalities including, but not limited to, Cl, Br, I and OTf, to allow access to intermediate II. The ester group of Id is then reduced to the corresponding benzyl alcohol Ie, preferably, but not limited to, by treatment with DIBAL. Those skilled in the art will recognize that this routine transformation can be performed under a large number of reaction conditions. Oxidation of alcohol Ie to aldehyde If, followed by addition of TMSCN provides cyanohydrin derivative Ig. It will be obvious that both the oxidation of Ie to If and transformation of the aldehyde to Ig can be accomplished by a number of different, well precedented synthetic steps. In the preferred embodiment, oxidation by treatment with $SO_3$-pyridine complex in the presence of DMSO, followed by zinc iodide mediated addition of TMSCN provides Ig from Ie.

Acid catalyzed methanolysis of Ig provides ester Ih. The secondary alcohol is then derivatized with the $R^3$ group to give compound Ii. Those skilled in the art will recognize that this can be accomplished in a very large number of ways, including those used to construct ether bonds such as, but not limited to, $SN_1$ or $SN_2$ reactions or acid catalyzed addition to an alkene. Saponification of the methyl ester gives acid Ij, which is then derivatized with an enantiopure chiral auxiliary, such as Ik, to give a mixture of diastereomers that can be separated to provide Im. Those skilled in the art will recognize that many different chiral auxiliaries are available for conversion of racemic acid Ij to a mixture of diastereomers and it will be obvious that this is a well precedented method for the chemical resolution of stereoisomers. In the preferred embodiment, acid Ij is activated by conversion to its corresponding acid chloride, which is then converted in situ to imide Im. It will also be obvious that this particular transformation may be accomplished by a variety of known methods, including, but not limited to, sequential versions of the same process and activation of acid Ij by other means known to those skilled in the art. Imide Im, once separated from its diastereomer, is then hydrolyzed and the resulting carboxylate converted to ester I, in the preferred embodiment by a standard two step process.

Alternatively, a modification of this approach can also be used to prepare the thienopyridine scaffold as outlined in Scheme 3.

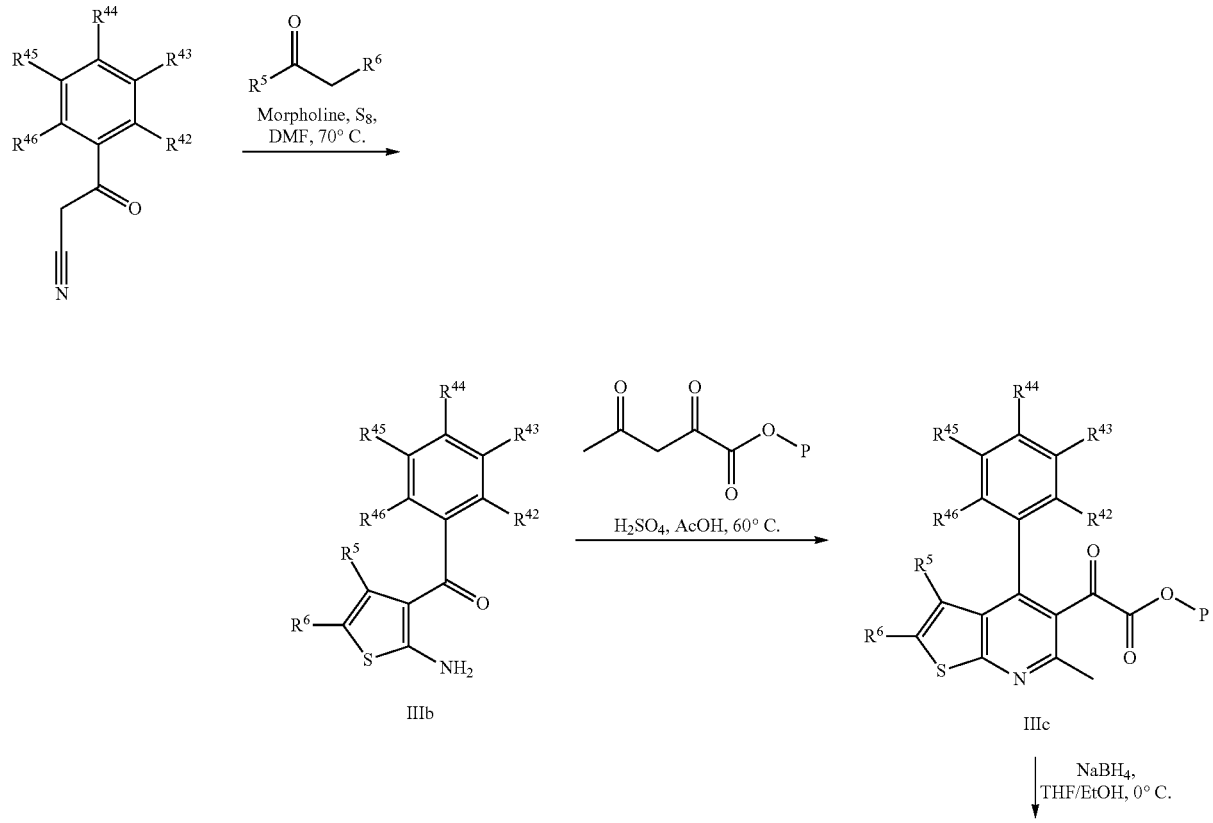

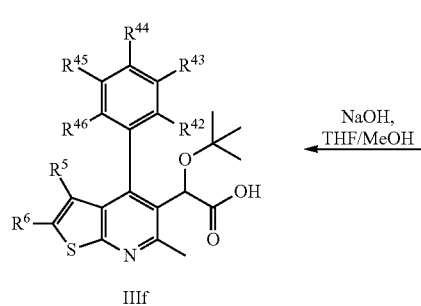 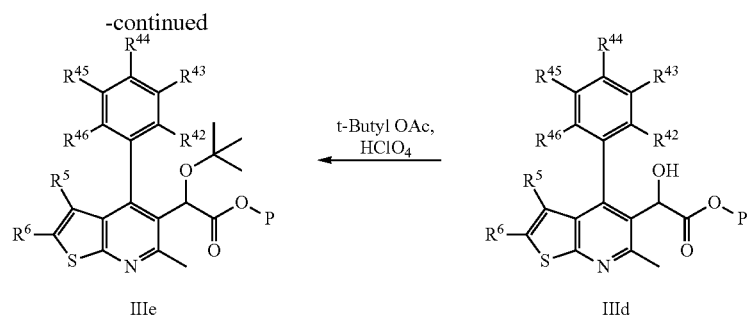

In this method a properly substituted benzoylacetonitrile can be condensed in the presence of sulfur with an appropriate ketone or aldehyde by standard methods known in the literature. Condensation of intermediates IIIb with an appropriate α,γ-diketoester reagent, by procedures known to the skilled in the art or as set forth in the examples below, provides intermediates of formula IIIc wherein P is an ester protecting group such as methyl or ethyl. Reduction of intermediates IIIc, by procedures known to the skilled in the art or as set forth in the examples below, provides intermediates of formula IIId. As is well known to a person skilled in the art, such reduction can be achieved in an enantioselective fashion using procedure known in the literature. The secondary alcohol is then derivatized to the tert-butyl ether using tert-butyl acetate. Those skilled in the art will recognize that this can be accomplished in more than one way, including an $SN_1$ reaction or acid catalyzed addition to isobutylene. Hydrolysis of the ester protecting group of intermediates IIIe, by procedures known to the skilled in the art or as set forth in the examples below, provides compounds of formula IIIf. Furthermore, the thienopyridine scaffold can be accessed in an enantioselective manner as outlined in Scheme 2.

Scheme 4: Alternate synthesis of thienopyridine scaffold

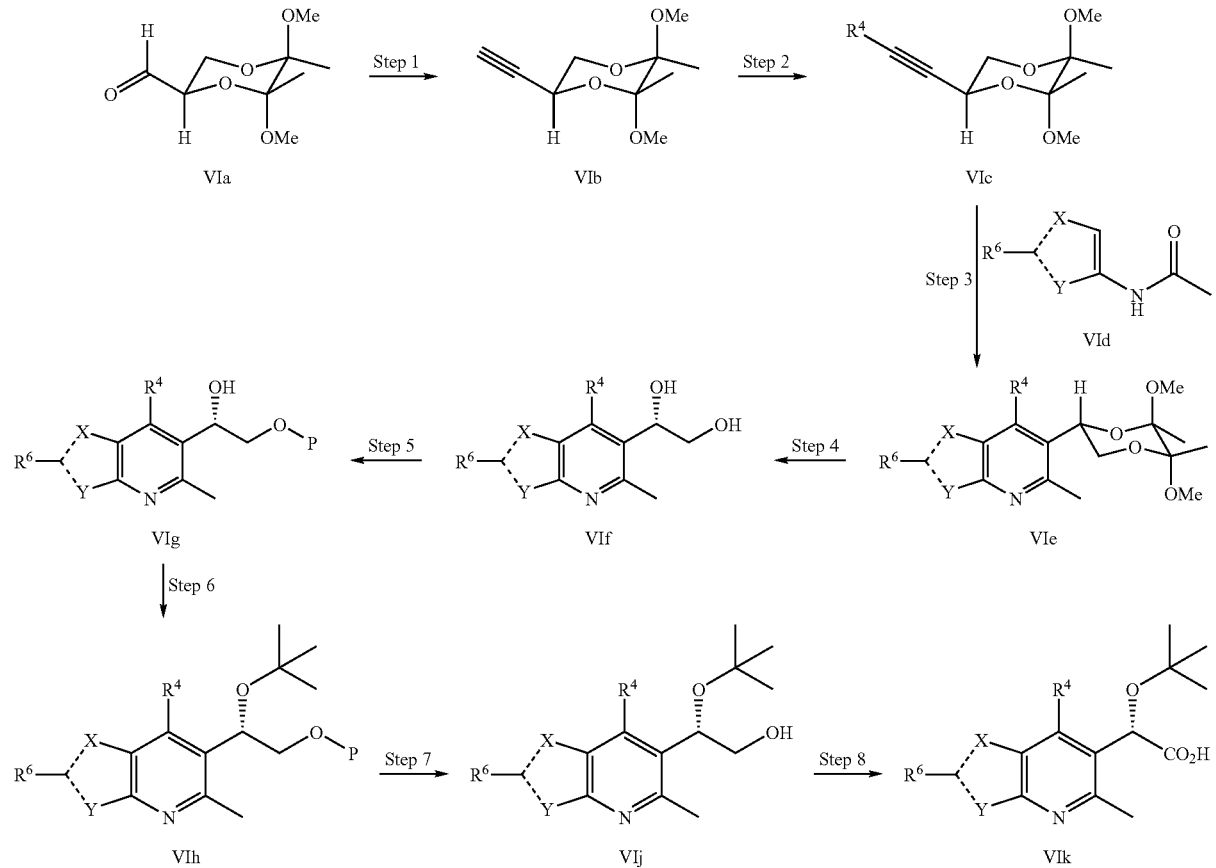

In an alternate route to compounds of general formula I, the known aldehyde VIa is transformed to terminal alkyne VIb. Those skilled in the art will recognize that there are a number of methods for accomplishing this transformation, such as, but not limited to the Bestmann-Ohira reaction or the Corey- Fuchs reaction. The $R^4$ group is then attached to the alkyne using conditions well-known to those skilled in the art, preferentially via a Sonogashira coupling between the alkyne and the aryl iodide derivative of the $R^4$ group, to give the internal alkyne VIc. Other methods may include the Castro-Stevens reaction, or the silver mediated, palladium catalyzed coupling of alkyne VIb and the boronic acid or ester derivative of the $R^4$ fragment as reported by Zou and coworkers (*Tetrahedron Lett.* 2003, 44, 8709-8711). The internal alkyne VIc then undergoes a cyclocondensation with amide VId to give thienopyridine VIe. Those skilled in the art will recognize this may involve activation of amide VId to facilitate the overall condensation. This is preferentially achieved by the action of triflic anhydride and in the presence of 2-chloropyridine as described by Movassaghi (*J. Am. Chem. Soc.*, 129 (33), 10096-10097), but may also be achieved in other ways. Amides VId are typically commercially available, although those skilled in the art will recognize that they are also easily obtained from commercially available aniline or nitro arene precursors. The cyclic diketal is then hydrolyzed to give diol VIf under acidic conditions. The terminal alcohol is then protected to give VIg, where P can be a number of different protecting groups including, but not limited to, a trimethylacetyl group. The secondary alcohol is then derivatized with a tert-butyl group to give compound VIh. Those skilled in the art will recognize that this can be accomplished in more than one way, including an $SN_1$ reaction or acid catalyzed addition to isobutylene. The protecting group is then removed to give primary alcohol VIj, which in turn is oxidized to carboxylic acid VIk. It will be obvious that the oxidation of VIj to VIk can be accomplished in one or two synthetic steps. In the preferred method, Dess-Martin oxidation to an intermediate aldehyde followed by Lindgren oxidation is employed.

limited to, a trimethylacetyl group. The secondary alcohol is then derviatized with the tert-butyl group to give compound VIIc. Those skilled in the art will recognize that this can be accomplished in more than one way, including an $SN_1$ reaction or acid catalyzed addition to isobutylene. The $R^4$ group is then attached to the alkyne using conditions well-known to those skilled in the art, preferentially via a Sonogashira coupling between the alkyne and the aryl iodide derivative of the $R^4$ group, to give the internal alkyne VIId. The internal alkyne VIId then undergoes a cyclocondensation with amide VId to give quinoline VIh, preferentially achieved by the action of triflic anhydride and in the presence of 2-chloropyridine as described for step 3 of Scheme 4. From intermediate VIh, the synthesis compounds of the invention of general formula (I) is then accomplished following steps 7 and 8 of Scheme 4.

EXAMPLES

Other features of the present invention will become apparent from the following non-limiting examples which illustrate, by way of example, the principles of the invention. It will be apparent to a skilled person that the procedures exemplified below may be used, with appropriate modifications, to prepare other compounds of the invention as described herein.

As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem.,

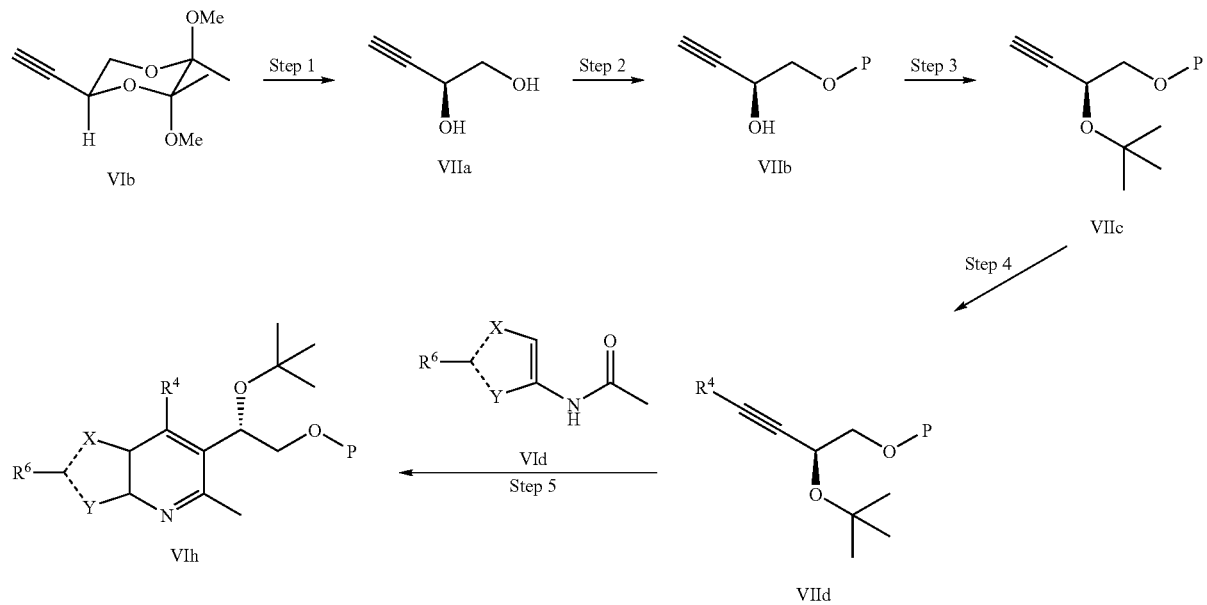

Scheme 5: Alternate synthesis of thienopyridine scaffold

In yet another route to compounds of general formula I, synthesis of intermediate VIh may also be accomplished following a path that begins with acid catalyzed hydrolysis of the cyclic diketal of terminal alkyne VIb to give diol VIIa. The terminal alcohol is then protected to give VIIb, where P can be a number of different protecting groups including, but not (1978), 43, 2923. Mass spectral analyses are recorded using electrospray mass spectrometry. A number of intermediate and final products are purified using CombiFlash® Companion apparatus, purchased from Teledyne Isco Inc, employing pre-packed silica gel cartridges and EtOAc and hexane as solvents. These cartridges are available either from Silicycle Inc (SiliaFlash, 40-63 microns silica) or from Teledyne Isco (RediSep, 40-63 microns silica). Preparative HPLC is carried out under standard conditions using a SunFire™ Prep C18 OBD 5 μM reverse phase column, 19×50 mm and a linear gradient employing 0.1% TFA/acetonitrile and 0.1% TFA/water as solvents. Compounds are isolated as TFA salts when applicable. Analytical HPLC is carried out under standard conditions using a Combiscreen ODS-AQ C18 reverse phase column, YMC, 50×4.6 mm i.d., 5 μM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:

| | |
|---|---|
| Ac: | acetyl; |
| AcOH: | acetic acid; |
| $Ac_2O$: | acetic anhydride; |
| BOC or Boc: | tert-butyloxycarbonyl; |
| Bu: | butyl; |
| CD: | circular dichroism; |
| DABCO: | 1,4-diazabicyclo[2.2.2]octane |
| DBU: | 1,8-diazabicyclo[5.4.0]undec-7-ene; |
| DCE: | dichloroethane; |
| DCM: | dichloromethane; |
| DEAD: | diethyl azodicarboxylate; |
| DIAD: | diisopropyl azodicarboxylate; |
| DIBAL: | diisobutyl aluminum hydride; |
| DMAP: | N,N-dimethyl-4-aminopyridine; |
| DME: | 1,2-dimethoxyethane; |
| DMF: | N,N-dimethylformamide; |
| DMSO: | dimethylsulfoxide; |
| Dppf: | 1,1'-Bis(diphenylphosphino)ferrocene; |
| $EC_{50}$: | 50% effective concentration; |
| Eq: | equivalent; |
| Et: | ethyl; |
| $Et_3N$: | triethylamine; |
| $Et_2O$: | diethyl ether; |
| EtOAc: | ethyl acetate; |
| EtOH: | ethanol; |
| HPLC: | high performance liquid chromatography; |
| $IC_{50}$: | 50% inhibitory concentration; |
| $^iPr$ or i-Pr: | 1-methylethyl (iso-propyl); |
| LiHMDS: | lithium hexamethyldisilazide; |
| Me: | methyl; |
| MeCN: | acetonitrile; |
| MeOH: | methanol; |
| MOI: | multiplicity of infection; |
| MS: | mass spectrometry (ES: electrospray); |
| n-BuONa: | sodium n-butoxide |
| n-BuOH: | n-butanol; |
| n-BuLi: | n-butyllithium; |
| NMR: | nuclear magnetic resonance spectroscopy; |
| ORD: | optical rotary dispersion; |
| Ph: | phenyl; |
| PhMe: | toluene; |
| PG: | protecting group; |
| Pr: | propyl; |
| RPMI: | Roswell Park Memorial Institute (cell culture medium); |
| RT: | room temperature (approximately 18° C. to 25° C.); |
| SM: | starting material; |
| tert-butyl or t-butyl: | 1,1-dimethylethyl; |
| Tf: | trifluoromethanesulfonyl; |
| $Tf_2O$: | trifluoromethanesulfonic anhydride; |
| TFA: | trifluoroacetic acid; |
| THF: | tetrahydrofuran; |
| TLC: | thin layer chromatography; |
| TsOH: | p-toluenesulfonic acid; and |
| TMSCN: | trimethylsilyl cyanide. |

Example 1

Synthesis of Thienopyridine Scaffold IA

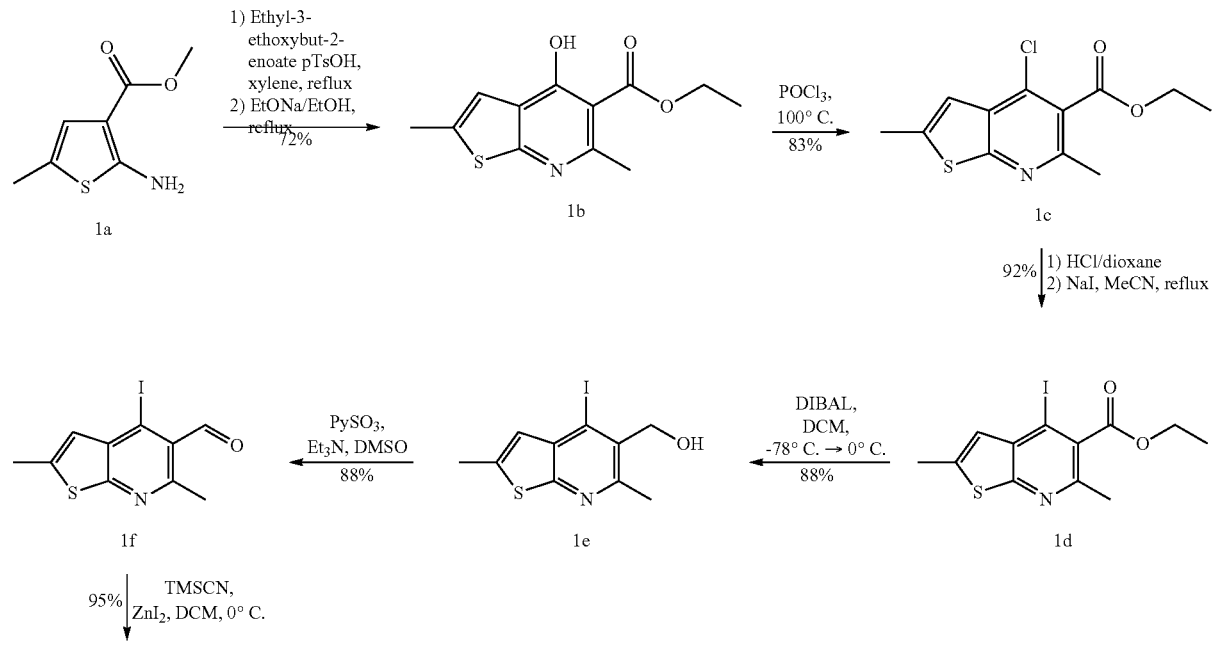

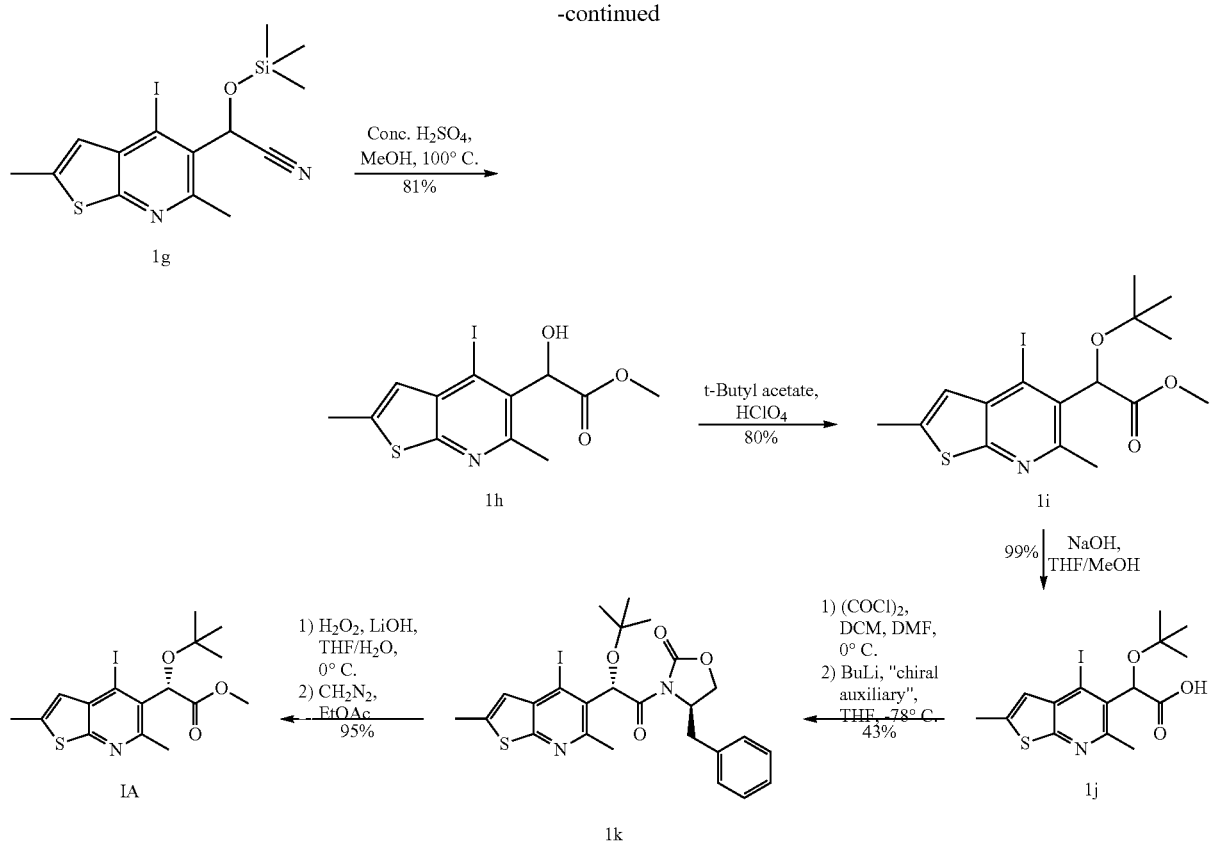

Step 1:
Thiophene 1a (11.2 g, 65.3 mmol) is dissolved in dry xylene (250 mL) before being treated with ethyl-3-ethoxy-but-2-enoate (10.84 g, 68.5 mmol) and catalytic TsOH (30 mg, 0.16 mmol). The resulting solution is heated at reflux (bath temp: 158° C.) equipped with a Dean-Stark column and condensor to collect ethanol. After 5 h, the solution is cooled (cold water bath), transferred to a dropping funnel and then added dropwise (over about 15 min) to a stirred solution of sodium ethoxide in ethanol (25.6 mL of a 21% wt solution NaOEt in ethanol (68.5 mmol diluted into 150 mL of absolute ethanol). The resulting solution is heated to reflux under a nitrogen atmosphere. After 16 h, the reaction is cooled and the ethanol and xylene removed under reduced pressure to yield an ochre semisolid. This material is dissolved/suspended in water (500 mL) and washed with ethyl ether (2×500 mL). The aqueous phase is separated, cooled to 0° C. and slowly acidified to pH ~4 with 1 N HCl (65 mL) with rapid stirring. The resulting precipitate is filtered, washed with dilute HCl (pH 4, 50 mL) and air dried to afford an orange powder 1b (11.85 g, 72% yield) which is used as such in the following step.

Step 2:
The thienopyridine 1b (11.85 g, 47.15 mmol) is suspended in POCl₃ (100 mL) and the mixture heated to 100° C. for 20 min before being concentrated under vacuum. The residue is diluted with EtOAc, washed with aqueous saturated NaHCO₃, water, and brine before being dried (MgSO₄), filtered and concentrated under vacuum. The crude product is purified by flash chromatography using Hexanes/EtOAc 8/2 to give the 4-chloro analog 1c as a yellow oil (10.50 g, 82.5% yield).

Step 3:
To a solution of the 4-chloro analog 1c (10.5 g, 38.9 mmol) in THF (100 mL) at RT is slowly added 4 M HCl in dioxane (97 mL, 389 mmol). The resulting mixture is stirred at RT for 10 min before the solvents are evaporated. The precipitate is suspended in CH₃CN (300 mL) and treated with NaI (46.7 g, 311 mmol). The resulting mixture is heated at reflux for 16 h. The mixture is then concentrated before being dissolved in EtOAc (300 mL) and then washed with 1.0 N NaOH (100 mL), water (2×), 10% Na₂S₂O₃ (2×), water and saturated brine. The organic phase is dried (MgSO₄), filtered and concentrated under vacuum to give a yellow solid 1d (12.88 g, 91.6% yield).

Step 4:
To a solution of the 4-iodo intermediate 1d (12.88 g, 35.66 mmol) in DCM (100 ml) at −78° C. is added dropwise over 5 min the DIBAL/DCM solution (1M in DCM, 82 mL, 82 mmol). The resulting solution is stirred for 1.5 h and then at 0° C. for 30 min. The reaction is quenched with 100 ml of 1 N HCl by slow addition and the resulting mixture stirred for 1 h. The mixture is extracted with DCM and the combined organic extracts are washed with Rochelle's solution, water, and brine before being dried (MgSO₄). The organic phase is filtered and concentrated under vacuum to give a pale beige solid 1e (10 g, 88% yield).

Step 5:
To a cold (15° C.) solution of alcohol 1e (10.05 g, 31.5 mmol) in DMSO (50 mL) was added Et₃N (13.2 ml, 94.5 mmol) followed by Py.SO₃ complex (12.5 g, 78.7 mmol). The reaction mixture was stirred at RT for 1 h and then poured into water (200 mL). The mixture was filtered and dried under vacuum to afford compound 1f (8.8 g, 88% yield) as an off white solid.

Step 6:

To a cold (0° C.) mixture of aldehyde 1f (8.8 g, 27.8 mmol) in DCM (150 mL) is added $ZnI_2$ (4.43 g, 13.9 mmol, 0.5 eq) followed by TMSCN (11.1 mL, 83.3 mmol). The reaction mixture is stirred at RT for 1 h, diluted with DCM (150 mL) and quenched with water (200 mL). The aqueous phase is extracted with DCM and the combined organic extracts are washed with water and brine before being dried ($MgSO_4$) and filtered. Concentration of the extract under vacuum gives compound 1g as an off-white solid (11.02 g, 95% yield).

Step 7:

Concentrated $H_2SO_4$ (20 mL, 375 mmol) is carefully added to cold (0° C.) MeOH (104 mL) and the resulting warm solution is then added to the TMS protected cyanohydrin 1g (5.52 g, 13.7 mmol). The reaction mixture is stirred at 100° C. for 5 h, cooled to 0° C., diluted with water (200 mL) and neutralized using solid NaOH. The resulting precipitate is filtered and dried under vacuum overnight to give compound 1h as an off-white solid (7.97 g, 85% yield).

Step 8:

To a mixture of the alpha hydroxyester 1h (7.97 g, 21.1 mmol) in tert-butyl acetate (100 mL) at RT is added perchloric acid (70%, 3.33 mL, 23.2 mmol). The resulting solution is stirred at RT for 4 h. A saturated solution of $NaHCO_3$ was added until pH ~8 is reached and the solution then extracted with DCM (3×), dried over $MgSO_4$, filtered and concentrated under vacuum. The residue is purified by flash chromatography using Hexanes/EtOAc 8/2 to afford compound 1i (7.34 g, 80% yield) as a white solid.

Step 9:

To a solution of the t-butyl ether 1i (5.34 g, 12.3 mmol) in THF (150 mL) and MeOH (75 mL) at RT is added 5 N NaOH (12.3 mL, 61.6 mmol) and the reaction mixture is stirred overnight. The mixture is then treated with 1.0 N HCl (aqueous) (to make it slightly acidic) and the mixture is extracted with DCM. The combined extracts are washed with water, brine, dried ($MgSO_4$), filtered and concentrated under vacuum. The crude product 1j is used as for the next reaction step (5.1 g, 98% yield).

Step 10:

Acid 1j (5.1 g) is dissolved in anhydrous DCM (100 mL) at 0° C. before adding anhydrous DMF (50 μL). To this solution, oxalyl chloride (1.62 mL, 17 mmol) is slowly added. The solution is allowed to warm to RT and after 20 min; the reaction mixture is concentrated to give a foamy solid, which is used directly in the subsequent step.

A solution of (R-(+)-4-benzyl-2-oxazolidinone (6.46 g, 36.4 mmol) in 75 mL of anhydrous THF is cooled to a –78° C. and then n-BuLi (2.5 M in hexanes, 13.6 mL, 34 mmol) was added dropwise. The resulting solution is stirred for 20 min before being treated with the acid chloride (prepared above) in THF (75 mL). The mixture is stirred at –78° C. for 15 min and then allowed to warm slowly to RT and then is stirred for an additional 30 min. The reaction mixture is quenched with a saturated solution of $NH_4Cl$, followed by water. The mixture is extracted with DCM (3×), dried over $MgSO_4$, filtered and concentrated under vacuum. The mixture of diastereoisomers is separated by flash column chromatography using benzene/EtOAc 95/5 to give the desired compound 1k (2.99 g, 43% yield, elutes 2nd) plus diastereomer (2.88 g, 41% yield, elutes 1st).

Step 11:

To a solution of compound 1k (2.99 g, 5.18 mmol) in THF (50 mL)/water (15 mL) at 0° C. was added pre-mixed $H_2O_2$ (1.6 mL, 15.5 mmol)/LiOH—$H_2O$ (261 mg, 6.21 mmol) in water (10 mL). The reaction is stirred at 0° C. for 20 min. The reaction mixture is quenched at 0° C. with saturated $Na_2SO_3$ (10 mL) and allowed to stir for 10 min. The pH is adjusted to pH ~4-5 using 1 N HCl (aq) before being extracted with DCM (3×). The organic phase is dried over $MgSO_4$, filtered and concentrated under vacuum. The crude product is diluted with EtOAc (100 mL) and treated at RT with diazomethane/ether solution until complete conversion to the ester. The reaction mixture is quenched with silica gel and then carefully concentrated under vacuum. The material is dry packed and purified by flash column chromatography using DCM/acetone 9/1 to give the key thienopyridine fragment IA as a white solid (2.13 g, 95% yield).

Example 2

Synthesis of Thienopyridine Scaffold IB

The key thienopyridine fragment IB was prepared starting from commercially available thiophene 2a using the same synthetic protocols as shown for Example 1.

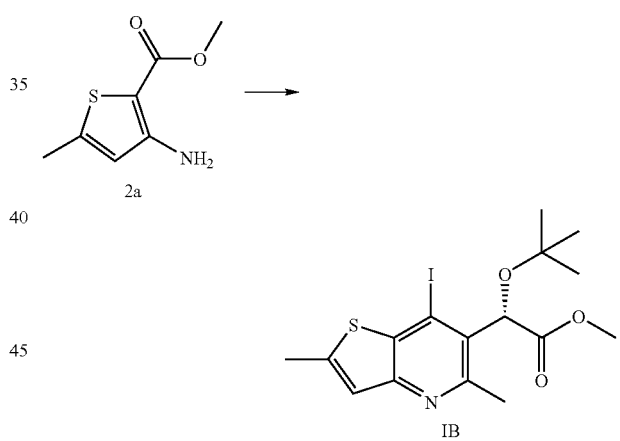

Example 3

Synthesis of Fragment 3f

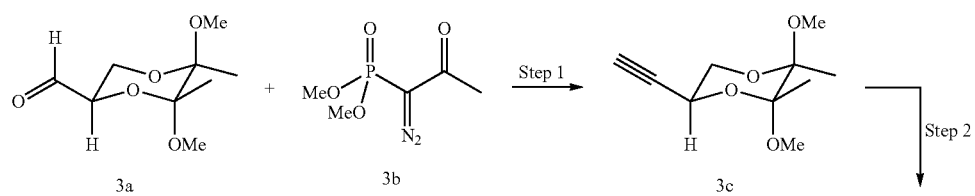

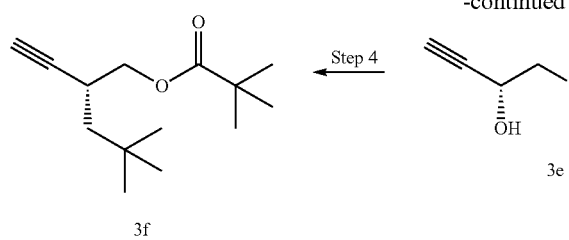
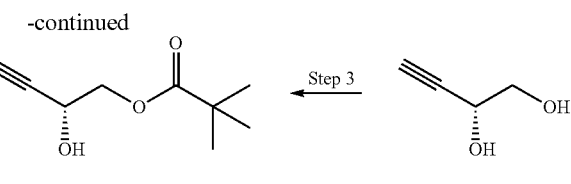

Step 1:

Aldehyde 3a (5.85 g, 28.6 mmol, for preparation see: Michel, P. and Ley, S. V. *Synthesis* 2003, 10, 1598-1602, herein incorporated by reference), phosphonate 3b (6.6 g, 34 mmol) and $K_2CO_3$ (8.8 g, 64 mmol) are combined in MeOH (125 mL) and the reaction is stirred overnight at RT. The reaction is evaporated nearly to dryness and the residue is partitioned between $H_2O$ (250 mL) and EtOAc (500 mL). The water layer is washed with EtOAc (2×250 mL) and the combined organic layers dried over anhydrous $Na_2SO_4$ and concentrated to give alkyne 3c (5.55 g, 97% yield).

Step 2:

Alkyne 3c (5.0 g, 25 mmol) is dissolved in TFA (35 mL) and water (3.6 mL) and the solution is stirred at RT. After 30 min, the reaction is concentrated under reduced pressure and the residue is purified by CombiFlash® Companion to give diol 3d (1.8 g, 84% yield).

Step 3:

A solution of diol 3d (1.2 g, 14 mmol) and triethylamine (1.7 mL, 12 mmol) in DCM (80 mL) is cooled to 0° C. under $N_2$. Trimethylacetylchloride is added dropwise and the resulting mixture is allowed to come to RT and stirred overnight. The reaction is then quenched with MeOH (100 mL) and stirring is continued for 20 min. The mixture is then concentrated under reduced pressure and the residue is purified by CombiFlash® Companion to give the desired mono ester 3e (550 mg, 40% yield) along with the undesired regioisomeric mono ester (378 mg, 27% yield).

Step 4:

In a sealable reaction flask, a solution of the propargylic alcohol 3e (375 mg, 2.20 mmol) and Amberlyst® H-15 resin (150 mg) in hexanes (3 mL) is cooled to −78° C. Isobutene is then bubbled through the solution until the volume approximately doubles. The tube is then sealed, brought to RT and is stirred overnight. The tube is then cooled to −78° C., is opened and brought back to RT. The mixture is then filtered through a plug of $SiO_2$ (EtOAc wash) and concentrated under reduced pressure to provide pure tert-butyl ether 3f (390 mg, 78% yield).

Example 4

Synthesis of Boronate Fragment 4f (can be Coupled to a Thienopyridine Scaffold to Provide a Compound of the Invention)

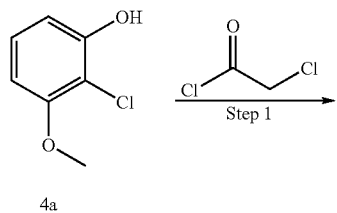

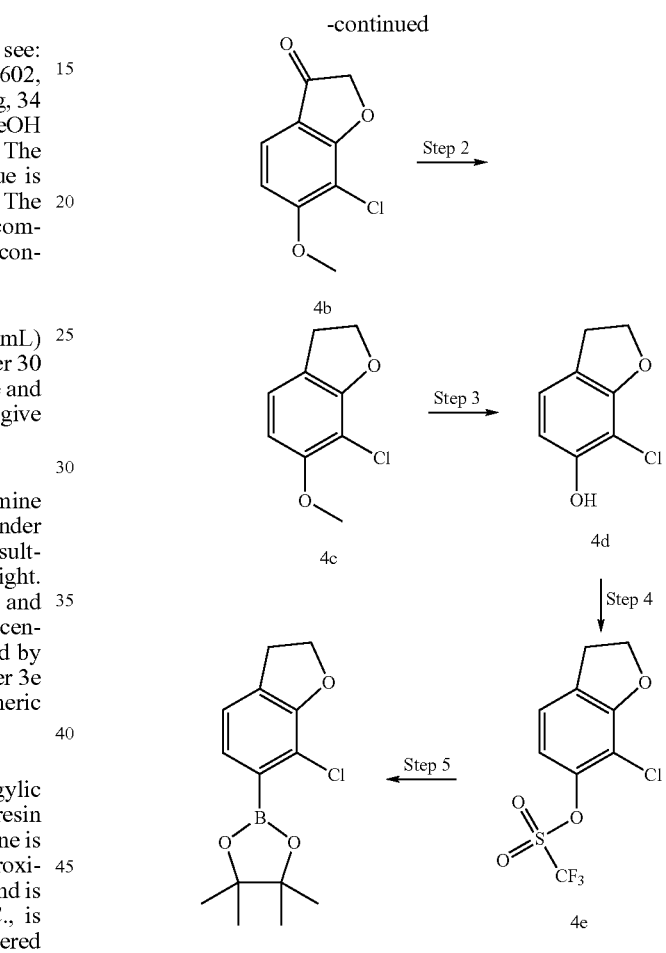

Step 1:

To a solution of 4a (6 g, 37 mmol) in nitrobenzene (12 mL), chloroacetyl chloride (4.6 mL, 57.5 mmol) is added, followed by the addition of $AlCl_3$ (20.4 g, 152 mmol). As the $AlCl_3$ is added, the mixture becomes viscous and gas evolution is observed. The resulting brown syrupy mixture is left to stir overnight at RT. (Reference: Y. Takeuchi et. al., *Chem. Pharm. Bull.* 1997, 45(12), 2011-2015.) The thick reaction mixture is cooled and ice water is added very carefully (exothermic) a few drops at a time. Once gas evolution and bubbling is subsided, cold water is further added followed by EtOAc. The mixture is stirred for 5 min and the product extracted with EtOAc (3×). The combined organic layers are washed with brine (1×), dried over $Na_2SO_4$, filtered and concentrated to afford the uncyclized chloroketone (24 g of crude; contaminated with some nitrobenzene) as a pale yellow solid. This intermediate is then taken up in EtOH (100 mL), NaOAc is added (20.4 g, 248 mmol) and the reaction is brought to reflux for 40 min. The EtOH is evaporated, the residue is taken up in EtOAc (~300 mL) and washed with 5% $K_2CO_3$ (2×200 mL) and the aqueous layer then acidified with aqueous HCl (1 N; pH ~5). This acidic layer is extracted with EtOAc (2×250 mL), washed with brine (1×), dried over $Na_2SO_4$, filtered and concentrated to afford the crude product. This material is purified by CombiFlash® Companion (120 g) to afford intermediate 4b as a yellow solid (4.7 g).

Step 2:

The ketone 4b (127 mg, 0.64 mmol) is dissolved in EtOH (2 mL) and treated with hydrazine hydrate (500 µL, 16 mmol). The mixture is heated to reflux for 45 min before allowing it to cool to RT. The solvent is removed by evaporation and the residue is dissolved in diethylene glycol (1 mL) before being treated with KOH (108 mg, 1.92 mmol) and then heated to 110-120° C. for 2.5 h. The reaction mixture is diluted with EtOAc and the pH is adjusted with 1 N HCl to pH <4. The organic phase is separated, washed with saturated brine, dried over anhydrous $MgSO_4$, filtered and concentrated. The crude material is purified by CombiFlash® Companion (eluent: 0-50% EtOAc/hexanes) to give intermediate 4c as a yellow oil (62 mg).

Step 3:

A solution of 4c (61 mg, 0.33 mmol) is cooled to –78° C. in DCM (2 mL) and then treated with $BBr_3$ (1 M in DCM, 825 µL, 0.82 mmol). After ~15 min, the bath is removed and the reaction is allowed to reach RT. The reaction is then stirred for 1.5 h. The reaction is cooled to 0° C. before quenching by the careful dropwise addition of water. The mixture is treated with saturated $NaHCO_3$ (to obtain pH ~8) and the phases separated. The organic phase is washed with saturated brine, dried over $MgSO_4$, filtered and concentrated to dryness. The product is purified by CombiFlash® Companion (0-50% EtOAc/hexanes) to give intermediate 4d as colorless oil, which solidifies upon standing (40 mg, 71% yield).

Step 4:

The phenol 4d (40 mg, 0.23 mmol) is dissolved in DCM (2 mL), cooled to 0° C. and treated with pyridine (95 µL, 1.17 mmol), followed by $Tf_2O$ (44 µL, 0.26 mmol). The reaction is allowed to stir at this temperature for 10 min before warming to RT over a period of 1 h. The reaction mixture is diluted with DCM and the organic phase washed with 10% citric acid and then brine. The organic phase is dried over anhydrous $MgSO_4$, filtered, concentrated and purified by CombiFlash® Companion (0-50% EtOAc/hexanes) to give 4e as a yellow oil (67 mg, 94% yield).

Step 5:

To a solution of the triflate 4e (66 mg, 0.22 mmol) in DMF (2 mL), bispinacolatodiborane (72 mg, 0.28 mmol) and potassium acetate (64 mg, 0.65 mmol) are added. This solution is de-gassed (with bubbling Ar) for 10 min before adding $PdCl_2$ (dppf)-$CH_2Cl_2$, (27 mg, 0.03 mmol). The mixture is de-gassed a further 5 min before being heated to 90° C. for 16 h. The mixture is cooled to RT and diluted with EtOAc/water. The organic phase is washed with saturated brine (3×), dried over anhydrous $MgSO_4$, filtered and concentrated. The crude material is purified by CombiFlash® Companion (0-70% EtOAc in hexanes) to afford the boronate 4f as a white solid (41 mg, 67% yield).

Example 5

Synthesis of Boronate Fragment 5f (Used for the Preparation of 1037, 1041, 1042, 2020, 2021)

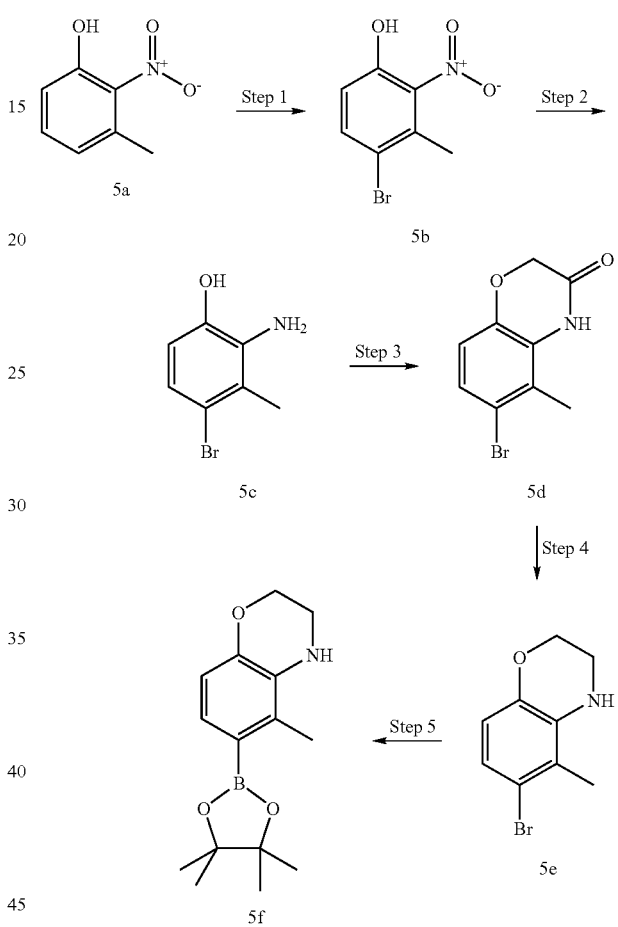

Step 1:

The nitrophenol 5a (5.23 g, 34.1 mmol) is dissolved in acetic acid (20 mL) and the solution is cooled in an ice bath. Bromine (1.75 mL, 34.15 mmol, dissolved in 5 mL acetic acid) is added dropwise with stirring. The mixture is stirred for 1 h at 0° C. before being poured into ice water (250 mL). The mixture is extracted with EtOAc (2×100 mL) and then washed with 5% $NaHCO_3$ (2×50 mL) before being dried over anhydrous $MgSO_4$, filtered and concentrated to give the desired crude product 5b as an orange solid (8.2 g, quantitative yield). This material is used in the next step without further purification.

Step 2:

To a well stirred ethanol solution (75 mL) of 5b (8.1 g, 34.9 mmol), $SnCl_2$ (20 g, 105 mmol) is added. The reaction mixture is stirred at reflux for 2.5 h. After that period, the transformation is incomplete, therefore, more $SnCl_2$ (2 g, 10 mmol) is added. Reflux is continued for 1 h before being cooled to RT. The mixture is poured onto 250 g of ice and the pH adjusted to approximately 7.5 with aqueous 5% $NaHCO_3$.

The product is extracted with EtOAc (3×100 mL) before being washed with brine (2×100 mL). The organic phase is dried over anhydrous MgSO$_4$, filtered and concentrated to dryness to give the aniline intermediate 5c as a gray solid (8.25 g, ~100% yield) this material contained some tin residues, nonetheless, it is used as such for the following step).

Step 3:

To a stirring, ice cold, DMF (5 mL) suspension of potassium carbonate (2.05 g, 14.8 mmol) and aniline 5c (750 mg, 3.71 mmol) under nitrogen, chloroacetyl chloride (355 μL, 4.45 mmol) is added dropwise. The mixture is allowed to warm to RT over a period of 15 min and then heated to ~60° C. for 1 h. The mixture is allowed to cool to RT, is poured into a mixture of ice/water (250 mL) and is stirred for approximately 15 min. The suspension is centrifuged, and the supernatant is discarded. The solid material is left drying under suction overnight to give intermediate 5d (280 mg, 31% yield).

Step 4:

To an ice cold THF (6 mL) solution of the cyclic amide 5d (280 mg, 1.16 mmol) under nitrogen, a borane-THF solution (1M in THF, 1.74 mL, 1.74 mmol) is added slowly. The reaction mixture is slowly allowed to warm to RT, then is stirred at RT for approximately 1.5 h and then gently heated to reflux for 1 h to complete the conversion. The mixture is cooled in an ice bath and is carefully quenched with aqueous 1 M NaOH (4 mL) over 10 min. The reaction mixture is partitioned between EtOAc (150 mL) and water (25 mL). The organic layer is washed with aqueous 1 N NaOH (20 mL) and brine, dried over anhydrous MgSO$_4$, filtered and concentrated to give the crude 5e as an amber oil (212 mg, 81% yield). This product is used as such for next transformation.

Step 5:

A well stirred DMF (15 mL) solution of the arylbromide 5e (0.50 g, 2.19 mmol), potassium acetate (0.728 g, 7.67 mmol) and bis(pinacolato)diborane (0.83 g, 3.3 mmol) is degassed by bubbling Ar through the solution for 20 min. PdCl$_2$(dppf)-DCM (320 mg, 0.44 mmol) is added and degassing is continued for 15 min. The system is sealed (teflon screw cap vessel) under Ar and heated to ~90° C. for 5 h. The reaction mixture is allowed to cool to RT, dilute with EtOAc (150 mL), washed with brine (3×100 mL) and water (2×100 mL), dried over anhydrous MgSO$_4$, filtered and concentrated to dryness. The residue is purified by CombiFlash® Companion (EtOAc/hexanes) to give the desired boronate 5f (389 mg, 65% yield) as a yellowish waxy solid.

Example 6

Synthesis of Boronate Fragment 6i (Used for the Preparation of 1027, 1028, 2007, 2008)

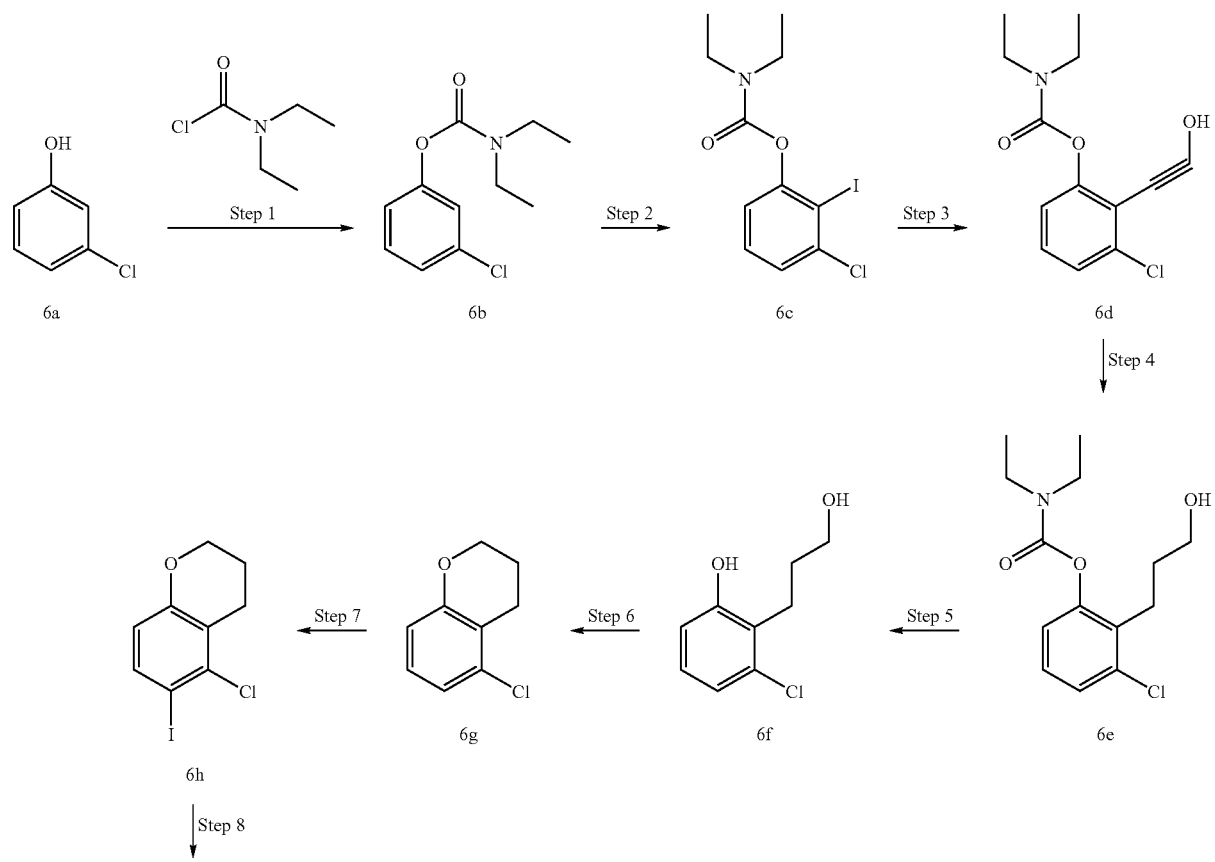

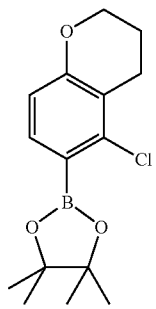

6i

Step 1:

Sodium hydride (60%, 7.78 g, 194 mmol) is added to a well stirred suspension of 6a (12.5 g, 97 mmol) in THF (100 mL). After stirring the reaction mixture for 1 h, N,N-diethylcarbamoyl chloride (24.64 mL, 194 mmol) is added at RT. After stirring the reaction overnight, the reaction mixture is quenched with water (100 mL), extracted with EtOAc (3×50 mL), dried over anhydrous MgSO$_4$, filtered and evaporated under reduced pressure to obtain 6b (33 g, 75% yield) in high purity.

Step 2:

Diisopropylamine (21.0 mL, 121 mmol) in THF (330 mL) is treated with a solution of n-BuLi (2.5 M in hexanes, 48.2 mL, 121 mmol) at 0° C. After 30 min at this temperature, the solution is cooled to −78° C. and carbamate 6b (33.29 g, 109.7 mmol, 75% pure) is added. The reaction is stirred at this temperature for 30 min and then iodine (33.4 g, 132 mmol) is added. The solution is stirred for 30 min at 0° C. and is then warmed to RT. After 2 h, the reaction mixture is quenched with water (250 mL) and the volatile organic solvents are removed under reduced pressure. The aqueous phase is then extracted with EtOAc (3×100 mL), washed with 1 N HCl (1×200 mL), dried over MgSO$_4$, filtered and evaporated under reduced pressure to obtain 6c (18.6 g, 39% yield).

Step 3:

The iodocarbamate 6c (10 g, 28 mmol), propargyl alcohol (3.3 mL, 56 mmol), Pd(PPh$_3$)$_4$ (3.27 g, 2.83 mmol) and copper iodide (1.08 g, 5.66 mmol) are combined in diisopropylamine (39 mL, 39 mmol) in a sealable tube under Ar and heated at 100° C. After 1 h, the reaction is cooled to RT and poured into EtOAc (100 mL) and this mixture is extracted with 10% HCl (2×100 mL). The organic layer is dried over MgSO$_4$ and concentrated to dryness. The crude product is purified by CombiFlash® Companion to obtain the alcohol 6d (3.65 g, 46% yield).

Step 4:

Alkyne 6d (3.63 g, 12.9 mmol) is dissolved in EtOAc (81 mL) and treated with Rh—Al$_2$O$_3$ (5% w/w, 3.45 g, 1.68 mmol). The flask is evacuated and charged with 1 atmosphere of H$_2$ (balloon) and the reaction is stirred overnight at RT. The reaction mixture is filtered through Celite® (EtOAc wash) and the filtrate is concentrated under reduced pressure. The residue is then purified by CombiFlash® Companion to obtain alcohol 6e (3.7 g, 71% yield).

Step 5:

Solid NaOH (920 mg, 23 mmol) is added to a solution of the carbamate 6e (2.63 g, 9.20 mmoL) in EtOH (93 mL) and the mixture is heated to reflux and is stirred overnight. The mixture is then cooled to RT and the organic solvent removed under reduced pressure. Water is added (100 mL) and the mixture extracted with Et$_2$O (3×100 mL), dried over MgSO$_4$, filtered and evaporated under reduced pressure to obtain phenol 6f (869 mg, 51% yield).

Step 6:

Diethyl azodicarboxylate (953 µL, 6.05 mmol) is added dropwise to a solution of phenol 6f (869 mg, 4.66 mmol) and PPh$_3$ (1.59 g, 6.05 mmol) in THF (65 mL) and the reaction is stirred at RT. After 4 h, the reaction mixture is evaporated under reduced pressure. The residue is then purified by CombiFlash® Companion to obtain the chroman intermediate 6g (387 mg, 49% yield).

Step 7:

Iodine (583 mg, 2.30 mmol) is added to a solution of chroman 6g (387 mg, 2.29 mmol) and AgNO$_3$ (429 mg, 2.52 mmol) in MeOH (23 mL). After 20 min, a 0.5 M solution of sodium thiosulfate (10 mL) is added and the aqueous phase extracted with EtOAc (3×25 mL). The combined organic phases are washed with brine, then dried (MgSO$_4$), filtered and evaporated to obtain aryl iodide 6h (647 mg, 96% yield).

Step 8:

A solution of iodo intermediate 6h (647 mg, 2.20 mmol), bis(pinocolato)diborane (0.725 g, 2.86 mmol) and potassium acetate (0.626 g, 6.59 mmol) in DMF (17 mL) is degassed with Ar for 10 min. PdCl$_2$(dppf)-DCM complex (179 mg, 0.22 mmol) is then added and the mixture is degassed with Ar for approximately another 5 min. The reaction is then heated to 95° C. in a sealable tube and is stirred overnight. The reaction is cooled to RT and EtOAc (100 mL) is added. The solution is washed with brine (3×150 mL), water (1×150 mL), dried over MgSO$_4$, filtered and solvent removed under reduced pressure. The residue is purified by CombiFlash® Companion to afford boronate ester 6i (260 mg, 40% yield).

Example 7

Synthesis of Boronate Fragment 7d (Used for the Preparation of 1038, 1039, 1043, 1044, 2026, 2027)

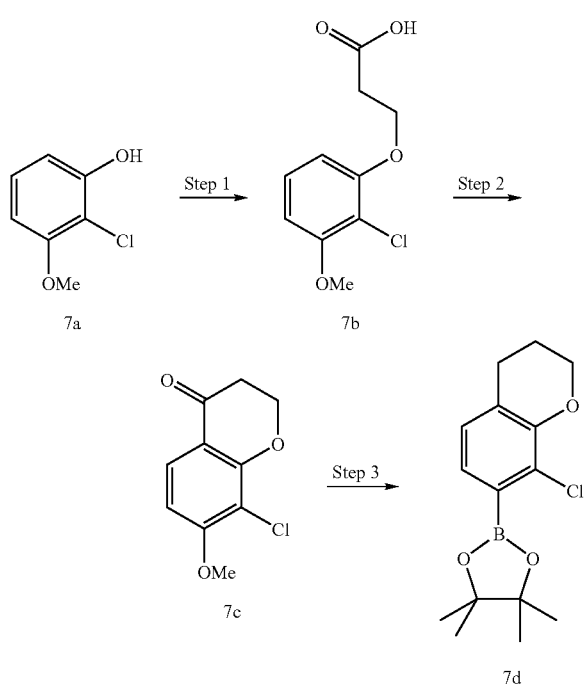

Step 1:
A solution of phenol 7a (0.91 g, 5.74 mmol) in dry DMF (1 mL) is added dropwise to a slurry of NaH (60% in oil, 0.60 g, 15 mmol) in dry DMF (1 mL) cooled to 10-15° C. (cold water bath) and the mixture is stirred for 20 min. This results in a thick, frothy white mixture. A solution of 3-bromopropionic acid (1.1 g, 6.9 mmol) in dry DMF (0.5 mL) is then added dropwise and the reaction stirred at RT overnight. After 16 h, methanol (1.2 mL) is added to help break up the thick, pasty reaction mixture which is then added to diluted HCl (~12 mL; 1 N HCl in 100 mL water) and extracted with EtOAc (80 mL; the pH of the aqueous phase is adjusted to pH <3). The organic layer is dried over anhydrous $Na_2SO_4$ and evaporated to give 7b as a white solid material, contaminated with some unreacted SM (1.29 g of crude material). This material is used in the next step without purification.

Step 2:
The crude compound 7b (1.53 g, 6.63 mmol) is combined with polyphosphoric acid (approximately 7 g) and heated to 75° C. to give a cherry red colored solution. During the reaction time, the reaction mixture becomes viscous and stirring becomes difficult. After 4 h, ice and water are slowly added with rapid stirring to give a thick suspension. This mixture is transferred to a separatory funnel where the product is extracted with EtOAc (100 mL) and washed with water (100 mL), saturated $NaHCO_3$ (2×100 mL) and brine (75 mL). The organic phase is dried over anhydrous $MgSO_4$ and evaporated to give a sticky violet solid 7c which is used as such (1.29 g crude).

Step 3:
Intermediate 7c is analogous to intermediate 4b in Example 4; those skilled in the art would recognize that the same synthetic methodologies used to convert 4b to the boronate 4f can be applied for the conversion of 7c to the corresponding boronate 7d.

Example 8

Synthesis of Boronate Fragment 8h (can be Coupled to a Thienopyridine Scaffold to Provide a Compound of the Invention)

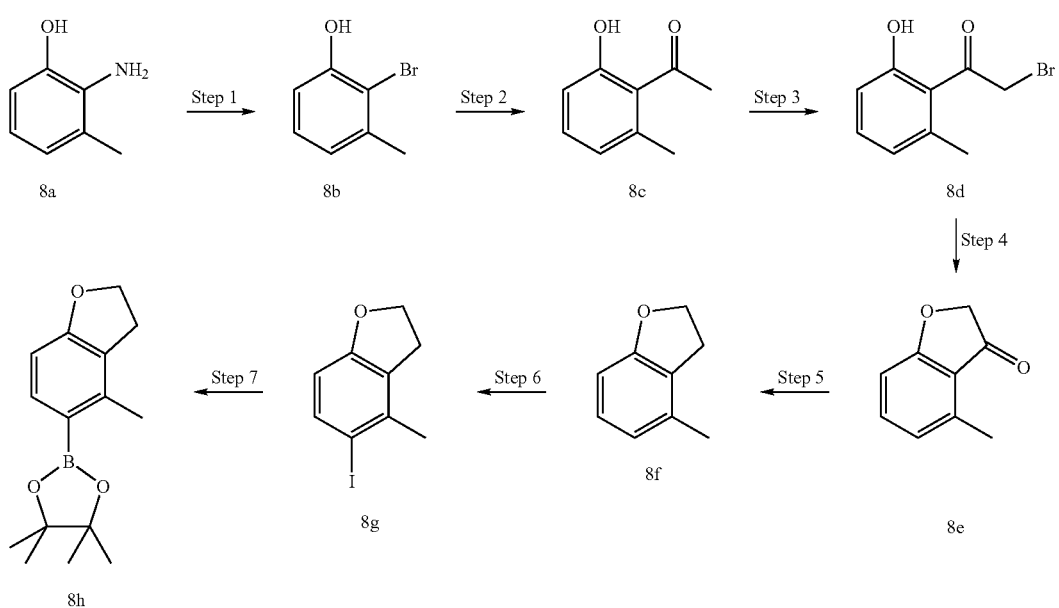

Step 1

2-Amino-m-cresol 8a (5.7 g, 46.3 mmol) is dissolved in H₂O (30 mL) and 1,4-dioxane (15 mL). The mixture is heated to reflux and then HBr (48%, 17 mL, 310 mmol) is added dropwise over a period of 20 min. The reflux is maintained for an additional 15 min after the addition is complete. The reaction is cooled to 0° C., and NaNO₂ in H₂O (20 mL) is added over a period of 30 min. The stirring is continued for 15 min at 0° C., the mixture is then transferred in one shot to a stirring mixture of Cu(I)Br (7.64 g, 53.2 mmol) in H₂O (20 mL) and HBr (48%, 17 mL, 310 mmol) at 0° C. (protected from light). The reaction is stirred for 15 min at 0° C., is warmed to 60° C., is stirred for an additional 15 min, is cooled to RT and is then stirred overnight. The reaction mixture is then transferred to a separatory funnel and extracted with EtOAc (3×). The organic layers are combined, washed with brine, dried over anhydrous MgSO₄, filtered and concentrated over silica to afford a mixture that is purified using the CombiFlash® Companion (20% EtOAc/hexanes) to afford the desired bromide 8b (1.46 g, 17% yield) as a red-brown oil.

Step 2:

To a solution of the bromide 8b (1.36 g, 7.27 mmol) and (PPh₃)₂PdCl₂ (766 mg, 1.09 mmol) in DMF (12 mL), 1-ethoxyvinyl-tri-n-butyltin (2.7 mL, 8.0 mmol) is added. The mixture is capped and heated in a microwave at 160° C. for 15 min. HPLC and LC-MS analysis indicate approximately 70% conversion. More 1-ethoxyvinyl-tri-n-butyltin (2.7 mL, 8.0 mmol) and catalyst (PPh₃)₂PdCl₂ (380 mg, 0.05 mol %) are added and the solution is again subjected to the same microwave conditions. The reaction is quenched with 6N HCl (1.5 mL) and stirred at RT for 1 h to effect hydrolysis of the intermediate. The mixture is poured into EtOAc (150 mL), washed with brine (3×), dried over MgSO₄, filtered and concentrated over silica to afford the mixture that is purified using the CombiFlash® Companion to afford the desired ketone 8c (947 mg, 87% yield) as an orange oil.

Step 3:

The methyl ketone 8c (1.02 g, 6.8 mmol) is dissolved in EtOAc (15 mL) and CHCl₃ (15 mL) before being treated with Cu(II)Br₂ (3.03 g, 13.6 mmol). The mixture is heated to reflux for 16 h. The mixture is cooled to RT, the product filtered and washed with EtOAc (1×). The solution is concentrated over silica to afford the mixture that is purified using the CombiFlash® Companion (10% EtOAc/hexanes) to afford the α-bromoketone 8d (710 mg, 46% yield) as an orange oil. The material is used as is in the next step without purification.

Step 4:

To a solution of the bromoketone 8d (710 mg, 3.1 mmol) in anhydrous DMF (12 mL), KF (400 mg, 6.95 mmol) is added. The reaction is stirred at RT for 16 h. The mixture is taken up in EtOAc (150 mL), washed with brine (3×), dried over anhydrous MgSO₄, filtered and concentrated over silica to afford the mixture that is purified using the CombiFlash® Companion (20% EtOAc/hexanes) to afford the cyclic ketone 8e (280 mg, 61% yield) as a pale orange solid.

Step 5:

Zn dust pre-activation procedure: Zinc dust (20 g, 350 mesh) is placed in a round bottom flask and 1 N HCl (50 mL) is added. This suspension is sonicated for 1 min before decanting off the liquid. This procedure is repeated for a second time after which the solid is washed with EtOH (2×), Et₂O (2×) and dried under high vacuum. To a solution of the ketone 8e (280 mg, 1.89 mmol) in AcOH (10 mL) pre-activated Zn dust (1.24 g, 18.9 mmol) is added. The reaction mixture is then heated to 75° C. for 2 h. The reaction mixture is filtered (with EtOAc washing of the solids). The solvent is evaporated over silica and the mixture is directly purified using the CombiFlash® Companion (10% EtOAc/hexanes) to afford the desired dihydrobenzofuran 8f (174 mg, 69% yield) as a colorless oil.

Step 6:

To a solution of the dihydrobenzofuran 8f (240 mg, 1.8 mmol) in MeOH (5 mL), AgNO₃ (304 mg, 1.79 mmol) is added followed by iodine (453 mg, 1.79 mmol). The yellow mixture is stirred at RT for 1 h. To the reaction mixture is added a solution of 10% Na₂S₂O₃ and the mixture is stirred for 15 min at RT. The mixture is diluted with EtOAc (100 mL), and the organic layer is washed with brine (3×) and 10% Na₂S₂O₃ (2×). The organic phase is dried over anhydrous MgSO₄, filtered and concentrated over silica to give a mixture. This mixture is purified using the CombiFlash® Companion (10% EtOAc/hexanes) to afford the iodo derivative 8g (400 mg, 86% yield) as a white amorphous solid.

Step 7:

A mixture of the iodo derivative 8g (400 mg, 1.54 mmol), bis(pinocolato)diborane (585 mg, 2.31 mmol), potassium acetate (511 mg, 5.4 mmol) in DMF (20 mL) is deoxygenated (Ar balloon and sonication for 5 min); then the catalyst (PdCl₂dppf, 188 mg, 0.23 mmol) is added with additional degassing (Ar balloon and sonication for 2 min). The mixture is then heated to approximately 95° C. for 4 h. The mixture is cooled, EtOAc (200 mL) is added, washed with brine (3×), water (2×), dried over anhydrous MgSO₄, filtered and solvent evaporation over silica affords the mixture that is purified using the CombiFlash® Companion (10% EtOAc/hexanes) to afford the desired boronate 8h (315 mg, 79% yield) as a yellow oil.

Example 9

Synthesis of Boronate Fragment 9b (Used for the Preparation of 1053, 1054)

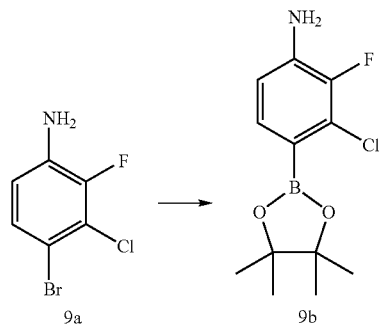

Anhydrous DMF (60 mL) is added to a flask charged with bromide 9a (5.00 g, 22.2 mmol), bis-(pinacolato)diboron (8.48 g, 33.4 mmol) and potassium acetate (6.35 g, 66.8 mmol) and the resulting suspension is deoxygenated by bubbling a stream of N₂ gas through the mixture for 45 min. 1,1'-bis(diphenylphosphino)ferrocene (2.73 g, 3.34 mmol) is then added and the mixture is deoxygenated for approximately a further 5 min and is then heated to 95° C. After 16 h, the dark reaction mixture is cooled, extracted with EtOAc (500 mL and 300 mL) and washed with 1:1 water/brine (600 mL) and brine (600 mL). The combined extracts are dried over anhydrous MgSO₄, filtered and evaporated to a black syrup which is purified by flash column chromatography

Example 10

Synthesis of Boronate Fragment 10g (Used for the Preparation of 1045, 1046, 1051, 1052, 2024, 2025)

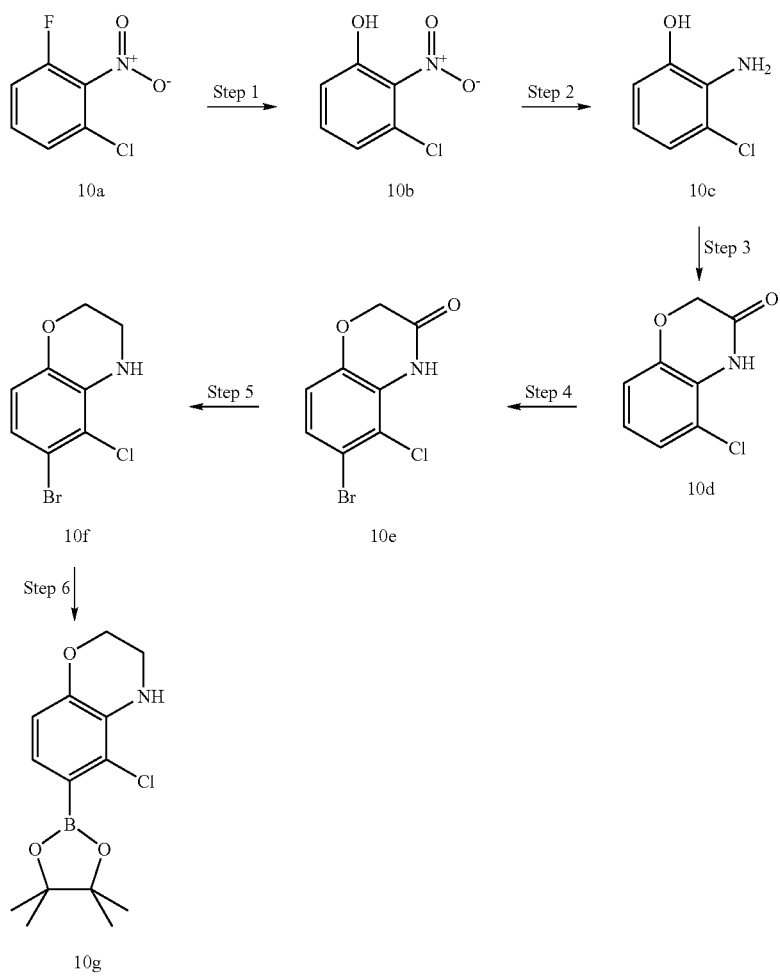

Step 1:

2-Chloro-6-fluoronitrobenzene 10a (6.62 g, 37.7 mmol) and LiOH monohydrate (6.33 g, 151 mmol) are dissolved in THF (45 mL) and water (65 mL) and an aqueous solution of $H_2O_2$ (30%, 8.60 mL, 80.0 mmol) added. The resulting turbid solution is sealed and is heated to 60° C. with rapid stirring. After 3 days, the dark orange mixture is cooled and is added to half-saturated aqueous sodium thiosulfate (200 mL) and shaken vigorously in a separatory funnel. The mixture is then acidified to pH <3 with 1 N HCl, extracted with EtOAc (400 mL+100 mL) and washed with brine (400 mL). The combined extracts are dried over $MgSO_4$, filtered and evaporated to give 10b as a deep yellow oil containing some solid particles (residual starting material) which is used as such (6.37 g, 97% yield).

Step 2:

The crude aminophenol 10b (6.37 g. 36.7 mmol) is dissolved in THF (100 mL) and tin powder (17.4 g, 147 mmol) is added followed by 1 N HCl (220 mL, 220 mmol). The resulting mixture is stirred vigorously at RT. After 16 h, the reaction is cooled to 0° C., the acid neutralized with 10 N NaOH (22 mL) and the resulting milky suspension stirred vigorously for 15 min. The mixture is then filtered through a pad of Celite® and the solids washed thoroughly with EtOAc (4×200 mL). The filtrate is transferred to a separatory funnel and the aqueous phase acidified with 1 N HCl (4 mL), diluted with brine (400 mL) and the organic phase washed with brine (400 mL). The extract is then dried over sodium sulfate, filtered and evaporated to afford aminophenol 10c as a waxy, pale brown solid (2.91 g, 55% yield).

Step 3:

Chloroacetyl chloride (1.94 mL, 24.3 mmol) is added to an ice-cold mixture of aminophenol 10c (2.91 g, 20.3 mmol) and potassium carbonate (8.40 g, 60.8 mmol) in anhydrous DMF (200 mL) under a $N_2$ atmosphere. After 5 min, the reaction is allowed to warm to RT and, after a further 45 min, is heated to 50° C. After 15 h, the reaction is cooled and extracted with EtOAc (600 mL) and washed with water/brine (1 L), half-saturated sodium bicarbonate (1 L) and brine (600 mL). The organic phase is then dried over $MgSO_4$, filtered and evaporated to afford lactam 10d as a fibrous, pale-olive solid (3.15 g, 85% yield).

Step 4:

Bromine (1.8 mL; 35 mmol) is slowly added dropwise to a stirred solution of lactam 10d (3.15 g; 17.1 mmol) in anhydrous DCM (40 mL) at RT. After 3 h, the resulting suspension is slowly added to saturated aqueous sodium thiosulfate (200 mL) and extracted with DCM (4×100 mL). The combined extracts are then washed with brine (200 mL), dried over MgSO$_4$, filtered and evaporated to afford the bromide 10e as a pale beige powder (4.00 g, 89% yield).

Step 5:

A solution of borane in THF (1.0 M, 18.5 mL, 18.5 mmol) is added dropwise to an ice-cold solution of lactam 10e (4.00 g, 15.2 mmol) in anhydrous THF (75 mL), and the reaction is allowed to warm to RT. After 30 min, the solution is heated to gentle reflux under a N$_2$ atmosphere. After 2 h, the reaction is cooled to 0° C. and carefully quenched with 1 N NaOH (19 mL) and stirred for 15 min. The mixture is then diluted with water (30 mL) and the THF is evaporated. The aqueous residue is then extracted with EtOAc (400 mL+50 mL) and washed with water/brine (200 mL), 0.5 N NaOH (200 mL) and brine (100 mL). The combined extracts are dried over MgSO$_4$, filtered and evaporated to afford the morpholine derivative 10f as a yellow syrup (3.90 g, quantitative yield).

Step 6:

Anhydrous DMF (30 mL) is added to a flask charged with aryl bromide 10f (1.84 g, 7.42 mmol), bis(pinacolato)diborane (2.83 g, 11.1 mmol) and potassium acetate (2.47 g, 26.0 mmol) and the resulting suspension is then deoxygenated by bubbling a stream of N$_2$ gas through the mixture for 15 min. 1,1'-bis(diphenylphosphino)ferrocene (909 mg, 1.11 mmol) is then added and the mixture is deoxygenated for a further 5 min and then heated to 95° C. After 16 h, the dark reaction mixture is cooled, diluted with EtOAc (300 mL) and washed with 1:1 water/brine (500 mL) and brine (200 mL). The extract is then dried over MgSO$_4$, filtered and evaporated to a brown syrup which is chromatographed over silica gel (EtOAc/hexanes) to afford the boronate 10g as a white solid contaminated with 0.8 eq of the diboron reagent (1.52 g, 69% yield).

Example 11

Synthesis of Boronate Fragment 11d (Used for the Preparation of 1009, 1011, 1013, 2001, 2014, 2015, 2028, 2033, 2034)

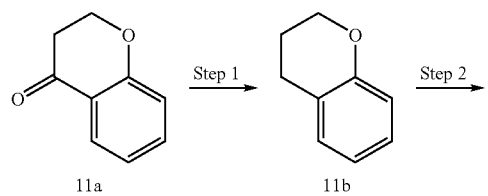

-continued

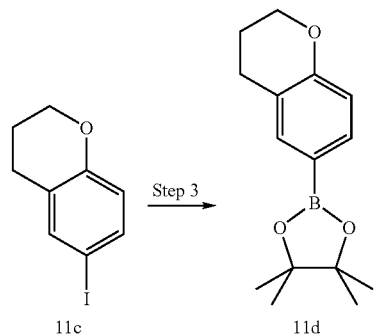

Step 1:

Commercially available chromanone 11a (9.78 g, 66.0 mmol) dissolved in AcOH (20 mL) is added to a suspension of zinc dust (108 g, 1.65 mol) in AcOH (150 mL). The mixture is heated to 100° C. and is stirred mechanically overnight. The mixture is then filtered through Celite® (washed with EtOAc, 100 mL), diluted with PhMe (300 mL) and the solution is evaporated to give chroman intermediate 11b (8.45 g, 95% yield).

Step 2:

AgNO$_3$ (12.0 g, 70.6 mmol) and I$_2$ (15.8 g, 62.3 mmol) are added sequentially to a solution of 11b (8.45 g, 63.0 mmol) dissolved in MeOH (225 mL). The reaction is allowed to stir for 1 h, filtered on Celite® and the filtrate concentrated under reduced pressure. The crude mixture is diluted with EtOAc (250 mL) and washed with saturated sodium thiosulfate (250 mL). The organic layer is washed with water (200 mL) and then dried over Na$_2$SO$_4$, filtered and concentrated. The crude mixture is further purified by CombiFlash® Companion to give 6-iodochroman 11c (12.1 g, 74% yield).

Step 3:

A solution of the 6-iodochroman 11c (1.0 g, 3.85 mmol), bis[pinocolato]diborane (1.22 g, 4.81 mmol) and potassium acetate (1.10 g, 11.5 mmol) in DMF (36 mL) is degassed with Ar for 5 min followed by the addition of the PdCl$_2$dppf-DCM complex (314 mg, 0.38 mmol). The reaction mixture is then degassed for an additional 5 min before being heated to 95° C. for 5 h. The reaction is then cooled to RT. The crude reaction mixture is diluted with water and the product is extracted with EtOAc (3×100 mL). The combined organics are washed with water (100 mL) and brine (100 mL). The organic phase is then dried over MgSO$_4$ and filtered and concentrated. The crude mixture is further purified by CombiFlash® Companion using a gradient of EtOAc/hexanes to afford the borane fragment 11d (840 mg, 84% yield).

Example 12

Synthesis of Boronate Fragment 12g (Used for the Preparation of 1029, 2009, 2010)

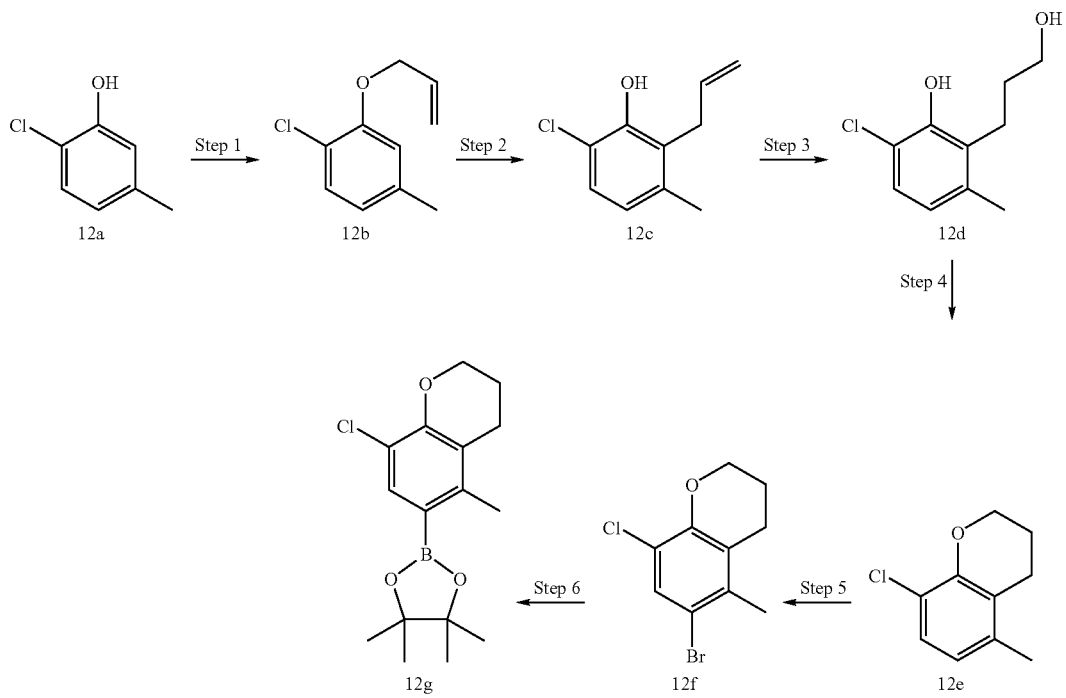

Step 1:
The phenol 12a (6.75 g, 47.3 mmol) is dissolved in DMF (270 mL) and is treated with allyl bromide (6.55 mL, 75.7 mmol). To this solution, NaH (60%, 4 g, 99.4 mmol) is added portionwise and stirring is continued overnight. The reaction mixture is diluted with EtOAc (500 mL) and washed with $H_2O$ (3×500 mL). The organic layer is dried over $MgSO_4$, filtered and concentrated to dryness to obtain the desired product 12b, which is used as such in the next step.

Step 2:
The ether 12b (9.67 g) is placed in a microwave vial neat with a stir bar and is heated to 240° C. for 20 min at which point the Claisen rearrangement reaction is complete. The crude product 12c (9.3 g) is used in the following step without further purification.

Step 3:
To a solution of the allyl intermediate 12c (9.3 g, 45.8 mmol) in anhydrous THF (300 mL) at 0° C., borane (1 M in THF, 96 mL, 96 mmol) is added. The solution is allowed to warm to RT and then is stirred for 2.5 h. The solution is then cooled to 0° C. and treated with 10 N NaOH dropwise, followed by slow addition of 30% $H_2O_2$ (104 mL, 916 mmol). The resulting mixture is allowed to warm to RT and then is stirred at RT for 1 h. The reaction mixture is diluted with HCl (10%, 100 mL) and extracted with EtOAc (3×200 mL). The combined organic phases are dried over $MgSO_4$ and concentrated. The crude product is purified by CombiFlash® Companion to give 12d (7.1 g, 77% yield).

Step 4:
To a solution of the diol 12d (7.1 g, 35.3 mmol) in THF (500 mL), $PPh_3$ (12 g, 45.9 mmol), followed by DEAD (7.2 mL, 45.9 mmol) are added. The solution is stirred at RT for 4 h. The reaction mixture is evaporated under reduced pressure and purified by CombiFlash® Companion to obtain the desired product 12e (5.26 g, 82% yield).

Step 5:
The chroman derivative 12e (5.26 g, 28.8 mmol) is dissolved in AcOH (70 mL) and is then treated with $Br_2$ in AcOH (40 mL). The reaction is stirred at RT for 15 min, then diluted with toluene and concentrated to dryness. The residue is taken up in EtOAc (25 mL) and washed with saturated $Na_2S_2O_3$ (25 mL) and saturated $NaHCO_3$ (25 mL). The organic layer is dried over $MgSO_4$, concentrated and purified by CombiFlash® Companion to obtain the desired product 12f (2.7 g, 36% yield).

Step 6:
The bromide 12f (2.71 g, 10.4 mmol) is dissolved in DMF (120 mL) and treated with bis[pinocolato]diborane (4 g, 15.5 mmol) and potassium acetate (3.45 g, 36.3 mmol). The mixture is degassed (using an Ar balloon) before the introduction of the catalyst ($PdCl_2$dppf: 845 mg, 1.04 mmol). The mixture is then degassed again (using an Ar balloon) and heated to 95° C. for 16 h. The mixture is cooled to RT, diluted with $H_2O$ (300 mL) and extracted with EtOAc (2×300 mL). The combined organic layers are washed with water (3×300 mL) dried over $MgSO_4$, filtered and concentrated. The product is then purified by CombiFlash® Companion. The semi-purified product is then triturated with hexanes (3×50 mL) in order to remove the excess disborane and obtain clean compound 12 g (1.74 g, 54% yield).

Example 13

Synthesis of Boronate Fragment 13a (Used for the Preparation of 1030, 1031, 1040, 2011)

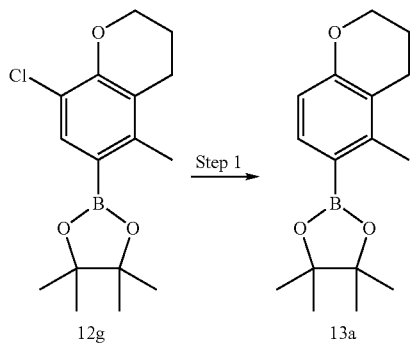

Step 1:

Palladium on activated charcoal (10% Pd by weight, 0.63 mg, 0.59 mmol) is added to a solution of aryl chloride 12g (0.91 g, 2.95 mmol) and ammonium formate (1.92 g, 30.4 mmol) dissolved in MeOH (10 mL) and the mixture is heated to reflux. After 15 min, the reaction is cooled to RT and filtered through Celite® (MeOH rinse). The filtrate is evaporated to dryness and the residue partitioned between water and EtOAc (10 mL each). The organic layer is dried over anhydrous MgSO$_4$ and concentrated to obtain boronic ester 13a (0.78 g, 97% yield).

Example 14

Synthesis of Boronate Fragment 14g (Can be Coupled to a Thienopyridine Scaffold to Provide a Compound of the Invention)

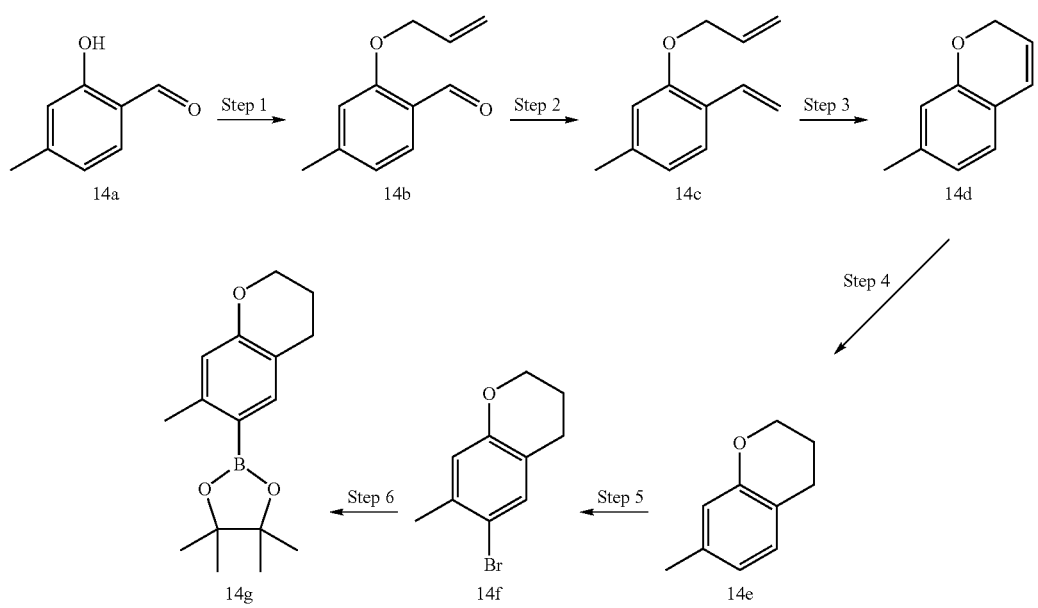

Step 1:
Allyl bromide (9.3 mL, 110 mmol) followed by potassium carbonate (20 g, 150 mmol) are added to a solution of 14a (10 g, 73 mmol) dissolved in DMF (110 mL). The reaction is allowed to stir under Ar at RT overnight. The reaction is diluted with water (400 mL) and extracted with EtOAc (400 mL). The organic layer is washed with water (2×400 mL), dried over $Na_2SO_4$ and concentrated. The product is then purified by CombiFlash® Companion in two batches (120 g column) to provide allyl ether 14b (12 g, 92% yield).

Step 2:
A solution of n-BuLi in hexanes (2.5 M, 6.4 mL, 16 mmol) is added dropwise to a precooled (−78° C.) suspension of methyltriphenylphosphonium bromide (6.6 g, 19 mmol) in THF (90 mL). The resulting bright yellow mixture is stirred for 5 min at −78° C., warmed to RT over approximately 5 min and then recooled to −78° C. Aldehyde 14b (2.4 g, 14 mmol) dissolved in THF (10 mL) is added dropwise and the reaction is allowed to proceed for 10 min at −78° C. before being allowed to warm to RT and stir overnight. The reaction is quenched with brine (100 mL), diluted with water (100 mL) and extracted with EtOAc (100 mL). The organic layer is then washed with water (2×100 mL), dried over $Na_2SO_4$ and concentrated. The crude yellow liquid is then taken up in 1 mL of EtOAc and diluted with hexanes (about 20 mL), after which $Ph_3PO$ precipitates as a white solid. The solid is removed by filtration, washed with 1:9 EtOAc:hexanes (about 50 mL) and the filtrates are evaporated to dryness. The product is purified by CombiFlash® Companion to give diene 14c (1.3 g, 54% yield).

Step 3:
Grubb's second generation catalyst (50 mg, 0.075 mmol) is added to a degassed solution of diene 14c (1.3 g, 7.5 mmol). After stirring under Ar for 2.5 h, the reaction is concentrated onto $SiO_2$ (about 2 g) and the product purified by CombiFlash® Companion to give benzopyran 14d (940 mg, 86% yield) as a clear oil.

Step 4:
Solid Pd—C (10% w/w, 680 mg, 0.64 mmol) is added to a solution of benzopyran 14d (940 mg, 6.4 mmol) in EtOH (8.5 mL) and the flask is evacuated and backfilled with $H_2$ (balloon). After stirring the reaction at RT for 2.5 h, the mixture is filtered through Celite® (EtOAc washing) and then the filtrate is concentrated to dryness. The product is purified by CombiFlash® Companion to provide chroman 14e (800 mg, 84% yield).

Step 5:
Neat $Br_2$ (275 µL, 5.4 mmol) is added dropwise to a solution of chroman 14e (800 mg, 5.4 mmol) dissolved in AcOH (25 mL). The reaction is then diluted with water (50 mL) and EtOAc (50 mL). The organic layer is washed with water (2×50 mL) and saturated $NaHCO_3$ (2×50 mL). The organic layer is dried over $Na_2SO_4$ and concentrated to dryness. The product is purified by CombiFlash® Companion to give bromide 14f as a mixture with the dibromide (1.3 g, 68% by mass 14f, 51% yield).

Step 6:
A solution of the bromide 14f (950 mg, 2.8 mmol), bis[pinocolato]diborane (840 mg, 3.3 mmol) and potassium acetate (920 g, 9.6 mmol) in DMF (30 mL) is degassed with Ar for 5 min followed by the addition of the $PdCl_2$dppf-DCM complex (290 mg, 0.36 mmol). The reaction mixture is then degassed for an additional 5 min before being heated to 95° C. for 3 h. The reaction is then cooled to RT. The crude reaction mixture is diluted with water and the product is extracted 3 times with EtOAc (3×20 mL). The combined organics are washed with water (2×20 mL). The organic phase is then dried over $Na_2SO_4$, filtered and concentrated. The crude mixture is further purified by CombiFlash® Companion to afford boronic ester 14g (403 mg, 53% yield) as a pale yellow solid.

Example 15

Synthesis of Boronate Fragment 15l (Can be Coupled to a Thienopyridine Scaffold to Provide a Compound of the Invention)

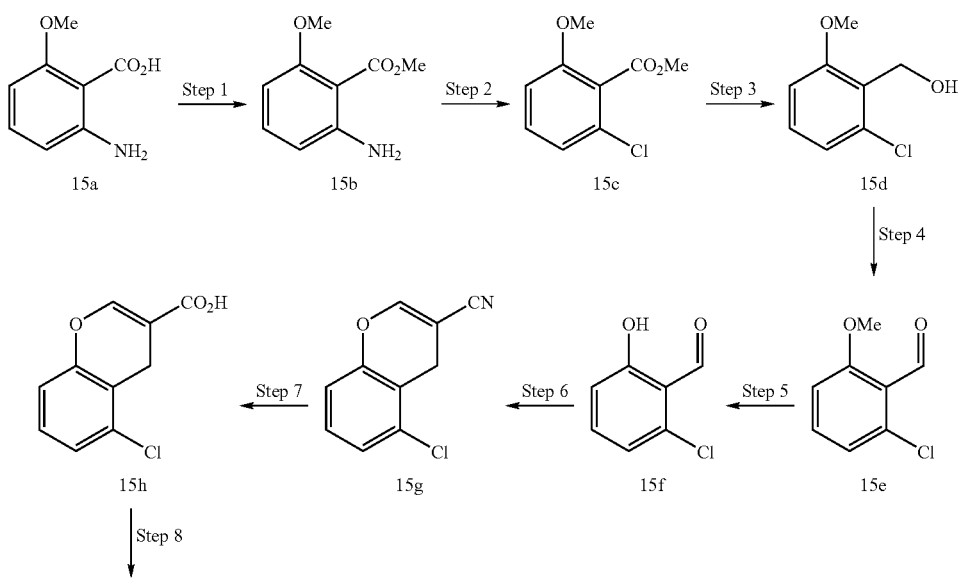

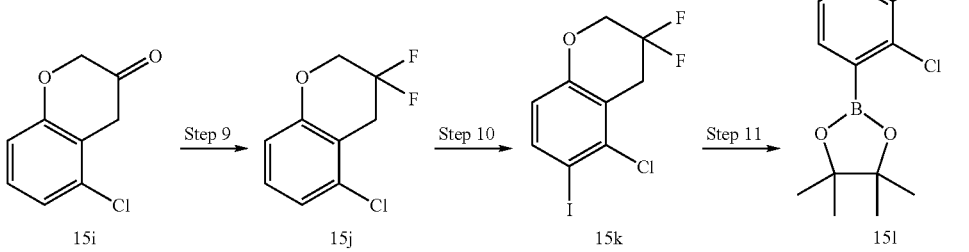

Step 1:
An ethereal solution of diazomethane (0.7 M, 100 mL) is added to a solution of 15a (5.0 g, 30 mmol) in ether (20 mL). After consumption of the SM (TLC monitoring), the reaction is concentrated onto $SiO_2$ (about 10 g) and the product purified by CombiFlash® Companion to yield ester 15b (5.2 g, 95% yield).

Step 2:
A solution of $NaNO_2$ (2.1 g, 30 mmol) in water (10 mL) is slowly added to a solution of aniline 15b (5.0 g, 28 mmol) dissolved in AcOH (50 mL) and 2 M HCl (75 mL) at 0° C. The resulting mixture is stirred at this temperature for 1 h. Solid CuCl (8.4 g, 85 mmol) is added portionwise (over 2 min). The reaction is allowed to come to RT, is stirred for 30 min and then is warmed to 60° C. for 40 min. The mixture is poured into water (200 mL) and extracted with EtOAc (2×200 mL). The organic layer is dried with $MgSO_4$, filtered and evaporated to dryness. The product is purified by CombiFlash® Companion to afford aryl chloride 15c (3.8 g, 68% yield).

Step 3:
A solution of DIBAL in DCM (1 M, 42 mL, 42 mmol) is added dropwise over a period of 25 min to a precooled (−78° C.) solution of ester 15c (3.8 g, 19 mmol) in dry $CH_2Cl_2$ (100 mL). The reaction is allowed to stir for 2 h at −78° C. The reaction is quenched at −78° C. by the dropwise addition of 1 N HCl (8 mL). The reaction is allowed to warm to RT and the organic phase washed with a 5% solution of Rochelle's salt (100 mL), dried over $MgSO_4$, filtered and concentrated under reduced pressure to give crude benzyl alcohol 15d (3.2 g, 99% yield), which is used in the next step without any further purification.

Step 4:
Solid Dess Martin reagent (8.7 g, 20 mmol) is added to a precooled (0° C.) solution of alcohol 15d in dry $CH_2Cl_2$ (100 mL). The reaction is allowed to stir for 2 h while slowly warming to RT. At this time, another 0.5 g of Dess Martin Periodinane is added and the reaction continues for another 1 h. A 1:1 mixture of saturated $NaHCO_3$ and 0.5 M $Na_2S_2O_3$ (100 mL) is added and this mixture is stirred vigorously until the phases become clear (approximately 30 min). The organic phase is separated and the aqueous phase is extracted with DCM (100 mL) and washed with saturated $NaHCO_3$ (100 mL). The combined organic phases are then dried over $MgSO_4$ and evaporated. The product is purified by CombiFlash® Companion to give aldehyde 15e (2.9 g, 90% yield).

Step 5:
A solution of methyl ether 15e (720 mg, 4.2 mmol) in anhydrous $CH_2Cl_2$ (20 mL) is added slowly to a precooled (−30° C.) solution of $BBr_3$ (1 M, 8.4 mL, 8.4 mmol). The solution is warmed to 0° C. and is stirred for 3 h. The reaction is quenched carefully with methanol (1 mL) and washed with saturated $NaHCO_3$ and then brine (25 mL each). The organic layer is dried over $MgSO_4$, filtered and concentrated and the product is purified by CombiFlash® Companion to give phenol 15f (530 mg, 80% yield).

Step 6:
A mixture of the aldehyde 15f (1.1 g, 7.2 mmol), acrylonitrile (2.4 mL, 36 mmol) and DABCO (190 mg, 1.7 mmol) are refluxed for 5 h. The reaction mixture is cooled to RT, diluted with EtOAc (50 mL) and washed with 1 N NaOH (20 mL) and then with 1 N HCl (20 mL). The organic phase is dried over $MgSO_4$ and concentrated to dryness. The product is purified by CombiFlash® Companion to afford the nitrile 15g (650 mg, 47% yield).

Step 7:
A mixture of nitrile 15g (650 mg, 3.4 mmol), 10% NaOH (10 mL, 25 mmol) and EtOH (95%, 0.5 mL) is heated to reflux for 5 days. The reaction is then cooled to RT and 1 N HCl is then added until pH ~4. The precipitate is then collected by filtration, washed with water and dried in vacuo to give acid 15h (740 mg, >99% yield).

Step 8:
Triethylamine (0.56 mL, 4.0 mmol) and diphenylphosphoryl azide (0.75 mL, 3.5 mmol) are added successively to a solution of acid 15h (714 mg, 3.4 mmol) in dry toluene (40 mL). This mixture is heated to 85° C. for 2 h and then cooled to RT and treated with 6 N HCl (6 mL). The mixture is brought to reflux and is stirred at this temperature for 2 h. The reaction is then cooled to RT, diluted with EtOAc (100 mL) and washed with saturated $NaHCO_3$ (2×100 mL), water (2×100 mL) and brine (100 mL). The organic layer is dried over $MgSO_4$, filtered and evaporated to dryness. The product is then purified by CombiFlash® Companion to give ketone 15i (269 mg, 44% yield).

Step 9:
Deoxofluor® (0.54 mL, 2.9 mmol) is added to a solution of ketone 15i (270 mg, 1.5 mmol) in $CH_2Cl_2$ (0.6 mL) and EtOH (17 µL) in a sealed tube. The sealed tube is heated to 40° C. for 24 h. The tube is then unsealed, cooled to 0° C. and the reaction quenched by the slow (Exothermic) addition of saturated $NaHCO_3$ (1 mL). The crude reaction mixture is diluted with water (20 mL) and extracted with DCM (3×20 mL). The combined organics are washed with water (20 mL) and the organic phase is dried over $MgSO_4$, filtered and concentrated. The product is purified by CombiFlash® Companion to provide difluorochroman 15j (225 mg, 71% yield).

Step 10:
Solid silver nitrate (187 mg, 1.1 mmol) and iodine (279 mg, 1.1 mmol) are added successively to a solution of difluorochroman 15j (225 mg, 1.1 mmol) dissolved in MeOH (7.8 mL). The reaction is stirred at RT for 90 min and then filtered through a pad of Celite®. The filtrate is treated with a drop of 0.5 N $Na_2S_2O_3$ (orange color dissipated) then concentrated under reduced pressure. The residue is partitioned between $H_2O$, 0.5N $Na_2S_2O_3$ and EtOAc (20 mL each). The water layer is extracted with EtOAc (3×20 mL) and the combined organics are washed with brine (20 mL), dried over $MgSO_4$, filtered and concentrated. The product is purified by CombiFlash® Companion to give aryl iodide 15k (158 mg, 44% yield).

Step 11:

A solution of the aryl iodide 15k (150 mg, 0.45 mmol), bis[pinocolato]diborane (150 mg, 0.59 mmol) and potassium acetate (130 mg, 1.4 mmol) in DMF (5 mL) is degassed with Ar for 5 min followed by the addition of the PdCl$_2$dppf-DCM complex (44 mg, 0.054 mmol). The reaction mixture is then degassed for an additional 5 min before being heated to 85° C. for 9 h. The reaction is then cooled to RT. The crude reaction mixture is diluted with water and the product is extracted with EtOAc (3×10 mL). The combined organics are washed with water (10 mL) and brine (10 mL). The organic phase is then dried over MgSO$_4$ and filtered and concentrated. The crude mixture is further purified by CombiFlash® Companion to afford boronic ester 15l (123 mg, 70% pure by NMR, 57% yield).

Example 16

Synthesis of Boronate Fragment 16c (Can be Coupled to a Thienopyridine Scaffold to Provide a Compound of the Invention)

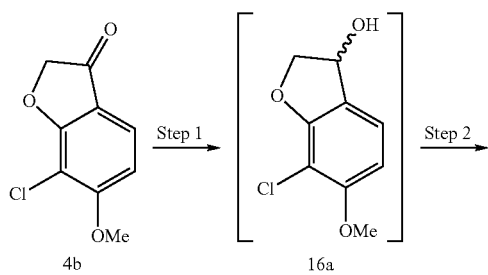

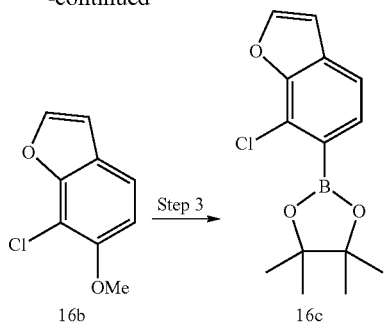

Step 1:
Solid NaBH$_4$ (342 mg, 9.0 mmol) is added to a solution of ketone 4b (1.5 g, 7.5 mmol) dissolved in MeOH (10 mL) and THF (25 mL) at 0° C. is then added. The reaction is warmed to RT and is allowed to stir for 1 h. The reaction is quenched with aqueous HCl (1 N, 5 mL), the MeOH is removed by concentration and the product extracted with EtOAc (2×50 mL). The organic layer is washed with brine (50 mL), dried over Na$_2$SO$_4$, filtered and concentrated to afford alcohol 16a (1.52 g >99% yield). This material is used as is in the next step.

Step 2:
TFA (2.9 mL) is added dropwise to a solution of crude alcohol 16a (1.5 g; 7.47 mmol) in CH$_2$Cl$_2$ (28 mL) at 0° C. The solution is stirred for 30 min, and then concentrated to dryness. The residue is taken up in EtOAc, washed with NaHCO$_3$ (saturated), brine, dried over Na$_2$SO$_4$, filtered and concentrated to a pale yellow gum. The product is purified by CombiFlash® Companion to afford benzofuran 16b (0.30 g, 22% yield) as a white solid.

Step 3:
Compound 16c is prepared from 16b following a synthetic sequence identical to steps 3 to 5 of Example 4.

Example 17

Synthesis of Boronate Fragment 17g (Used for the Preparation of 2016, 2017)

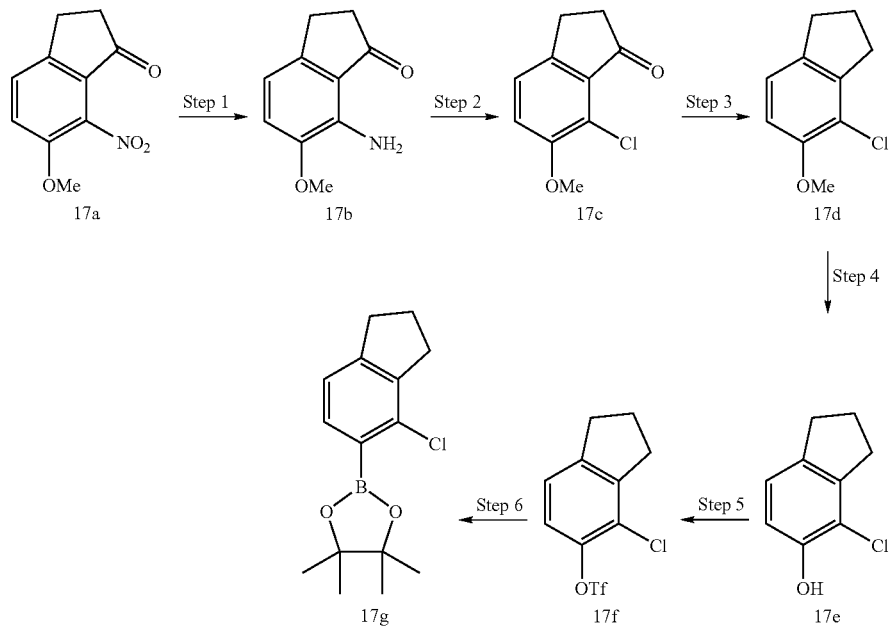

Step 1:

Zn dust (7.89 g, 121 mmol) is added to a solution of 17a (5.0 g, 24 mmol) in AcOH (100 mL). The reaction mixture is then heated to 100° C. and is stirred overnight. The reaction is cooled to RT and the mixture is filtered (EtOAc washing), the solvent is evaporated and the residue purified by CombiFlash® Companion to afford aniline 17b (3.06 g, 72% yield) as a yellow solid.

Step 2:

A solution of NaNO$_2$ (640 mg, 9.3 mmol) in water (3 mL) is slowly added to a solution of aniline 17b (1.5 g, 8.5 mmol) dissolved in AcOH (12 mL) and 2 M HCl (25 mL) at 0° C. The resulting mixture is stirred at this temperature for 1 h Solid CuCl (2.6 g, 26 mmol) is added portionwise (over 2 min) and the reaction is allowed to come to RT, is then stirred for 30 min and then is warmed to 60° C. for 40 min. The mixture is poured into water (100 mL) and extracted with EtOAc (2×100 mL). The organic layer is dried with MgSO$_4$, filtered and evaporated to dryness. The product is purified by CombiFlash® Companion to afford aryl chloride 17c (1.11 g, 99% yield) as a pale yellow solid.

Step 3:

Solid pre-activated Zn dust is added to a solution of ketone 17c in AcOH. The reaction mixture is then heated to 100° C. and stirred at that temperature for 4 h. The reaction mixture is filtered (EtOAc washing), the filtrate is evaporated to dryness and the product purified by CombiFlash® Companion to afford indane 17d (902 mg, 88% yield) as a white crystalline solid.

Step 4:

A solution of BBr$_3$ in DCM (1 M, 9.9 mL, 9.9 mmol) is added dropwise to a precooled (-78° C.) solution of methyl ether 17d (902 mg, 4.9 mmol) dissolved in DCM (20 mL). The reaction solution is stirred at this temperature for 10 min and allowed to warm to RT. After stirring for 1.5 h, water (50 mL) is added (Exothermic) and the mixture is extracted with DCM (3×50 mL). The combined organic layers are dried over MgSO$_4$, filtered and evaporated to dryness. The product is purified by CombiFlash® Companion to afford phenol 17e (700 mg, 84% yield) as an off-white solid.

Step 5:

Tf$_2$O (1.05 mL, 12 mmol) is added to a precooled (0° C.) solution of phenol 17e (700 mg, 4.1 mmol) and Et$_3$N (1.7 mL, 12 mmol) in DCM (20 mL). The resulting dark solution is allowed to warm to RT. After 25 min, the reaction is quenched with saturated NaHCO$_3$ (10 mL), diluted with DCM, and the organic layer washed with water, brine, dried over MgSO$_4$ and evaporated to dryness. The product is purified by CombiFlash® Companion to afford triflate 17f (1.21 g, 97% yield) as a yellow oil.

Step 6:

A solution of triflate 17f (1.2 g, 4.0 mmol), bis[pinocolato] diborane (1.5 g, 6.0 mmol) and potassium acetate (1.3 g, 14 mmol) in DMF (20 mL) is degassed with Ar for 5 min followed by the addition of the PdCl$_2$dppf-DCM complex (490 mg, 0.60 mmol). The reaction mixture is then degassed for an additional 5 min before being heated to 95° C. for 5 h. The reaction is then cooled to RT. The crude reaction mixture is diluted with water and the product is extracted with EtOAc (3×100 mL). The combined organics are washed with water (100 mL) and brine (100 mL). The organic phase is then dried over MgSO$_4$ and filtered and concentrated. The crude mixture is further purified by CombiFlash® Companion to afford boronic ester 17g (593 mg, 53% yield) as a pale yellow solid.

Example 18

Synthesis of Boronate Fragment 18d (Used for the Preparation of 1033)

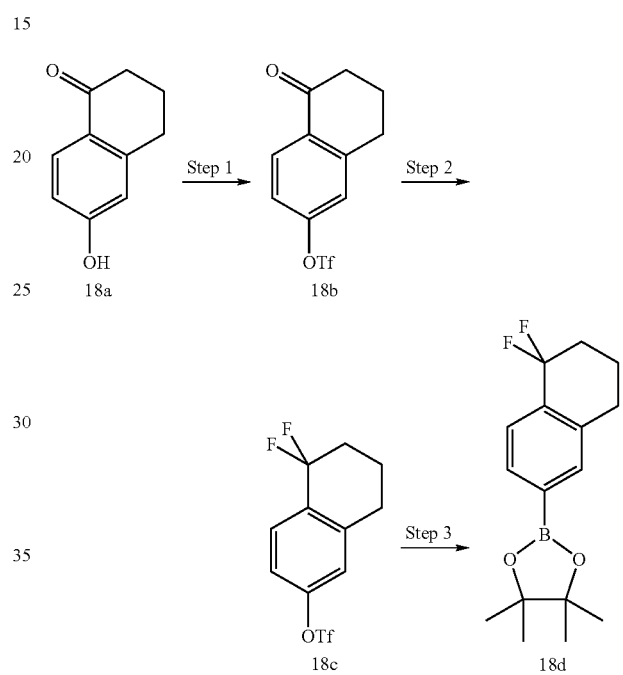

Step 1:

Neat Tf$_2$O (0.83 mL, 4.9 mmol) is added dropwise to a cooled (0° C.) solution of phenol 18a (0.50 g, 3.1 mmol) and pyridine (1.3 mL, 17 mmol) in DCM (15 mL). The reaction is allowed to warm to RT and stir overnight. The reaction is quenched by the addition of a 10% citric acid solution (50 mL) and the mixture is extracted with DCM (3×50 mL). The combined organics are washed with water (50 mL), dried over MgSO$_4$, filtered and concentrated. The product is purified by CombiFlash® Companion to give triflate 18b (500 mg, 94% yield).

Step 2:

Deoxyfluor® (0.83 mL, 4.2 mmol) followed by EtOH (10 µL, 0.2 mmol) are added to neat triflate 18b (500 mg, 1.7 mmol) in a sealable tube. The tube is sealed and the reaction is heated in an oil bath at 85° C. and is stirred overnight. The reaction is then cooled to 0° C. and quenched by the slow addition of NaHCO$_3$ (100 µL, Exothermic). The mixture is diluted with water (50 mL) and extracted with DCM (3×50 mL). The combined organic layers are washed with water (50 mL) and brine (50 mL). The organic phase is then dried over MgSO$_4$, filtered and concentrated. The crude product is purified by CombiFlash® Companion to provide the difluorotetrahydronaphtyl triflate 18c (175 mg, 33% yield).

Step 3:

Step three is performed exactly as in step 6 of Example 17 to provide boronic ester 18d.

Example 19

Synthesis of Boronate Fragment 19d (Used for the Preparation of 1063, 1064, 2044, 2045)

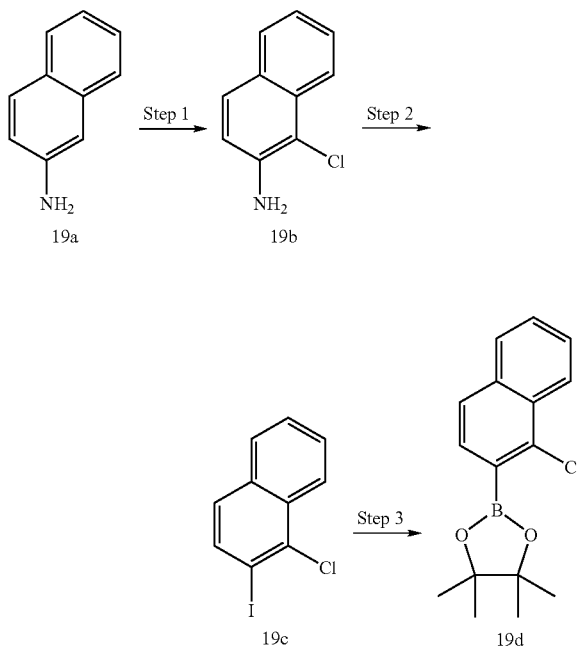

Step 1:

Solid N-chlorosuccinimide (2.2 g, 16 mmol) is added in portions over 5 min to a solution of naphthylamine 19a (2.3 g, 16 mmol) dissolved in $CCl_4$ (150 mL). The reaction is then heated to 50° C. and is stirred for 40 min. The reaction is then cooled to RT, solids are removed by filtration and the filtrate is washed with water (100 mL), dried over $MgSO_4$ and evaporated to dryness to provide chloroaniline 19b (2.8 g, 96% yield).

Step 2:

A solution of $NaNO_2$ (1.2 g, 17 mmol) in water (5 mL) is slowly added to a precooled (0° C.) suspension of aniline 19b (2.8 g, 15 mmol) in 12 N HCl (7 mL) and ice (9.7 g), so as to maintain the temperature below 5° C. The mixture is stirred for 15 min and then is transferred to a solution of KI (8.7 g, 52 mmol) in water (30 mL) and the resulting mixture is stirred for 2 h. The mixture is extracted with $Et_2O$ (3×100 mL) and the combined organic layers washed successively with 3 N NaOH (2×50 mL), 5% $NaHSO_3$ (50 mL) and brine (100 mL). The organic phase is dried over $MgSO_4$, filtered and concentrated to dryness. The crude product is purified by flash chromatography (EtOAc/hexane) to provide aryl iodide 19c (2.4 g, 54% yield).

Step 3:

Step three is carried out exactly as described in step 11 of Example 15 to provide boronic ester 19d.

Example 20

Synthesis of Boronate Fragment 20d (Can be Coupled to a Thienopyridine Scaffold to Provide a Compound of the Invention)

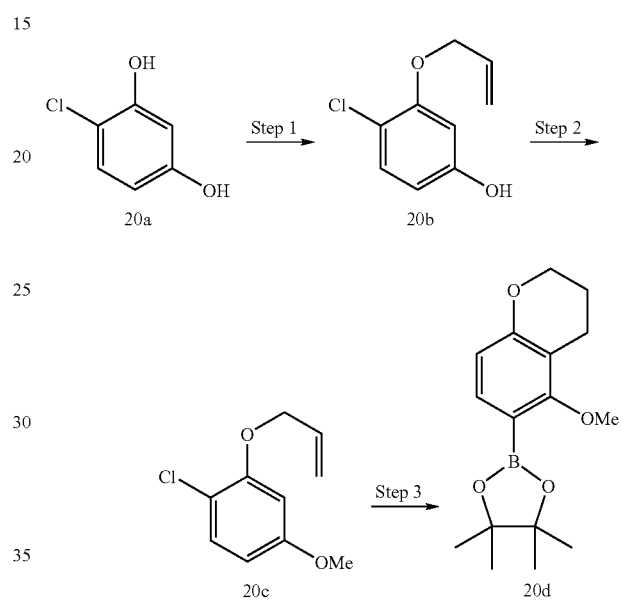

Step 1:

Allyl bromide (2.1 mL, 25 mmol) followed by potassium carbonate (7.2 g, 52 mmol) are added to a solution of 6-chlororesorcinol 20a (10 g, 69 mmol) dissolved in DMF (120 mL). The reaction is stirred overnight, diluted with EtOAc (500 mL) and washed with water (3×500 mL). The organic layer is dried over $MgSO_4$ and concentrated to dryness. The crude product is purified by CombiFlash® Companion to obtain allyl ether 20b (1.8 g, 40% yield).

Step 2:

Methyl iodide (1.2 mL, 20 mmol) followed by potassium carbonate (3.8 g, 27 mmol) are added to a solution of phenol 20b (1.8 g, 9.8 mmol) dissolved in DMF (12 mL). The reaction is stirred for 2 h, diluted with EtOAc (50 mL) and washed with water (3×50 mL). The organic layer is dried over $MgSO_4$ and concentrated to dryness. The crude product is purified by CombiFlash® Companion to obtain methyl ether 20c (1.8 g, 40% yield).

Step 3:

Step 3 is comprised of a sequence of steps identical to steps 2 through 6 of Example 12, followed by step 1 of Example 13 to provide boronic ester 20d.

Example 21

Synthesis of Boronate Fragment 21g (Can be Coupled to a Thienopyridine Scaffold to Provide a Compound of the Invention)

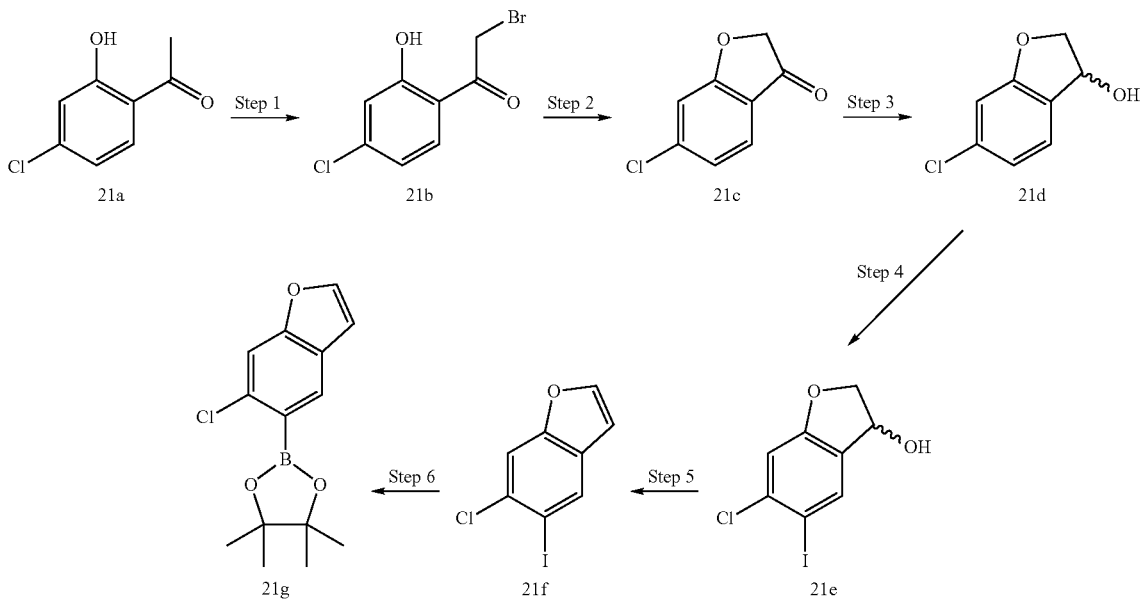

Step 1:

Solid $CuBr_2$ (7.9 g; 35 mmol) is added to a solution of 21a (4.0 g, 23 mmol) dissolved in EtOAc (32 mL) and $CHCl_3$ (32 mL). The mixture is heated to reflux and is stirred for 8 h. $CuBr_2$ (3.9 g, mmol) is then added and the mixture continues to stir at reflux for an additional 15 h. The mixture is cooled to RT, the solids removed by filtration (EtOAc washing). The filtrate is concentrated to afford the crude bromoketone 21b (6.3 g), which is used directly in the next step.

Step 2:

Solid KF (2.5 g, 43 mmol) is added to a solution of crude bromoketone 21b (6.3 g, ~23 mmol) dissolved in DMF (21 mL). The reaction is stirred at RT for 3 h and then taken up in ether (300 mL), washed with brine (3×100 mL), dried over $MgSO_4$, filtered and concentrated to dryness. The crude product is purified by CombiFlash® Companion to afford ether 21c (2.1 g, 49% yield over two steps).

Step 3:

Solid $NaBH_4$ (270 mg, 7.1 mmol) is added to a precooled (0° C.) solution of ketone 21c (1.0 g, 5.9 mmol) dissolved in MeOH (20 mL). The reaction is allowed to stir for 1 h and then quenched with aqueous HCl (1 N, 1 mL). The volatiles are removed in vacuo and the product extracted with EtOAc (1×20 mL). The organic layer is washed with brine (20 mL), dried ($Na_2SO_4$), filtered and concentrated to afford the crude alcohol 21d (1.0 g), which is used directly in the next step.

Step 4:

Solid $AgNO_3$ (1.0 g, 6.1 mmol) followed by $I_2$ (1.6 g, 6.2 mmol) are added to a solution of alcohol 21d (1.0 g, 6.2 mmol) dissolved in MeOH (58 mL). The mixture is stirred at RT for 1 h and then a solution of $Na_2S_2O_4$ (0.5 M, 10 mL) is added and the mixture is stirred for 30 min. The MeOH is removed in vacuo and the residue taken up in EtOAc (50 mL), washed with water (1×50 mL), brine (1×50 mL), dried ($Na_2SO_4$), filtered and concentrated to afford aryl iodide 21e (1.6 g), which is used directly in the next step.

Step 5:

Crude alcohol 21e (1.6 g; ~5 mmol) is dissolved in a mixture of DCM (20 mL) and TFA (2.2 mL). The reaction is stirred for 45 min and then concentrated to dryness. The residue is taken up in EtOAc (50 mL), washed with saturated $NaHCO_3$ (50 mL) and brine (50 mL). The organic layer is dried over $Na_2SO_4$, filtered and concentrated to dryness. The crude product is purified by CombiFlash® Companion to provide benzofuran 21f (978 mg, 65% yield over 3 steps).

Step 6:

Step 6 is carried out exactly as described for step 11 of Example 15 to provide boronic ester 21g.

Example 22

Synthesis of Boronate Fragment 22d (Can be Coupled to a Thienopyridine Scaffold to Provide a Compound of the Invention)

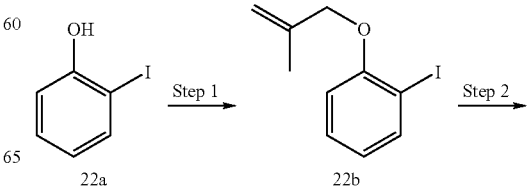

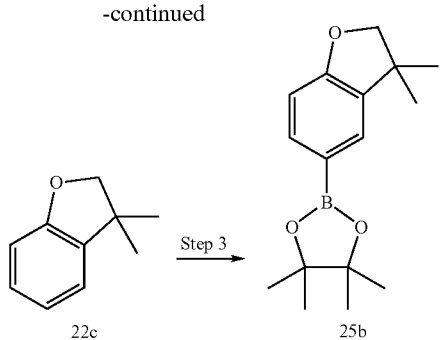

Step 1:

Neat 3-bromo-2-methylpropene (1.7 mL, 16 mmol) is added to a suspension of phenol 22a (3.0 g, 14 mmol) and potassium carbonate (5.6 g, 41 mmol) in DMF (35 mL). The reaction is stirred for 2 h and then quenched with water (100 mL) and extracted with hexanes (2×100 mL). The organic phase is washed with brine (2×100 mL) and concentrated to give ether 22b (3.3 g, 87% yield).

Step 2:

Neat tributyltin hydride (2.3 mL, 8.8 mmol) is added to a solution of aryliodide 22b (2.0 g, 7.3 mmol) and AlBN (120 mg, 0.73 mmol) in PhMe (40 mL) and the reaction is then stirred at reflux under $N_2$. After 1 h, the reaction is concentrated to dryness and the crude product purified by CombiFlash® Companion to provide dihydrobenzofuran 22c (785 mg, 73% yield).

Step 3:

Step 3 is comprised of a sequence of synthetic steps identical to steps 10 and 11 of Example 15 to provide boronic ester 22d.

Example 23

Synthesis of Boronate Fragment 23c (Used for the Preparation of 1025, 1026, 2005, 2006)

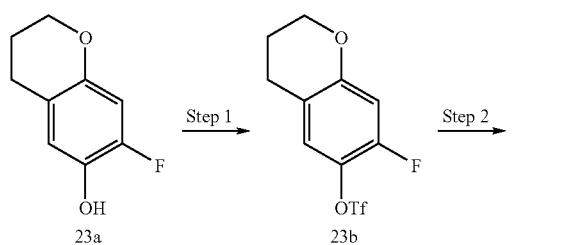

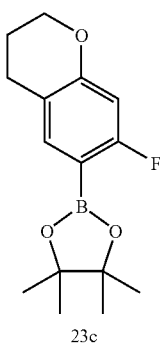

Step 1:

Neat $Tf_2O$ (0.56 mL, 3.3 mmol) is added dropwise to a cooled (0° C.) solution of phenol 23a (350 mg, 2.1 mmol; prepared according to Doi et al *Bull. Chem. Soc. Jpn.* 2004 77, 2257-2263) and pyridine (0.91 mL, 11 mmol) in DCM (10 mL) under an Ar atmosphere. The reaction is allowed to warm to RT and then is stirred for 2 h. The reaction is quenched by the addition of a 10% citric acid solution (20 mL) and extracted with DCM (3×20 mL). The combined organic layers are washed with water (20 mL), dried over $MgSO_4$, filtered and concentrated to dryness. The crude product is purified by CombiFlash® Companion to provide triflate 23b (512 mg, 82% yield).

Step 2:

A solution of the triflate 23b (510 mg, 1.7 mmol), bis[pinocolato]diborane (560 mg, 2.2 mmol) and potassium acetate (500 mg, 5.1 mmol) in DMF (18 mL) is degassed with Ar for 5 min followed by the addition of the $PdCl_2$dppf-DCM complex (140 mg, 0.17 mmol). The reaction mixture is then degassed for an additional 5 min before being heated to 100° C. by microwave irradiation for 10 min. The reaction is then cooled to RT. The crude reaction mixture is diluted with EtOAc (60 mL) and washed with brine (3×60 mL). The organic layer is dried over $MgSO_4$ and filtered and concentrated. The crude mixture is further purified by CombiFlash® Companion to afford boronic ester 23c (200 mg, 42% yield).

Example 24

Synthesis of Boronate Fragment 24b (Can be Coupled to a Thienopyridine Scaffold to Provide a Compound of the Invention)

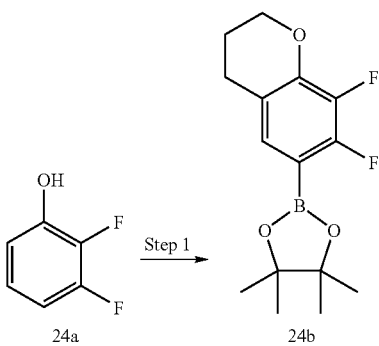

Step 1:

Compound 24b is prepared from 24a following a synthetic sequence identical to steps 1 to 6 of Example 12.

Example 25

Synthesis of Boronate Fragment 25b (Can be Coupled to a Thienopyridine Scaffold to Provide a Compound of the Invention)

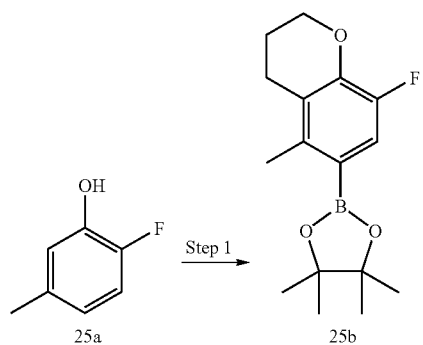

Step 1:

Compound 25b is prepared from 25a following a synthetic sequence identical to steps 1 to 6 of Example 12.

Example 26

Synthesis of Boronate Fragment 26b (Used for the Preparation of 1049, 1050)

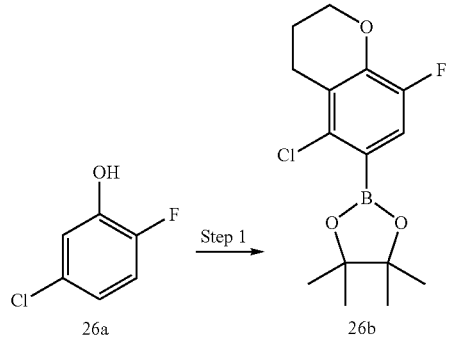

Step 1:

Compound 26b is prepared from 26a following a synthetic sequence identical to steps 1 to 6 of Example 12.

Example 27

Synthesis of Boronate Fragment 27b (Used for the Preparation of 1023, 1024)

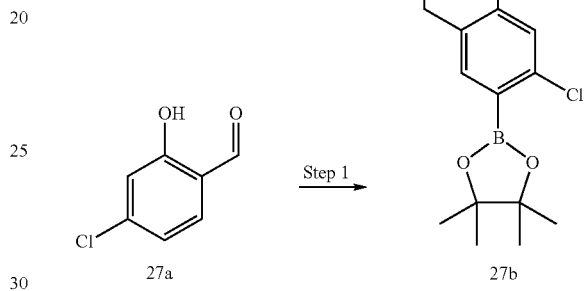

Step 1:

Compound 27b is prepared from 27a following a synthetic sequence identical to steps 1 to 6 of Example 14.

Example 28

Synthesis of Boronate Fragment 28b (Can be Coupled to a Thienopyridine Scaffold to Provide a Compound of the Invention)

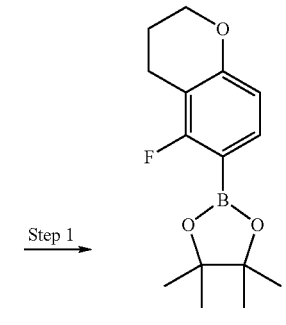

Step 1:

Compound 28b is prepared from 28a following a synthetic sequence identical to steps 1 to 8 of Example 6.

Example 29

Synthesis of Boronate Fragment 29b (Can be Coupled to a Thienopyridine Scaffold to Provide a Compound of the Invention)

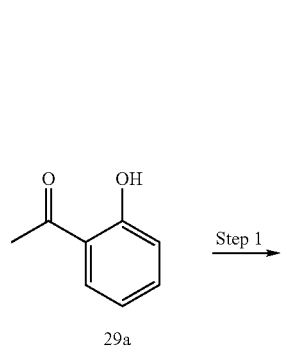

Step 1:

Compound 29b is prepared from 29a following a synthetic sequence identical to steps 1 to 6 of Example 14.

Example 30

Synthesis of Boronate Fragment 30b (Can be Coupled to a Thienopyridine Scaffold to Provide a Compound of the Invention)

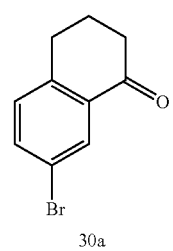

Step 1:

Compound 30b is prepared from 30a following a synthetic sequence identical to steps 2 and 3 of Example 18.

Example 31

Synthesis of Boronate Fragment 31b (Can be Coupled to a Thienopyridine Scaffold to Provide a Compound of the Invention)

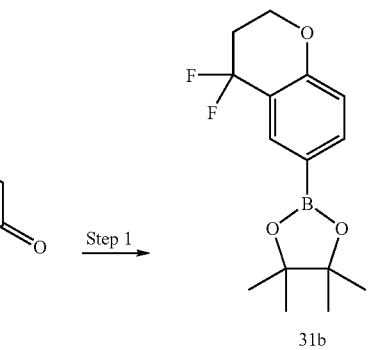

Step 1:

Compound 31b is prepared from 31a following a synthetic sequence identical to steps 9 to 11 of Example 15.

Example 32

Synthesis of Boronate Fragment 32b (Used for the Preparation of 1020)

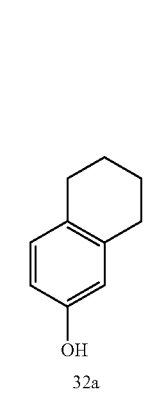 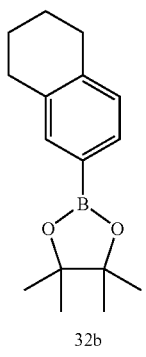

Step 1:
  Compound 32b is prepared from 32a following a synthetic sequence identical to steps 5 to 6 of Example 17.

Example 33

Synthesis of Boronate Fragment 33b (Used for the Preparation of 1021)

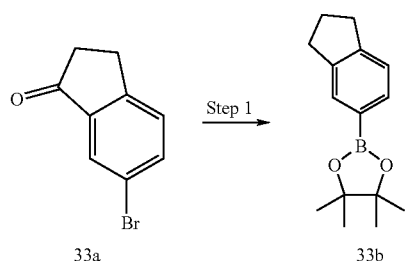

Step 1:
  Compound 33b is prepared from 33a following a synthetic sequence identical to steps 1 and 3 of Example 11.

Example 34

Synthesis of Boronate Fragment 34f (Can be Coupled to a Thienopyridine Scaffold to Provide a Compound of the Invention)

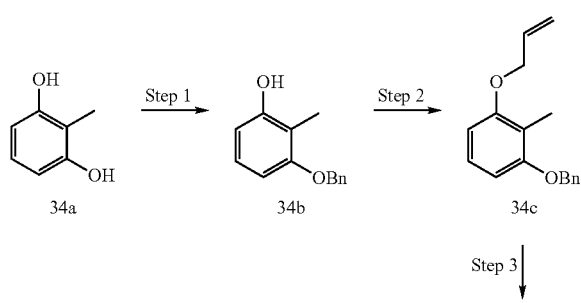

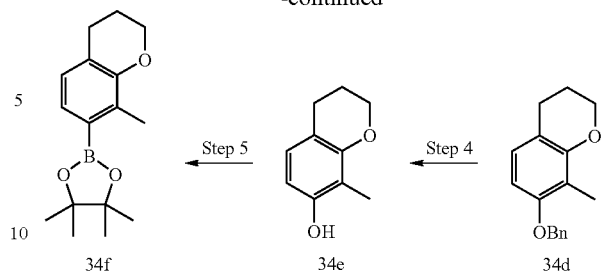

Step 1:
  Benzyl bromide (25 mL, 210 mmol) followed by potassium carbonate (44 g, 320 mmol) are added to a solution of 2-methylresorcinol 34a (38 g, 310 mmol) dissolved in DMF (1 L). The reaction is stirred overnight, diluted with EtOAc (2 L) and washed with water (3×2 L). The organic layer is dried over $Na_2SO_4$ and concentrated to dryness. The crude product is purified by CombiFlash® Companion to obtain benzyl ether 34b (18.6 g, 39% yield).

Step 2:
  Allyl bromide (3.0 mL, 35 mmol) followed by potassium carbonate (6.5 g, 47 mmol) are added to a solution of phenol 34b (5 g, 23 mmol) dissolved in DMF (100 mL). The reaction is stirred overnight, diluted with EtOAc (500 mL) and washed with water (3×500 mL). The organic layer is dried over $Na_2SO_4$ and concentrated to dryness. The crude product is purified by CombiFlash® Companion to obtain benzyl ether 34c (4.4 g, 75% yield).

Step 3:
  Compound 34d is prepared from 34c following a synthetic sequence identical to steps 2 to 4 of Example 12.

Step 4:
  Benzyl ether 34d and Pd—C (10% w/w, 100 mg, 0.094 mmol) are combined in EtOAc (5 mL) and the flask is evacuated and backfilled with a $H_2$ atmosphere (balloon). After stirring for 3 h, the reaction is filtered through Celite® (EtOAc washing) and the filtrated concentrated to give phenol 34e (145 mg, 95% yield).

Step 5:
  Compound 34f is prepared from 34e following a synthetic sequence identical to steps 5 to 6 of Example 17.

Example 35

Synthesis of Boronate Fragment 35e (Can be Coupled to a Thienopyridine Scaffold to Provide a Compound of the Invention)

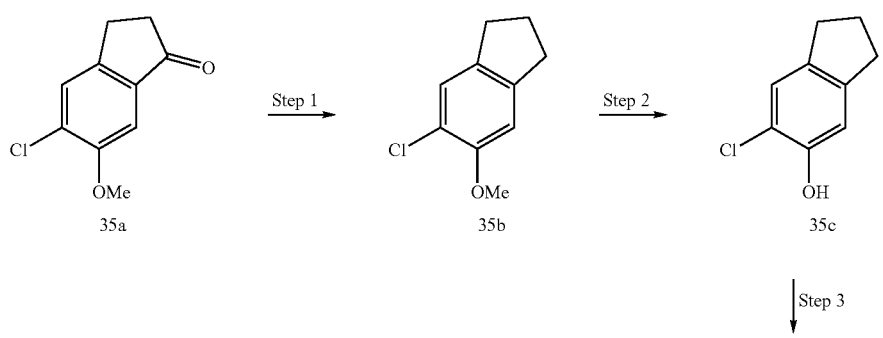

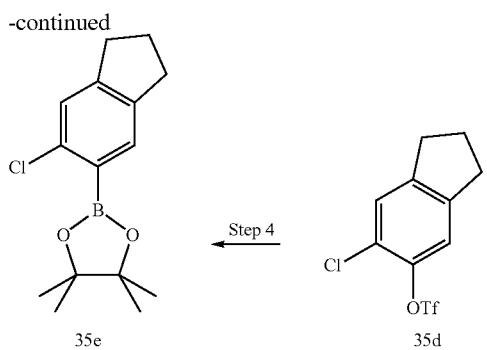

Steps 1 through 4 are done in analogy to steps 3 through 6 from Example 17.

Example 36

Synthesis of Boronate Fragment 36d (Used for the Preparation of 1034, 1035, 2018, 2022)

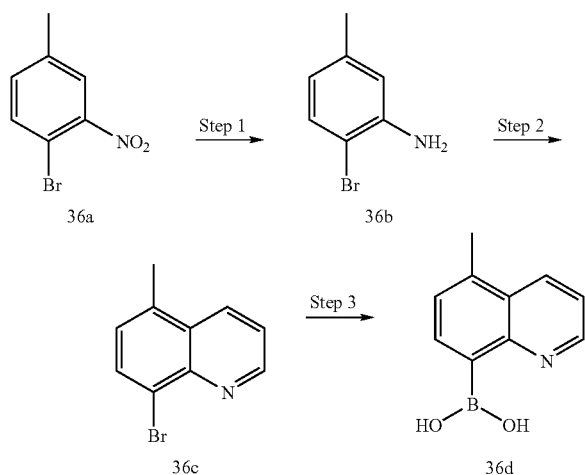

Step 1:

4-bromo-3-nitrotoluene 36a (5.0 g, 22.9 mmol) is dissolved in ethyl acetate (50 mL) and solid tin(II) chloride dihydrate (20.0 g, 86.9 mmol) is added. The mixture is heated under nitrogen atmosphere at 70° C. for 2 h (note: temporary overheating to 100° C. is observed) The mixture is cooled down and is poured into ice-water (200 mL). 5% aqueous NaHCO$_3$ (50 mL) solution is added (rapid foaming), followed by 10 N aqueous NaOH to bring the pH ~7-8. Large volume of gelatinous yellowish precipitate is formed. This heterogeneous mixture is shaken with EtOAc (200 mL) and the mixture is centrifuged in 50 mL portions, resulting in good separation of a yellowish solid. The clear supernatant is decanted and is extracted with EtOAc. Combined organic phase is washed with brine, dried over sodium sulphate, filtered and concentrated under vacuum to give an orange oily residue. This residue is re-dissolved in 100 mL of ether and the solution is washed with 10% Na$_2$CO$_3$ (20 mL) followed by 2.5 M aqueous NaOH (20 mL). The dark brown organic solution is then stirred with MgSO$_4$ and active charcoal and filtered to give a light yellow solution, which darkened rapidly on standing in open flask. The solvent is removed under vacuum to give the desired compound 36b as a brown-red oil which is used in the next step without further purification (3.31 g, 78% yield).

Step 2:

A mixture of compound 36b (3.3 g, 17.7 mmol), glycerin (3.3 g, 35.5 mmol), nitrobenzene (2.2 g, 17.7 mmol) and 75% aqueous sulfuric acid (10 mL, 138 mmol) is stirred at 150° C. for 3 h (mixture turns black and viscous). The reaction mixture is cooled down, poured into ice-water (200 mL) and 10 N aqueous NaOH is added (30 mL, 300 mmol). The black mixture is then shaken with EtOAc (100 mL) and is centrifuged in 50 mL portions. The upper EtOAc layers are combined and the bottom aqueous layers containing the black tar are shaken with EtOAc and re-centrifuged. All EtOAc extracts are combined, washed with brine, dried over Na$_2$SO$_4$, filtered and concentrated under vacuum to give 4.8 g of a brown-red oil. This material is chromatographed on 80 g silica gel column (CombiFlash® Companion apparatus, hexanes/EtOAc gradient). The fractions containing the compound are concentrated under vacuum to afford compound 36c as a white solid (3.26 g, 83% yield).

Step 3:

To a cooled (~78° C.) solution of compound 36c (500 mg, 2.25 mmol) in anhydrous Et$_2$O (20 mL), is added over 5 min under an Ar atmosphere a 1.6 M solution of n-BuLi in hexane (3.5 mL, 5.60 mmol). The mixture is stirred at −78° C. for 50 min, triisopropylborate (2.00 mL, 8.55 mmol) is then added dropwise and the mixture is stirred for about 2 h at that temperature. The mixture is slowly allowed to reach RT over a 2 h period and it is poured into 1 M aqueous HCl (30 mL). The mixture is transferred into a separatory funnel, the organic layer is separated and the aqueous layer is washed with Et$_2$O. The aqueous layer is then transferred into a 500 mL Erlenmeyer flask and the pH of the solution is adjusted to approximately 6.3 (measured with a pH meter) by slowly adding a saturated solution of NaHCO$_3$ in water (~25 mL, careful: foaming). The suspension is filtered off and the separated light-beige solid is washed with water and dried under high vacuum. This crude product (383 mg) is triturated with Et$_2$O/hexanes to give a first crop of the desired compound 36d as a free base (120 mg, 28% yield). The mother liquors are concentrated under vacuum and are purified by reversed-phase HPLC using a CH$_3$CN/H$_2$O gradient containing 0.06% TFA (ODS-AQ, C-18 column, 75×30 mm, 5-µm particle size). After lyophilization, a second crop of compound 36d is obtained as a TFA salt (102 mg, 15% yield), (total yield: 43%).

Example 37

Synthesis of Boronate Fragment 37d (Used for the Preparation of 1036, 2019, 2023)

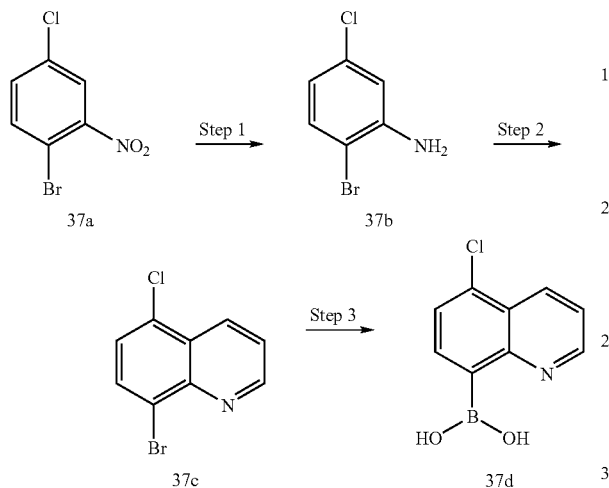

Step 1:

1-bromo-4-chloro-2-nitrobenzene 37a is transformed to compound 37b using the procedure of example 36b, except for the fact that $Et_2O$ is used for the extractions instead of EtOAc.

Step 2:

Compound 37b (4.2 g, 20.3 mmol) is melted at 50° C. in a 100 mL round-bottomed flask containing a stirring bar and immersed in an oil bath. A solution of zinc chloride (700 mg, 5.03 mmol) and ferric chloride (540 mg, 3.25 mmol) in 3.3 mL of water is added in one portion followed by 20 mL of absolute EtOH. The flask is stoppered with a rubber septa and a needle is inserted to avoid any pressure build-up. The mixture is warmed to 80° C. and acrolein (1.68 mL, 24.4 mmol) is added via a syringe pump over a 2 h period. After the addition, the mixture is stirred at 80° C. for 1 h and an additional amount of solid ferric chloride is added (4.1 g, 25.3 mmol). The mixture is stirred at 80° C. for about an extra 24 h and then concentrated under vacuum to give a semi-solid residue. 200 mL of water is added followed by a 10 N aqueous solution of NaOH (20 mL) and 200 mL of DCM. After shaking the mixture for a few min, the solid is filtered over a pad of Celite® and the filtrate is transferred into a separatory funnel. The organic layer is separated and the aqueous layer is extracted with DCM. The combined organic extracts are washed with brine, dried ($Na_2SO_4$), filtered and concentrated under vacuum to give 3.69 g of a brown solid. This solid is triturated in hot $CH_3CN$ and filtered. The solid is discarded and the filtrate is concentrated under vacuum to give 2.3 g of a brown semi-solid. This material is purified on a Combi-Flash® Companion apparatus on 40 g silica gel column eluted with EtOAc/hexanes gradient. After evaporation of the solvent under vacuum, the desired compound 37c is isolated as a yellow solid (390 mg, 8% yield).

Step 3:

Compound 37c is transformed to compound 37d using the procedure of example 36d.

Example 38

Synthesis of Boronate Fragment 38c (Can be Coupled to a Thienopyridine Scaffold to Provide a Compound of the Invention)

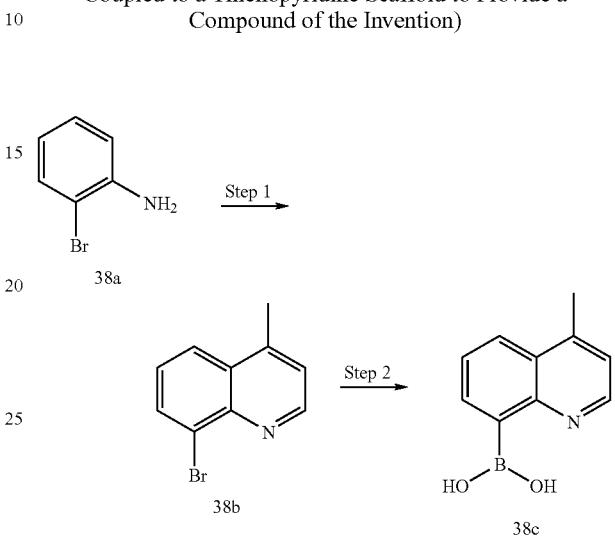

Step 1:

2-bromoaniline 38a is transformed to compound 39b using the procedure of example 37c except that methyl vinyl ketone is used instead of acrolein.

Step 2:

Compound 38b is transformed to compound 38c using the procedure of example 36d.

Example 39

Synthesis of Boronate Fragment 39k (Used for the Preparation of 1059, 1060, 2035, 2036)

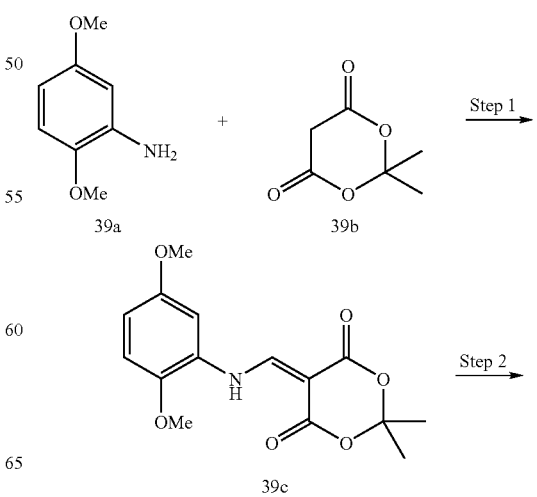

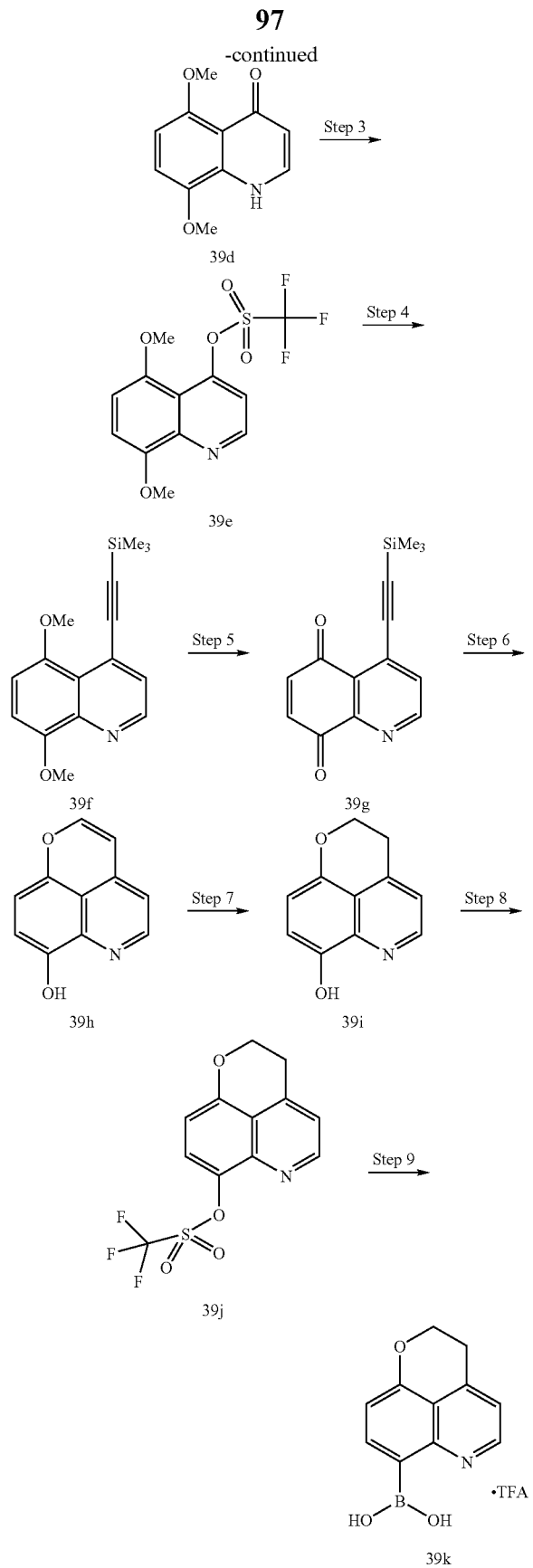

Reference: Feliu, L.; Ajana, W.; Alvarez, M.; Joule, J. A. *Tetrahedron* 1997, 53, 4511.

Step 1:

Meldrum's acid 39b (47.04 g, 326 mmol) is dissolved in trimethyl orthoformate (360 mL) and refluxed for 2 h. Then 2,5-dimethoxy aniline 39a (50 g, 326 mmol) is added and the mixture is refluxed for 5 h. The reaction mixture is cooled down to RT and the solid which formed upon cooling is collected by filtration. It is further crystallized from MeOH to afford compound 39c as a yellow solid (63 g, 63% yield).

Step 2:

Compound 39c (62.00 g, 202 mmol) is dissolved in diphenyl ether (310 mL) and refluxed at 240° C. for 30 min. The mixture is then cooled down to RT and n-hexane is added, which causes a brown precipitate to form. This solid is separated by filtration and is washed with n-pentane and n-hexane to remove non-polar impurities and the remaining dark brown solid (compound 39d) is used as is in the next step (27 g, 65% yield).

Step 3:

A mixture of compound 39d (30.0 g, 146 mmol), DMAP (3.75 g, 30.7 mmol) and 2,6-lutidine (24.4 mL, 208 mmol) in DCM (1.4 L) is cooled to 0° C. and $Tf_2O$ (29.6 mL, 175 mmol) is added slowly at 0° C. The resulting mixture is stirred at 0° C. for 2 h and at RT for 1 h. It is then diluted with $CH_2Cl_2$, washed with $H_2O$ and brine and dried ($Na_2SO_4$). The solvent is removed under reduced pressure and the residue is purified by flash chromatography on silica gel (20% EtOAc/petroleum ether). The desired compound 39e is isolated as a yellow solid (35 g, 70% yield).

Step 4:

A mixture of diisopropylethyl amine (46.5 mL, 267 mmol) in dry DMF (250 mL) is degassed with argon for 30 min and is added to a mixture of compound 39e (30.0 g, 89.0 mmol), triphenylphosphine (7.70 g, 29.4 mmol), tris(dibenzylideneacetone)di-palladium(0)-chloroform adduct (9.21 g, 8.9 mmol). The resulting mixture is stirred for 5 min at 0° C. and TMS-acetylene (13.4 g, 136 mmol) is added dropwise. The temperature is raised to RT and the mixture is stirred for 4 h. Diethyl ether and water is added, the aqueous layer is separated and washed with diethyl ether. The combined organic layers are washed with $H_2O$ and brine. After drying on $Na_2SO_4$, the solvent is removed under reduced pressure and the residue is purified by flash chromatography on silica gel (30% EtOAc/petroleum ether). Compound 39f is isolated as a yellow solid (18 g, 70% yield).

Step 5:

A solution of ceric ammonium nitrate (42.3 g, 77.2 mmol) in $H_2O$ (47 mL) is added under argon atmosphere to a solution of compound 39f (11.0 g, 38.3 mmol) in acetonitrile (366 mL). The reaction mixture is degassed with argon for 10 min and the mixture is stirred at RT for 20 min. Water is then added and the solution is extracted with $CH_2Cl_2$. The organic extracts are combined, washed with $H_2O$, brine and dried ($Na_2SO_4$). The solvent is removed under reduced pressure and the residue is purified by flash chromatography on silica gel (40% EtOAc/petroleum ether). The desired compound 39g is isolated as a yellow solid (5.0 g, 52% yield).

Step 6:

Compound 39g (1.80 g, 7.1 mmol) is taken in distilled acetic acid (72 mL) under argon atmosphere. Ammonium chloride (7.55 g, 141 mmol) is added and the reaction is refluxed for 45 min. The reaction mixture is cooled to RT, $H_2O$ is added and the solution is washed with EtOAc. The aqueous layer is neutralized with a saturated aqueous solution of $NaHCO_3$ and is extracted with EtOAc. The combined organic extracts are washed with $H_2O$, brine and dried ($Na_2SO_4$). The solvent is removed under reduced pressure to afford compound 39h as a brown solid (250 mg, 20% yield).

Step 7:

Compound 39h (230 mg, 1.24 mmol) is dissolved in absolute EtOH (11 mL) and 10% palladium on carbon is added (46 mg) under nitrogen atmosphere. The mixture is stirred for 15 h under one atmosphere of hydrogen. The reaction is degassed with nitrogen, filtered through Celite®, and the Celite® bed is washed with an EtOH—CHCl$_3$ mixture. The solvent is removed under reduced pressure to give compound 39i as a brown sticky solid (200 mg, 86% yield).

Step 8:

Compound 39i (600 mg, 3.21 mmol) is taken in dry CH$_2$Cl$_2$ (30 mL) under nitrogen atmosphere. The solution is cooled to 0° C. and triethylamine (0.89 mL, 6.42 mmol) is added dropwise followed by Tf$_2$O (0.65 mL, 3.87 mmol). The temperature is raised to RT and the reaction mixture is stirred for 2 h. The mixture is diluted with CH$_2$Cl$_2$ and is washed with H$_2$O, brine and dried (Na$_2$SO$_4$). The solvent is removed under reduced pressure to afford a residue which is purified by flash chromatography (10% EtOAc/hexane). Compound 39j is isolated as a brown solid (630 mg, 61% yield).

Step 9:

In a dry (oven-dried for 30 min.) 5-mL glass microwave vessel containing a magnetic stirring bar, are added compounds 39j (250 mg, 0.078 mmol), bis(pinacolato)diborane (250 mg, 0.098 mmol), anhydrous potassium acetate (150 mg, 1.51 mmol), Pd(PCy$_3$)$_2$ (62.0 mg, 0.091 mmol) and anhydrous deoxygenated (argon bubbling for 30 min) 1,4-dioxane (4 mL). The vial is capped tightly with a septum-cap and the vessel is flushed with argon. The mixture is stirred at 95° C. (oil bath temperature) under an atmosphere of argon for 16 h. The reaction mixture is then concentrated under vacuum, the brown oily residue is dissolved in 7 mL of glacial AcOH and is filtered via 45 μm membrane filter. The dark brown solution is divided into 5×1.5 mL portions and is injected on an automatic preparative reversed-phase HPLC-MS apparatus (CH$_3$CN/H$_2$O gradient containing 0.06% TFA, ODS-AQ, C-18 column, 50×19 mm, 5-μm particle size). The collected fractions are lyophylized to give the desired compound 39k as a yellow amorphous solid (115 mg, 45% yield for the TFA salt).

Example 40

Synthesis of Compounds 1030 and 1031

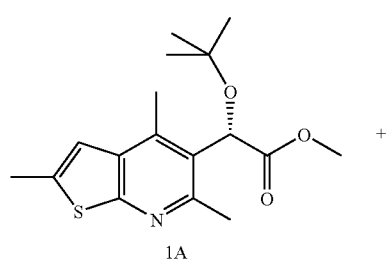

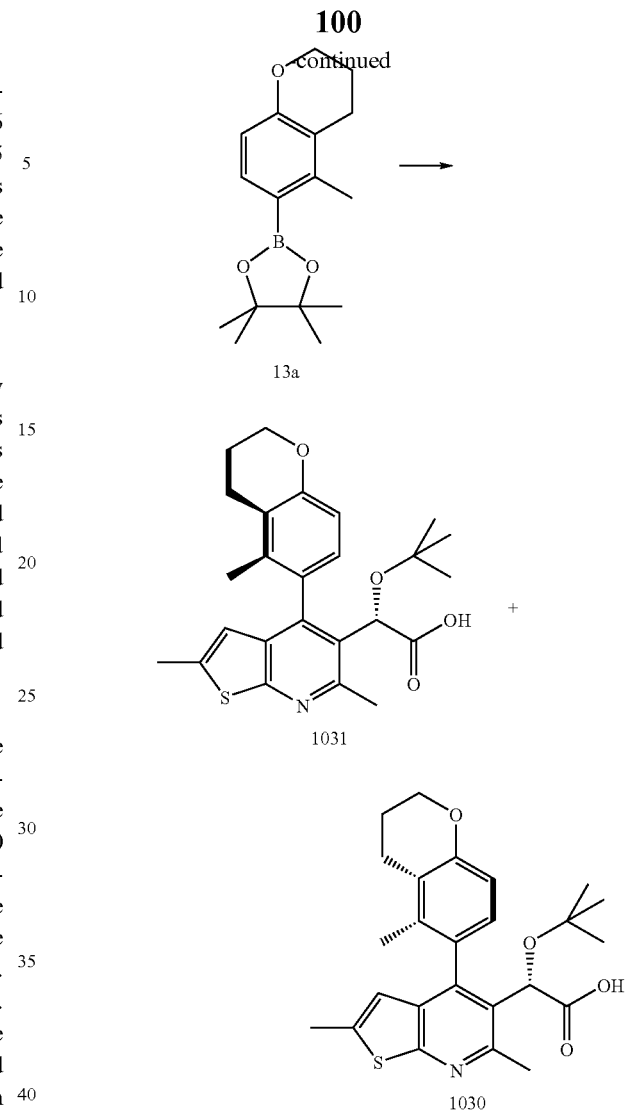

To a microwavable vessel is added the thienopyridine scaffold 1A (69 mg, 0.16 mmol), potassium carbonate (66 mg, 0.47 mmol) and the boronate 13a (52 mg, 0.19 mmol) in DMF (2.2 mL) and water (0.22 mL). To this mixture, the catalyst Pd(PPh$_3$)$_4$ (18.3 mg, 0.02 mmol) is added before the vessel is sealed and then heated at 120-° C. for 8 min. The cooled reaction mixture is partitioned between EtOAc and water. The organic phase is washed with brine, dried over anhydrous MgSO$_4$, filtered and concentrated to dryness. The crude material is absorbed onto SiO$_2$ and purified by combi-flash (EtOAc/hexanes) to afford a mixture of atropisomers (62.4 mg, 0.14 mmol, 87% yield). To a solution of this mixture (62.4 mg, 0.14 mmol) in THF (3 mL) and MeOH (2 mL) at RT is added aqueous LiOH (1 N solution, 0.69 mmol). The reaction is heated to 50° C. for 4 h. The mixture is quenched by addition of AcOH before concentration under vacuum. The two compounds (1030 and 1031) are separated by preparative reversed phase HPLC and then lyophilized to give inhibitor 1031 (12.9 mg, 21% yield) and 1030 (1.7 mg, 3% yield) as white solids.

Example 41

Synthesis of Compounds 1053 and 1054

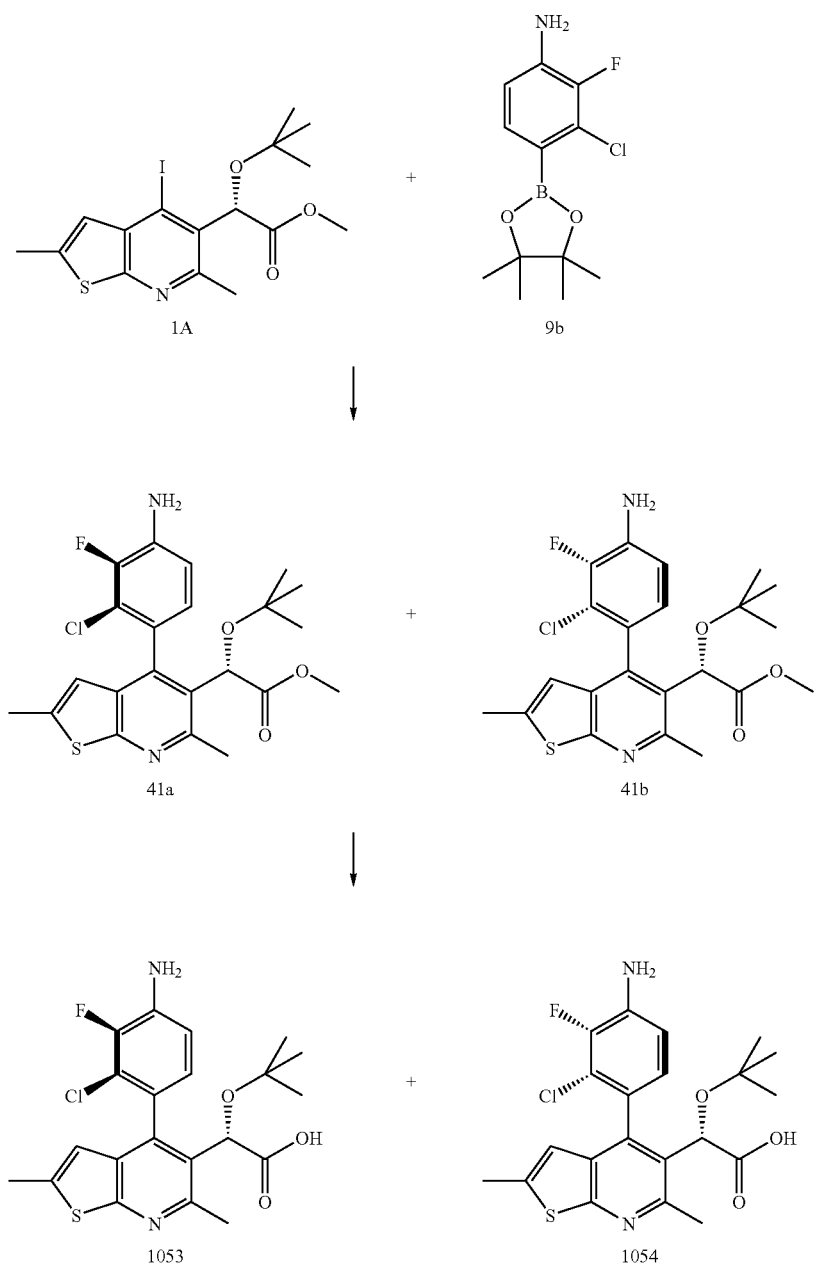

N,N-dimethylformamide (10 mL) and distilled water (2.0 mL) are added to a microwave vial each charged with boronate 9b (614 mg; 2.26 mmol), thienopyridine scaffold 1A (700 mg; 1.61 mmol), potassium carbonate (669 mg; 4.84 mmol) and Pd(PPh$_3$)$_4$ (280 mg; 0.243 mmol), and the vial then is sealed and heated in a microwave reactor (10 min, 140° C.). The resulting mixture is cooled and extracted with EtOAc (200 mL) and washed with half-saturated aqueous sodium bicarbonate (200 mL) and brine (200 mL). The extract is dried over anhydrous MgSO$_4$, filtered and evaporated to a red syrup which is chromatographed over silica gel (EtOAc/hexanes) to afford a mixture of atropisomeric esters 41a and 41b (504 mg; 69% yield) as a pale yellow amorphous solid. A portion of this mixture (120 mg; 0.266 mmol) is dissolved in THF (3.0 mL) and MeOH (1.5 mL), 1.0 N NaOH solution is added (1.0 mL; 1.0 mmol) and the reaction then is heated to 50° C. After 16 h, the reaction is cooled, acidified to pH ~5 using 1.0 N HCl and extracted with DCM. The extract is dried over MgSO$_4$, filtered and evaporated. The residue was purified by reversed phase prep HPLC and lyophilized to yield final compounds 1053 (26 mg; 46% yield) and 1054 (11 mg; 19% yield) as pale yellow powders.

Example 42

Synthesis of Alkyne 42a

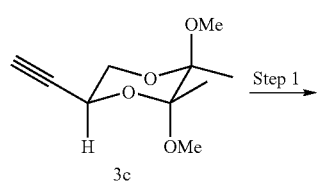

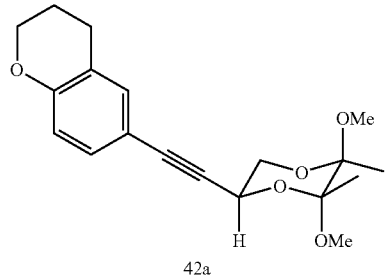

Step 1:

Solid Pd(PPh₃)₄ (444 mg, 0.385 mmol) and CuI (146 mg, 0.769 mmol) are successively added to a solution of 11c (10 g, 34 mmol) and alkyne 3c (11 g, 55 mmol) dissolved in DMF (23 mL) and diethylamine (115 mL). The reaction mixture is stirred overnight at RT and then concentrated, diluted with EtOAc (300 mL) and successively washed with brine, 1 N aqueous HCl and water (300 mL each). The organic layer is dried over Na₂SO₄ and the residue purified by CombiFlash® Companion to give alkyne 42a (10.8 g, 84% yield).

Example 43

Synthesis of Compound 2028

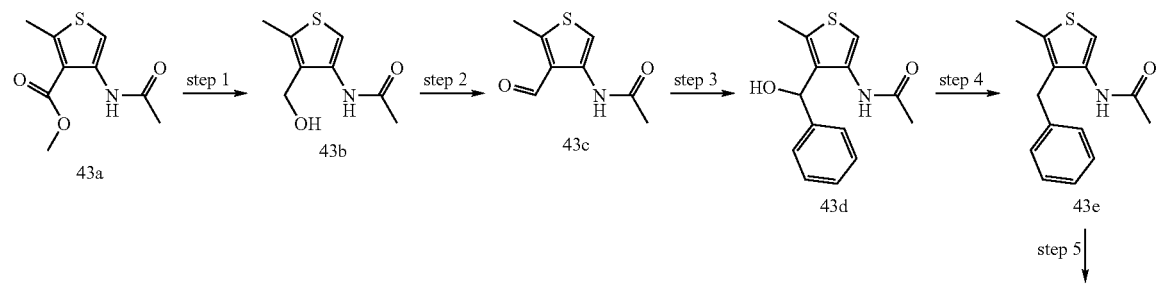

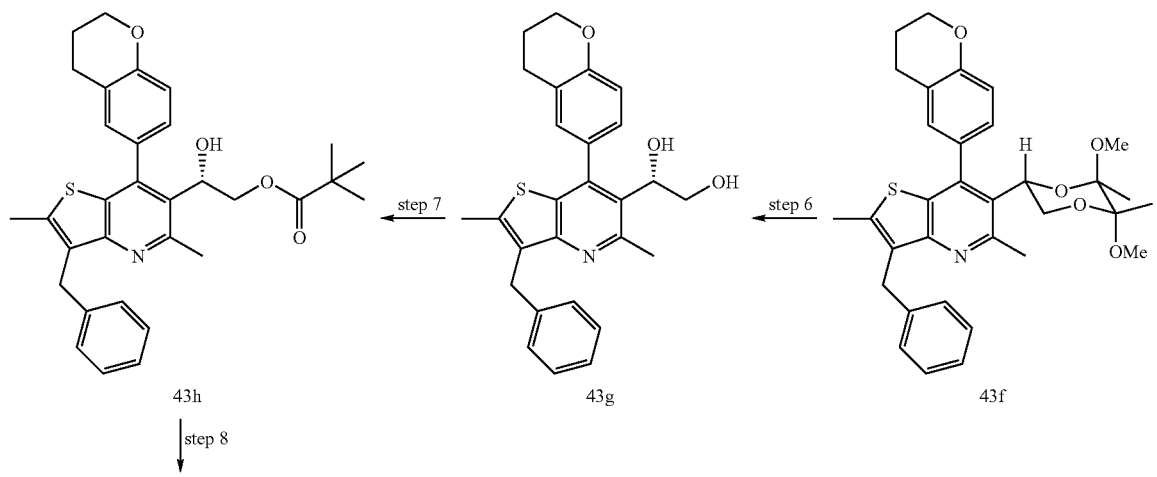

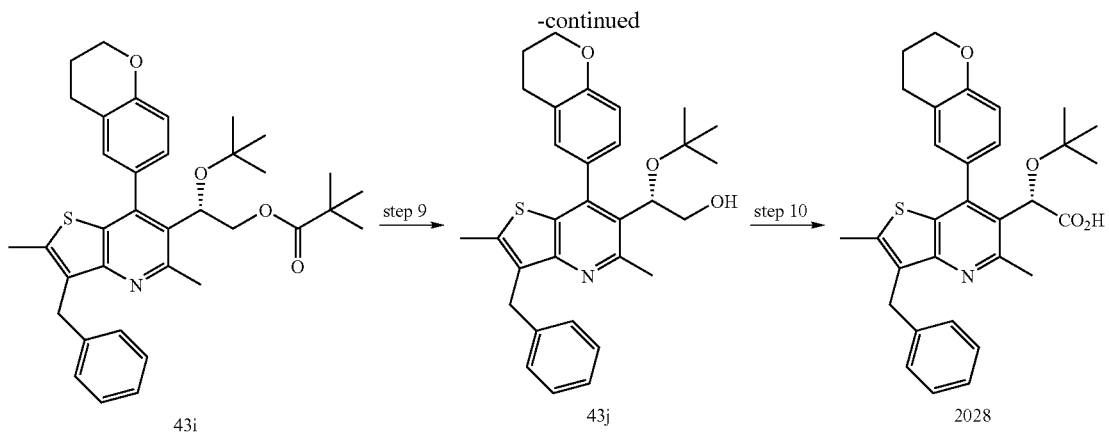

Step 1:
LiBH$_4$ in THF (2 M, 8.7 mL, 17 mmol) is added to a solution of 43a (379 mg, 1.78 mmol) dissolved in THF (7.6 mL) and the reaction is stirred at RT. After 3 h, excess reagent is quenched with HCl (slow addition (CAUTION, Effervescence), 10 mL) and the mixture partitioned between brine (50 mL) and EtOAc (50 mL). The water layer is washed with EtOAc (2×50 mL) and the combined organic layers are dried over Na$_2$SO$_4$ and concentrated. The residue is purified by CombiFlash® Companion to give alcohol 43b (164 mg, 50% yield).

Step 2:
Solid Dess-Martin periodinane (434 mg, 1.03 mmol) is added to a solution of alcohol 43b (145 mg, 0.78 mmol) dissolved in DCM (6 mL). After stirring for 20 min, the reaction is quenched with 20 mL of a 1:1 mixture of saturated NaHCO$_3$ and saturated NaS$_2$O$_3$ and this mixture is then stirred for approximately 15 min (until both phases are clear). The mixture is extracted with EtOAc (2×50 mL) and organic layers are dried over Na$_2$SO$_4$ and concentrated to give aldehyde 43c (125 mg, 87% yield).

Step 3:
Phenyl magnesium bromide (1 M, 1.3 mL, 1.3 mmol) is added dropwise to a solution of aldehyde 43c (125 mg, 0.68 mmol) dissolved in THF (12 mL) at RT. After 5 min, the reaction is quenched by addition of HCl (1 mL, 10%) and water (50 mL) and extracted with EtOAc (3×50 mL). The combined organic layers are dried over Na$_2$SO$_4$ and concentrated to give alcohol 43d (180 mg, quantitative yield).

Step 4:
Zn dust (875 mg, 13.4 mmol) is added to a solution of alcohol 43d (140 mg, 0.54 mmol) dissolved in AcOH (2.1 mL) and the reaction is sealed in a Schlenck tube, heated to 100° C. and stirred vigourously at this temperature. After stirring overnight, the reaction is filtered cooled to RT, filtered through Celite® (AcOH wash), diluted with 4 volumes of PhMe and evaporated to dryness. The residue is purified by CombiFlash® Companion to give thiophene 43e (69 mg, 53% yield).

Step 5:
Tf$_2$O (52 μL, 0.31 mmol) is added via syringe over 1 min to a stirred mixture of amide 43e (69 mg, 0.28 mmol) and 2-chloropyridine (32 μL, 0.34 mmol) in DCM (0.75 mL) at −78° C. After 5 min, the reaction flask is placed in an ice-water bath and warmed to 0° C. Alkyne 42a (187 mg, 0.56 mmol) in DCM (1 mL) is added via syringe. The resulting solution is allowed to warm to RT. After stirring for 30 min, Et$_3$N (1 mL) is added and the mixture partitioned between DCM (50 mL) and brine (50 mL). The organic layer is washed with brine (50 mL), dried over Na$_2$SO$_4$ and concentrated. The residue is then purified by CombiFlash® Companion giving thienopyridine 43f (105 mg, 87% pure, 59% yield).

Step 6:
Thienopyridine 43f (40 mg, 0.071 mmol) is dissolved in TFA/water (10:1, 1.1 mL) and the reaction is stirred at RT. After 30 min, the reaction is reduced under pressure, diluted with saturated NaHCO$_3$ (5 mL) and extracted with DCM (3×10 mL). The combined organic layers are dried over Na$_2$SO$_4$ and concentrated to give diol 43g (30 mg, 94% yield).

Step 7:
Trimethylacetyl chloride (24 μL, 0.19 mmol) is added to a 0° C. solution of diol 43g (30 mg, 0.067 mmol) and Et$_3$N (59 μL, 0.43 mmol) in DCM (240 μL). The reaction is allowed to come to RT and stir overnight. The reaction is quenched with water (10 mL) and washed with EtOAc (10 mL). The organic layer is dried over Na$_2$SO$_4$ and concentrated. The mixture is purified by CombiFlash® Companion to give ester 43h (16 mg, 45% yield).

Step 8:
One drop of 70% perchloric acid is added to a stirred solution of alcohol 43h (46 mg, 0.087 mmol) dissolved in tert-butyl acetate (1 mL) at RT and the mixture stirred overnight. The reaction is quenched by addition of saturated NaHCO$_3$ (5 mL) and the mixture extracted with EtOAc (5 mL). The organic layer is dried over Na$_2$SO$_4$, filtered and the solvent evaporated. The residue is purified by CombiFlash® Companion to give tert-butyl ether 43i (27 mg, 53% yield).

Step 9:
LiBH$_4$ in THF (2 M, 69 μL, 0.14 mmol) is added to a solution of ester 43i (27 mg, 0.046 mmol) dissolved in THF (250 μL) and the reaction is stirred overnight at RT. Excess reagent is quenched with HCl (three drops, lots of effervescence) and the mixture neutralized with NaHCO$_3$ (10 mL) and extracted with EtOAc (3×10 mL). The combined organic layers are dried over Na$_2$SO$_4$ and concentrated to give alcohol 43j (21 mg, 91% yield).

Step 10:
Dess-Martin periodinane (120 mg, 0.28 mmol) is added in 5 portions at 20 min intervals to a solution of alcohol 43j (21 mg, 0.042 mmol) dissolved in DCM (1 mL). The reaction is then applied to a plug of SiO$_2$ (1.5×1 cm) and the product eluted with 1:1 hexanes/EtOAc (20 mL). The filtrate is evaporated to give the crude aldehyde (17 mg). The aldehyde is then dissolved in 1:1 THF/tBuOH (1 mL) and one drop of methylcyclohexene is added. A separate solution of NaClO$_2$ (31 mg, 0.34 mmol) and NaH$_2$PO$_4$ (25 mg, 0.21 mmol) in water (0.5 mL) is added to the first solution and the reaction stirred at RT. After 20 min, the reaction is diluted with water (5 mL) and extracted with EtOAc (3×10 mL). The organic layer is dried over Na$_2$SO$_4$ and concentrated. The residue is purified by preparative HPLC to give carboxylic acid 2028 (3 mg, 14% yield).

It would be apparent to those skilled in the art that the above synthetic protocols can also be used in the synthesis of other inhibitors where either 11c is replaced by another aromatic halide in Step 1 of example 42 and/or the acetanilide is replaced with another aryl-NH—CO—R$^2$, or heteroaryl-NH—CO—R$^2$ in Step 5 of example 43.

Example 44

Synthesis of Intermediate 44b

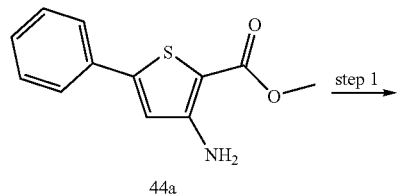

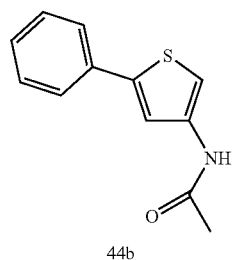

Step 1:
A solution of the ester 44a (1.0 g, 4.3 mmol) in 1.0 M NaOH (8.5 mL, 8.5 mmol) THF (8.6 mL) and MeOH (8.6 mL) is stirred at RT for 72 h and then at reflux for 3 h. The volatile solvents are reduced under pressure and 10% HCl (25 mL) is added. The white solid is collected by filtration, suspended in iso-propanol (9.1 mL) and solid oxalic acid (470 mg, 5.2 mmol) is added. The suspension is gently warmed to 40° C. for 1 h, then cooled to RT and diluted with Et$_2$O. The resulting precipitate is collected by filtration and air dried. The white solid and Et$_3$N (1.8 mL, 13 mmol) are dissolved in DCM (5 mL) and acetyl chloride (0.37 mL, 5.3 mmol) is added very slowly. The reaction is stirred for 3 h and then quenched with water (50 mL). The mixture is extracted with EtOAc (2×50 mL) and the combined organic layers dried over Na$_2$SO$_4$ and concentrated to provide pure amide 44b (473 mg, 83% yield).

Example 45

Synthesis of Compound 2034

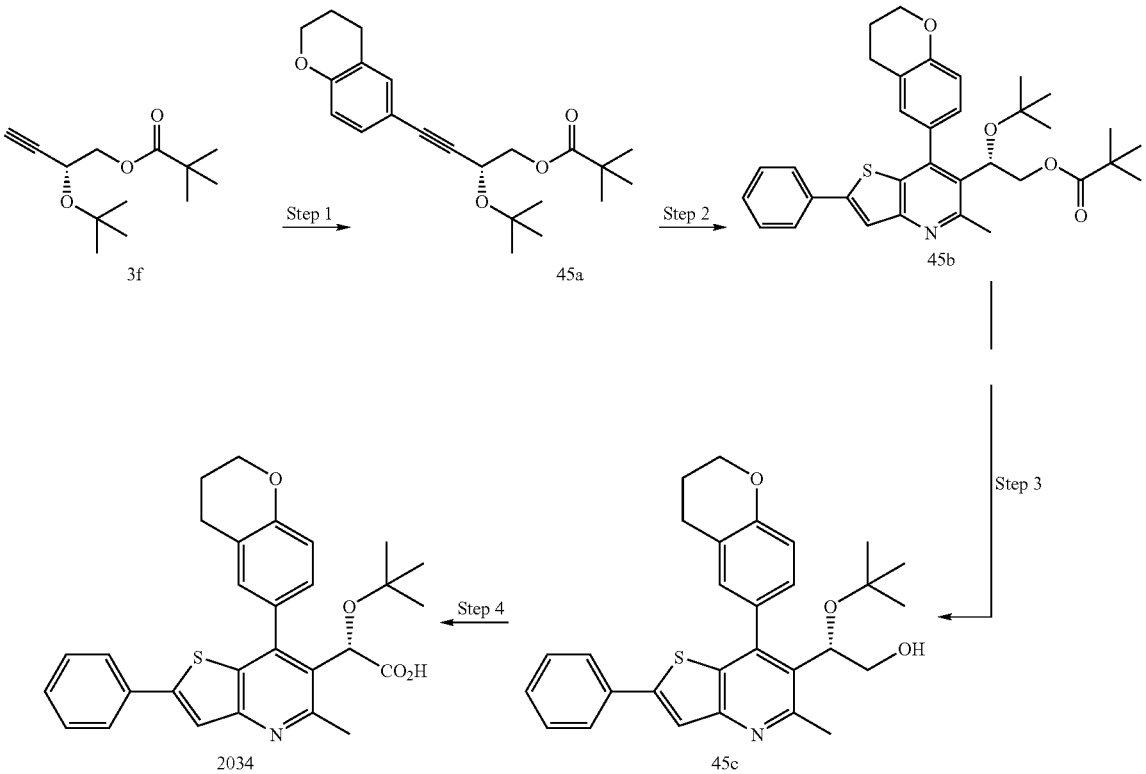

Step 1:

Solid Pd(PPh$_3$)$_4$ (9 mg, 0.008 mmol) and CuI (3 mg, 0.015 mmol) are successively added to a solution of 11c (200 mg, 0.75 mmol) and alkyne 3f (190 mg, 1.1 mmol) dissolved in DMF (0.46 mL) and diethylamine (2.3 mL). The reaction mixture is stirred overnight at RT and then concentrated, diluted with EtOAc (10 mL) and successively washed with brine, 1 N aqueous HCl and water (10 mL each). The organic layer is dried over Na$_2$SO$_4$, concentrated under reduced pressure and the residue purified by CombiFlash® Companion to give alkyne 45a (126 mg, 46% yield)

Step 2:

Tf$_2$O (75 µL, 0.45 mmol) is added via syringe over the period of 1 min to a stirred mixture of amide 44b (91 mg, 0.42 mmol) and 2-chloropyridine (53 µL 0.56 mmol) in DCM (0.8 mL) at −78° C. After 5 min, the reaction flask is placed in an ice-water bath and is warmed to 0° C. Alkyne 45a (100 mg, 0.28 mmol) in DCM (1 mL) is added via syringe. The resulting solution is allowed to warm to RT. After stirring for 30 min, triethylamine (1 mL) is added and the mixture is partitioned between DCM (50 mL) and brine (50 mL). The organic layer is washed with brine (50 mL), is dried over anhydrous Na$_2$SO$_4$ and concentrated. The residue is then purified by CombiFlash® Companion giving quinoline 45b (25 mg, 16% yield).

Step 3:

LiBH$_4$ in THF (2 M, 225 µL, 0.45 mmol) is added to a solution of ester 45b (25 mg, 0.05 mmol) dissolved in THF (180 µL) and the reaction is stirred overnight at RT. Excess reagent is quenched with HCl (one drop, lots of effervescence) and the mixture neutralized with saturated NaHCO$_3$ (10 mL) and extracted with EtOAc (3×10 mL). The combined organic layers are dried over anhydrous Na$_2$SO$_4$ and concentrated to give alcohol 45c (21 mg, >99% yield).

Step 4:

Dess-Martin periodinane (34 mg, 0.08 mmol) is added to a solution of alcohol 45c (21 mg, 0.061 mmol) dissolved in DCM (0.5 mL). After 2 h, the reaction is applied to a pad of SiO$_2$ (1.5×1 cm) and the product is eluted with 1:1 hexanes/EtOAc (20 mL). The filtrate is evaporated to give the crude aldehyde. The aldehyde is then dissolved in 2:2:1 THF/H$_2$O/tBuOH (3 mL) and 2,3-dimethyl-2-butene (0.3 mL, 1 M in THF) is added. NaClO$_2$ (45 mg, 0.50 mmol) and NaH$_2$PO$_4$ (37 mg, 0.31 mmol) are added as solids to the solution and the reaction is stirred at RT. After 30 min, the reaction is diluted with H$_2$O (5 mL) and extracted with EtOAc (3×10 mL). The organic layer is dried over anhydrous MgSO$_4$ and concentrated. The residue is purified by preparative HPLC to give compound 2034 (3 mg, 10% yield).

It would be apparent to those skilled in the art that the above synthetic protocols can also be used in the synthesis of other inhibitors where either 11c is replaced by another aromatic halide in Step 1 and/or the amide 44b is replaced with another thienyl-NH—CO—R$^2$ in Step 2.

Example 46

Synthesis of Boronate Fragment 46b (Used for the Preparation of 2046)

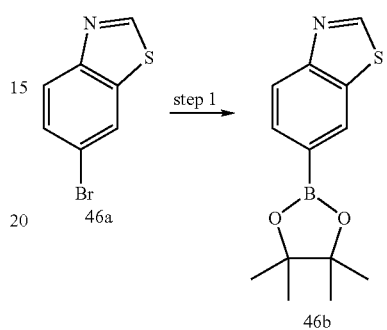

Step 1:

A stirred DMF (5 mL) solution of the arylbromide 46e (0.152 g, 0.71 mmol), potassium acetate (0.209 g, 2.1 mmol) and bis(pinacolato)diborane (0.234 g, 0.92 mmol) is degassed by bubbling Ar through the solution for 20 min. PdCl$_2$(dppf)-DCM (87 mg, 0.11 mmol) is added and degassing is continued for 15 min. The system is sealed (Teflon screw cap vessel) under Ar and heated to 90° C. for 16 h. The reaction mixture is allowed to cool to RT, dilute with EtOAc (150 mL), washed with brine (3×100 mL) and water (2×100 mL), dried over anhydrous MgSO$_4$, filtered and concentrated to dryness. The residue is purified by CombiFlash® Companion (EtOAc/hexanes) to give the desired boronate 46b (144 mg, 77% yield) as a yellowish solid.

Example 47

Synthesis of Boronate Fragment 47a (Used for the Preparation of 2047)

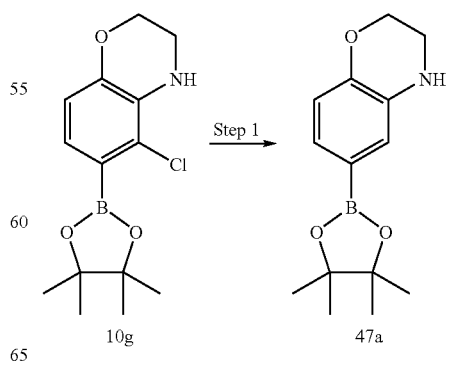

Step 1:

The reaction is carried out exactly as in step 1 of example 13, starting with 10g to provide boronic ester 47a.

Example 48

Synthesis of Boronate Fragment 48c (Used for the Preparation of 1010)

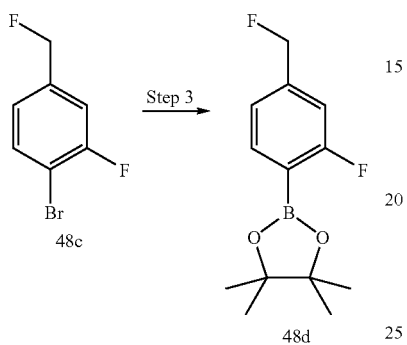

Step 1:

Solid NaBH$_4$ (603 mg, 15.9 mmol) is added to a solution of aldehyde 48a (4.11 g, 19.92 mmol) dissolved in MeOH (62 mL) at 0° C. The reaction is warmed to RT and is allowed to stir for 2 h. The reaction is quenched with aqueous HCl (1 N, 20 mL), the MeOH is removed by concentration and the product extracted with EtOAc (2×50 mL). The organic layer is washed with brine (50 mL), dried over MgSO$_4$, filtered and concentrated to afford alcohol 48b (4.1 g, 97% yield). This material is used as is in the next step.

Step 2:

To a cold solution (0° C.) of 48b (3.96 g, 19.31 mmol) in DCM (12 mL) is added diethylamino sulfur trifluoride (2.78 mL, 21.25 mmol). The reaction is warmed to RT and is allowed to stir for 2 h. The reaction is quenched with aqueous NaHCO$_3$ and extracted with DCM. The organic layer is dried with MgSO$_4$, filtered and evaporated to dryness. The product is purified by CombiFlash® Companion to afford 48c (2.1 g, 52% yield) as a colorless oil.

Step 3:

Step 3 is carried out exactly as in step 1 of example 46 to provide boronic ester 48d.

Example 49

Synthesis of Boronate Fragment 49f (Used for the Preparation of 1047, 1048)

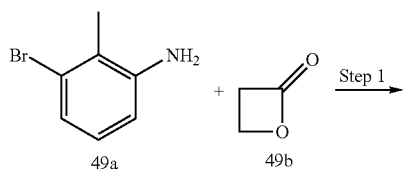

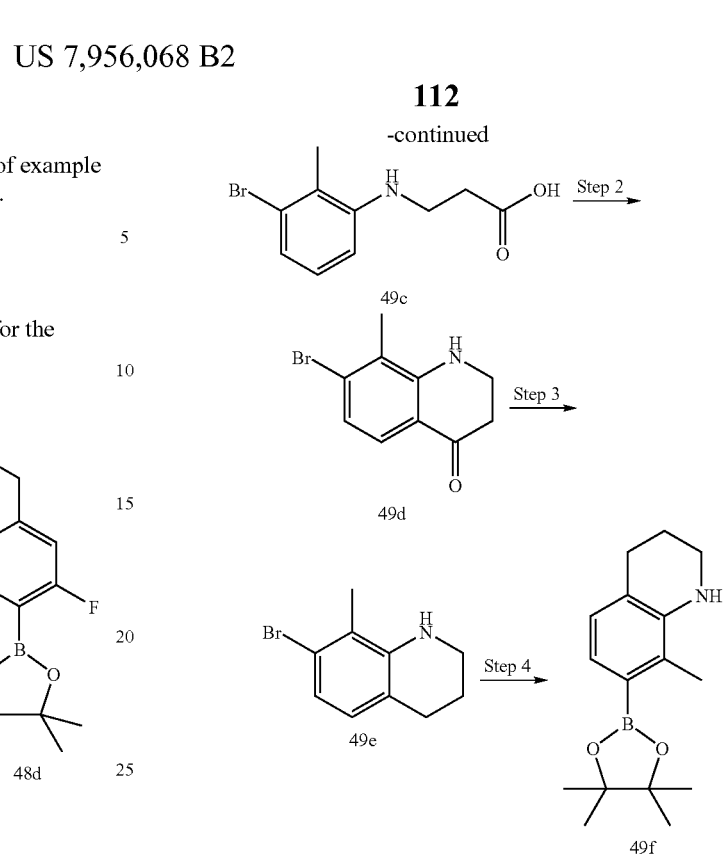

Step 1:

To a solution of 3-bromo-2-methylaniline 49a (2.44 g, 13.11 mmol) in MeCN (50 mL) is added beta-propiolactone 49b (1.8 mL, 26.2 mmol, content 90%). The reaction is heated to reflux for 48 h before the solvent is removed. The residue is dissolved in EtOAc before being washed with 1N HCl followed by brine. After drying over MgSO$_4$, the solution is concentrated to dryness and purified by Combiflash® Companion (EtOAc/hexanes) to afford the desired acid 49c (1.1 g, 33%) as a white solid.

Step 2:

Acid 49c (1.1 g, 4.26 mmol) is combined in polyphosphoric acid (40 g) and heated at 100° C. for 22 h before being cooled to RT. The residue is dissolved in EtOAc and ice before 10 N NaOH is added dropwise until pH=8. The aqueous phase is extracted with EtOAc (3×) and the combined organic phases dried over MgSO$_4$, filtered and concentrated to dryness. The residue is purified by Combiflash® Companion (EtOAc/hexanes) to afford the desired ketone 49d (0.535 g, 52%) as a yellow solid.

Step 3:

Ketone 49d (0.49 g, 2.04 mmol) is dissolved in dichloroethane (20 mL) before being treated with ZnI$_2$ (0.97 g, 3.06 mmol) and then NaBH$_3$CN (0.96 g, 15.3 mmol). The mixture is heated to reflux for 1.5 h before being cooled to RT. The mixture is diluted with EtOAc and washed with an acidified solution of NH$_4$Cl. The mixture is stirred 30 min before the phases are separated and the organic phase washed with brine. After drying (MgSO$_4$), the mixture is filtered and concentrated to dryness. Purification by Combiflash® Companion (EtOAc/hexanes) affords the desired bromide 49e (232 mg, 50%) as a white solid.

Step 4:

A well stirred DMF (10 mL) solution of the arylbromide 49e (0.26 g, 1.15 mmol), potassium acetate (0.339 g, 3.45 mmol) and bis(pinacolato)diborane (0.38 g, 1.5 mmol) is degassed by bubbling Ar through the solution for 20 min.

PdCl$_2$(dppf)-DCM (141 mg, 0.17 mmol) is added and degassing is continued for 15 min. The system is sealed (Teflon screw cap vessel) under Ar and heated to ~90° C. for 16 h. The reaction mixture is allowed to cool to RT, dilute with EtOAc (150 mL), washed with brine (3×100 mL) and water (2×100 mL), dried over anhydrous MgSO$_4$, filtered and concentrated to dryness. The residue is purified by CombiFlash® Companion (EtOAc/hexanes) to give the desired boronate 49f (252 mg, 80% yield) as a yellowish solid.

Example 50

Synthesis of Boronate Fragment 50a (Used for the Preparation of 2041)

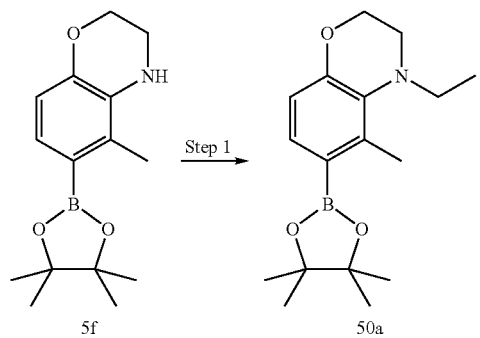

Step 1:

To a cooled solution (0° C.) of boronate 5f (400 mg, 1.45 mmol) in anhydrous DMF (8 mL) is added NaH (87.4 mg, 2.18 mmol, 60% dispersion in oil). The mixture is stirred 30 min before being treated with iodoethane (233 μL, 2.9 mmol). The resultant mixture is stirred 18 h before being quenched with water and extracted with EtOAc. The organic phase is washed with brine and dried over MgSO$_4$, filtered and concentrated. The residue is purified by CombiFlash® Companion (EtOAc/hexanes) to give 50a as colourless oil (317 mg, 72%).

Example 51

Synthesis of Boronate Fragment 51b (Used for the Preparation of 1032)

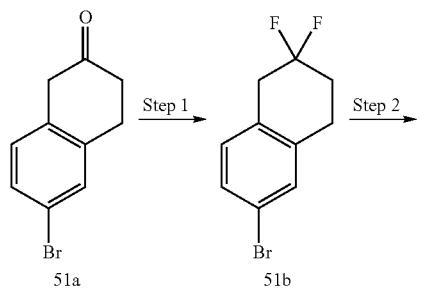

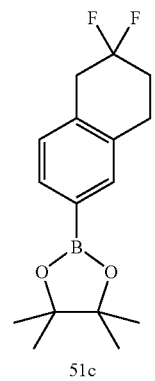

Step 1:

To a solution of 51a (500 mg, 2.15 mmol) in DCM (1.4 mL) is added bis(2-methoxyethyl)aminosulfur trifluoride (0.84 mL, 4.31 mmol) and EtOH (12.2 μL, 0.22 mmol). The reaction is sealed in a vial and stirred overnight at RT. The reaction is quenched with aqueous NaHCO$_3$ and extracted with DCM. The organic layer is dried with MgSO$_4$, filtered and evaporated to dryness. The crude product 51b (210 mg, 39% yield) is used as in next step.

Step 2:

Reaction is carried out exactly as described in step 1 of Example 46 using 51b as starting material to provide 51c.

Example 52

Synthesis of Boronate Fragment 52f (Used for the Preparation of 1018, 1019)

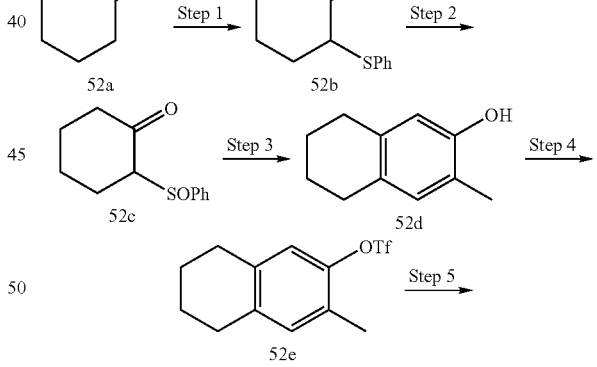

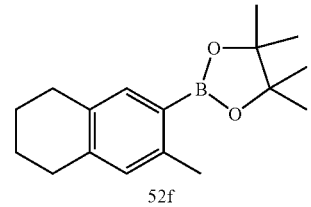

Step 1:

Lithium diisopropylamide (43.6 g, 245 mmol) is prepared in THF (400 mL), cyclohexanone 52a (21.0 mL, 204 mmol) is added dropwise at −78° C. and stirred for 1 h. This solution is added into solution of diphenyl disulphide (53.4 g, 244 mmol) in hexamethylphosphoramide (60 mL) and stirred for 2 h at RT. Reaction mixture is quenched with NH₄Cl solution and THF was distilled off. The crude compound is extracted in EtOAc (3×) and the organic layer is washed with water and brine, dried over Na₂SO₄ and concentrated under vaccum. Yellow oily liquid is purified by column chromatography on silica gel and eluted by using 5% ether/hexanes to give 52b (25.0 g, 59% yield) as a viscous oil.

Step 2:

A solution of 52b (25 g, 12 mmol) in MeOH (500 mL), NaIO₄ aqueous solution (31 g, 151 mmol) (in minimum amount of water) is added dropwise at 0° C. and stirred at RT for overnight. Reaction mixture was filtered through Celite®, precipitate is washed with MeOH. The filtrate was concentrated under vacuum and extracted with DCM; the organic layer is washed with water and brine, dried over Na₂SO₄ and concentrated under vaccum. The resulting yellow solid is crystallized in ether/hexanes system (50:50) to give 52c (17.0 g, 63%) as yellow solid.

Step 3:

To a stirred solution of 52c (5.0 g, 2.25 mmol) in MeOH (30 mL), NaOMe (1.33 g, 2.5 mmol) in MeOH (5 mL) is added dropwise at 0° C. and 3-methyl-3-buten-2-one (2.45 g, 2.9 mmol) is added dropwise. The reaction mixture is stirred overnight at 0° C. Additional NaOMe (1.33 g, 2.5 mmol) is added and the reaction mixture is stirred at RT for 2 days. MeOH is distilled off and the resulting solution is poured onto 5% HCl solution. The aqueous layer is extracted with EtOAc. The organic layer is washed with brine, dried over Na₂SO₄ and concentrated under vacuum. The crude compound was chromatographed (5-10% Ether/Hexanes gradient elution) to give 52d (506 mg, 14% yield) as a white solid.

Step 3:

Reaction is carried out exactly as described in step 5 of Example 17 using 52d as starting material to provide 52e.

Step 4:

Reaction is carried out exactly as described in step 6 of Example 17 using 52e as starting material to provide boronate 52f.

Example 53

Synthesis of Boronate Fragment 53c (Used for the Preparation of 1061, 1062, 2042, 2043)

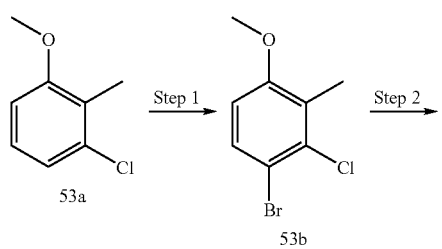

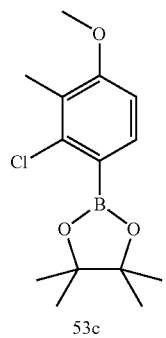

Step 1

To a solution of 3-chloro-2-methylanisole 53a in AcOH (100 mL) is added dropwise bromine (1.7 mL, 33.5 mmol). After 2 h at RT the reaction mixture is concentrated under vacuum, then diluted with EtOAc, washed with 1.0 N NaOH, saturated Na₂S₂O₃, water and brine, dried (MgSO₄), filtered and concentrated under vacuum to give bromide 53b as a colorless oil (5.97 g, 79% yield).

Step 2:

Reaction is carried out exactly as described in step 1 of Example 46 using 53b as starting material to provide 53c.

Example 54

Synthesis of Compounds 1055 and 1056

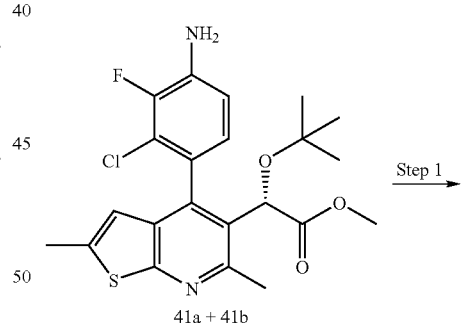

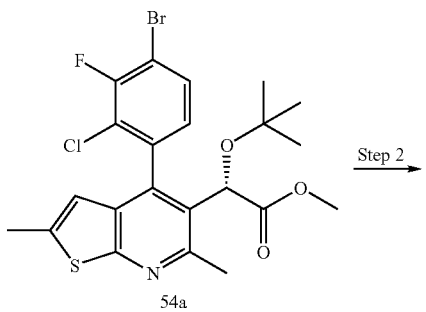

117

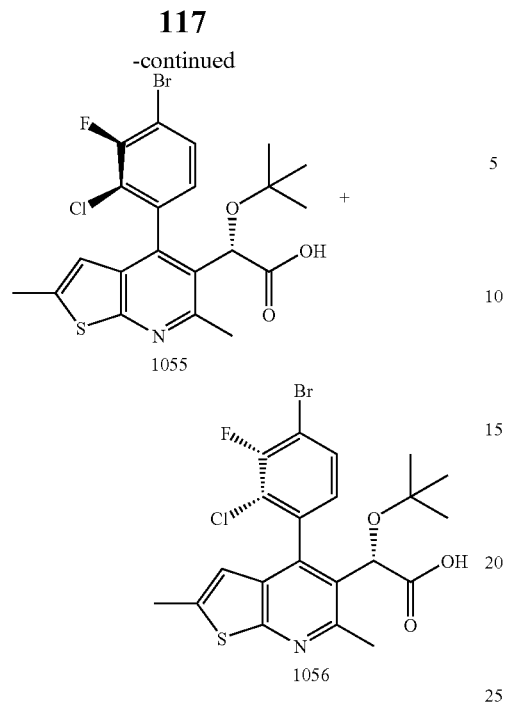

Step 1:

To CuBr₂ (37.15 mg, 0.166 mmol) and tert-butyl nitrite (0.253 mmol) in anhydrous MeCN (600 μL) at RT is slowly added under argon a mixture of aniline 41a and 41b (60.0 mg, 0.133 mmol) in MeCN (400 μL). The reaction is stirred for 1 h then quenched with 1.0 N HCl and extracted with EtOAc (3×). The combined organic extracts are washed with water and brine, dried (MgSO₄), filtered and concentrated under vacuum to give crude 54a as a mixture of atropisomers (76.1 mg, 68% yield) which was used as such in the next step.

Step 2:

A solution of 54a (68.5 mg, 0.133 mmol) in THF (3 mL)/MeOH (1.5 mL) is treated at RT with 1.0 N NaOH (1 mL). The reaction mixture is stirred at 50° C. overnight. The cooled reaction mixture is acidified with 1.0 N HCl (pH ~4-5), extracted with DCM, dried (MgSO₄), filtered and concentrated under vacuum. The mixture is purified by preparative reverse phase HPLC and the pure fractions are pooled and lyophilized to give inhibitor 1055 (16.7 mg, 25% yield) and 1056 (4.3 mg, 6.5% yield) as white solids.

Example 55

Synthesis of Compound 1057 and 1058

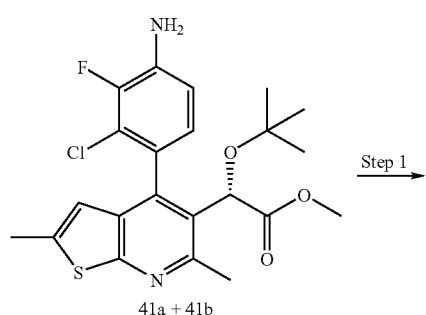

118

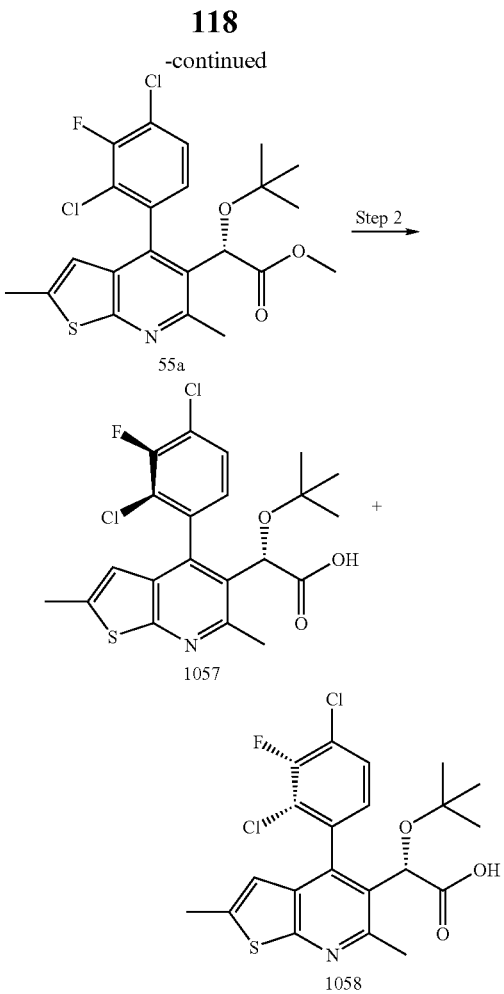

Step 1:

Reaction is carried out exactly as described in step 1 of Example 54 except using CuCl₂ instead of CuBr₂ to provide 55a as mixture of atropisomers.

Step 2:

Reaction is carried out exactly as described in step 2 of Example 54 using 55a as starting material to provide after separation compounds 1057 and 1058 as white solids.

It would be apparent to those skilled in the art that the above synthetic protocols for Examples 54 and 55 can also be used in the synthesis of other inhibitors for table 2 starting from iodo intermediate 1B.

Example 56

C8166 HIV-1 Luciferase Assay (EC₅₀)

C8166 cells are derived from a human T-lymphotrophic virus type 1 immortalized but nonexpressing line of cord blood lymphocytes (obtained from J. Sullivan) and are highly permissive to HIV-1 infection. The pGL3 Basic LTR/TAR plasmid is made by introducing the HIV-1 HxB2 LTR sequence from nucleotide −138 to +80 (Sca1-HindIII) upstream of the luciferase gene in the pGL3 Basic Vector (a promoterless luciferase expression vector from Promega catalogue #E1751) with the gene for blasticidine resistance cloned in. The reporter cells are made by electroporating C8166 cells with pGL3 Basic LTR/TAR and selecting positive clones with blasticidine. Clone C8166-LTRluc #A8-F5-

G7 was selected by 3 consecutive rounds of limiting dilution under blasticidine selection. Cultures are maintained in complete media (consisting of: Roswell Park Memorial Institute medium (RPMI) 1640+10% FBS+$10^{-5}$ M β-mercaptoethanol+10 μg/ml gentamycin) with 5 μg/ml blasticidine, however, blasticidine selection is removed from the cells before performing the viral replication assay.

Luciferase Assay Protocol

Preparation of Compounds

Serial dilutions of HIV-1 inhibitor compounds are prepared in complete media from 10 mM DMSO stock solutions. Eleven serial dilutions of 2.5× are made at 8× desired final concentration in a 1 mL deep well titer plate (96 wells). The $12^{th}$ well contains complete media with no inhibitor and serves as the positive control. All samples contain the same concentration of DMSO (≦0.1% DMSO). A 25 μL aliquot of inhibitor is added, to triplicate wells, of a 96 well tissue culture treated clear view black microtiter plate (Corning Costar catalogue #3904). The total volume per well is 200 μL of media containing cells and inhibitor. The last row is reserved for uninfected C8166 LTRluc cells to serve as the background blank control and the first row is media alone.

Infection of Cells

C8166 LTRluc cells are counted and placed in a minimal volume of complete RPMI 1640 in a tissue culture flask (ex. 30×$10^6$ cells in 10 mL media/25 $cm^2$ flask). Cells are infected with HIV-1 or virus with variant integrase generated as described below at a molecules of infection (moi) of 0.005. Cells are incubated for 1.5 hours at 37° C. on a rotating rack in a 5% $CO_2$ incubator and re-suspended in complete RPMI to give a final concentration of 25,000-cells/175 μL. 175 μL of cell mix is added to wells of a 96 well microtiter plate containing 25 μL 8× inhibitors. 25,000 uninfected C8166-LTR-luc cells/well in 200 μL complete RPMI are added to the last row for background control. Cells are incubated at 37° C. in 5% $CO_2$ incubator for 3 days.

Luciferase Assay

50 μl Steady Glo (luciferase substrate $T_{1/2}$=5 hours Promega catalogue #E2520) is added to each well of the 96 well plate. The relative light units (RLU) of luciferase is determined using the LUMIstar Galaxy luminometer (BMG LabTechnologies). Plates are read from the bottom for 2 seconds per well with a gain of 240.

The level of inhibition (% inhibition) of each well containing inhibitor is calculated as follows:

$$\%\cdot\text{inhibition} = \left(1 - \left[\frac{RLU\cdot\text{well} - RLU\cdot\text{blank}}{RLU\cdot\text{control} - RLU\cdot\text{blank}}\right]\right) * 100$$

The calculated % inhibition values are used to determine $EC_{50}$, slope factor (n) and maximum inhibition ($I_{max}$) by the non-linear regression routine NLIN procedure of SAS using the following equation:

$$\%\cdot\text{inhibition} = \frac{I_{max} \times [\text{inhibitor}]^n}{[\text{inhibitor}]^n + IC_{50}^n}$$

Table of Compounds

Compounds of the invention shown in Tables 1 to 4 are integrase inhibitors. Representative compounds selected from Tables 1 to 2 below have $EC_{50}$ values of no more than 20 μM when tested in the HIV-1 luciferase assay of Example 46.

Retention times ($t_R$) for each compound are measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

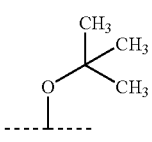

| Cpd | $R^3$ | $R^4$ | $R^6$ | $R^5$ | $t_R$ (min) | MS $(M + H)^+$ |
|---|---|---|---|---|---|---|
| 1001 | 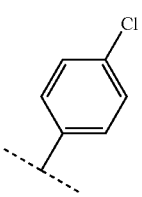 |  | $CH_3$ | $CH_3$ | 5.8 | 418.1/ 420.1 |

TABLE 1-continued
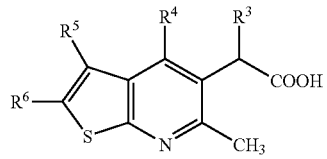
| Cpd | R³ | R⁴ | R⁶ | R⁵ | $t_R$ (min) | MS $(M + H)^+$ |
|---|---|---|---|---|---|---|
| 1002 | OC(CH₃)₃ | 4-Cl-C₆H₄ | CH₂CH₃ | H | 6.2 | 418.1/ 420.1 |
| 1003 | OC(CH₃)₃ | 4-Cl-C₆H₄ | CH₃ | H | 5.7 | 404.1/ 406.1 |
| 1004 | OCH(CH₃)₂ | 4-Cl-C₆H₄ | CH₃ | H | 5.4 | 390.1/ 392.1 |
| 1005 | OC(CH₃)₃ (S) | 4-Cl-C₆H₄ | CH₃ | H | 5.7 | 404.1/ 406.1 |
| 1006 | OC(CH₃)₃ (R) | 4-Cl-C₆H₄ | CH₃ | H | 5.7 | 404.1/ 406.1 |
| 1007 | OC(CH₃)₃ (S) | 4-Cl-C₆H₄ | CH₂CH₃ | H | 6.1 | 418.1/ 420.1 |
| 1008 | OC(CH₃)₃ (R) | 4-Cl-C₆H₄ | CH₂CH₃ | H | 6.1 | 418.1/ 420.1 |

TABLE 1-continued
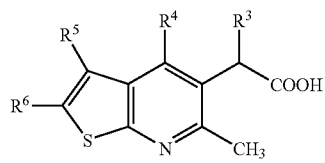
| Cpd | R³ | R⁴ | R⁶ | R⁵ | t_R (min) | MS (M + H)⁺ |
|---|---|---|---|---|---|---|
| 1009 | OC(CH₃)₂ | chroman-6-yl | CH₃ | H | 4.8 | 426.1 |
| 1010 | OC(CH₃)₂ | 3,4-difluoro-phenyl (with F) | CH₃ | H | 4.8 | 420.2 |
| 1011 | OC(CH₃)₂ | chroman-7-yl | CH₃ | H | 5.8 | 426.1 |
| 1012 | OC(CH₃)₂ | 4-chloro-3,5-difluorophenyl | CH₃ | H | 7.4 | 440.0/ 442.0 |
| 1013 | OC(CH₃)₂ | chroman-6-yl | H | H | 6.0 | 412.1 |
| 1014 | OC(CH₃)₂ | 4-chlorophenyl | H | H | 6.6 | 390.0/ 392.0 |

TABLE 1-continued
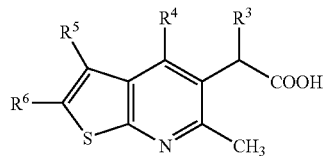
| Cpd | R³ | R⁴ | R⁶ | R⁵ | $t_R$ (min) | MS $(M + H)^+$ |
|---|---|---|---|---|---|---|
| 1015 | OC(CH₃)₃ | 2-F-4-Cl-phenyl | CH₃ | H | 7.0 | 422.1/424.1 |
| 1016 | OC(CH₃)₃ | 3-F-4-Cl-phenyl | CH₃ | H | 7.1 | 422.1/424.1 |
| 1017 | OC(CH₃)₃ | 2,3-dihydrobenzofuran-5-yl | CH₃ | H | 5.8 | 412.1 |
| 1018 | OC(CH₃)₃ | tetrahydronaphthyl | CH₃ | H | 7.6 | 438.2 |
| 1019 | OC(CH₃)₃ | tetrahydronaphthyl | CH₃ | H | 7.6 | 438.2 |
| 1020 | OC(CH₃)₃ | tetrahydronaphthyl | CH₃ | H | 7.3 | 424.1 |
| 1021 | OC(CH₃)₃ | indanyl | CH₃ | H | 5.2 | 410.2 |

TABLE 1-continued
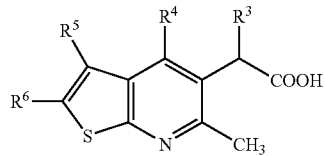
| Cpd | R³ | R⁴ | R⁶ | R⁵ | t_R (min) | MS (M + H)⁺ |
|---|---|---|---|---|---|---|
| 1022 | —C(CH₃)₂OCH₃ (OC(CH₃)₃) | 2-Cl-3,5-dimethylphenyl | CH₃ | H | 7.4 | 432.1/ 434.1 |
| 1023 | —OC(CH₃)₃ | 7-Cl-chroman-4-yl | CH₃ | H | 6.2 | 460.1/ 462.1 |
| 1024 | —OC(CH₃)₃ | 7-Cl-chroman-4-yl | CH₃ | H | 6.5 | 460.1/ 462.1 |
| 1025 | —OC(CH₃)₃ | 7-F-chroman-4-yl | CH₃ | H | 4.9 | 444.1 |
| 1026 | —OC(CH₃)₃ | 7-F-chroman-4-yl | CH₃ | H | 5.0 | 444.1 |
| 1027 | —OC(CH₃)₃ | 5-Cl-chroman-4-yl | CH₃ | H | 6.1 | 460.1/ 462.1 |

TABLE 1-continued

| Cpd | R³ | R⁴ | R⁶ | R⁵ | t_R (min) | MS (M + H)⁺ |
|---|---|---|---|---|---|---|
| 1028 | O-C(CH₃)₂CH₃ | chloro-chroman | CH₃ | H | 6.2 | 460.1/462.1 |
| 1029 | O-C(CH₃)₂CH₃ | methyl-chloro-chroman | CH₃ | H | 6.4 | 474.1/476.1 |
| 1030 | O-C(CH₃)₂CH₃ | methyl-chroman | CH₃ | H | 5.7 | 440.3 |
| 1031 | O-C(CH₃)₂CH₃ | methyl-chroman | CH₃ | H | 5.7 | 440.3 |
| 1032 | O-C(CH₃)₂CH₃ | difluoro-tetralin | CH₃ | H | 5.0 | 460.2 |
| 1033 | O-C(CH₃)₂CH₃ | difluoro-tetralin | CH₃ | H | 5.0 | 460.2 |

TABLE 1-continued
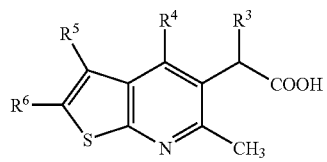
| Cpd | R³ | R⁴ | R⁶ | R⁵ | t_R (min) | MS (M + H)⁺ |
|---|---|---|---|---|---|---|
| 1034 | OC(CH₃)₃ | 5-methylquinolin-8-yl | CH₃ | H | 4.4 | 435.2 |
| 1035 | OC(CH₃)₃ | 5-methylquinolin-8-yl | CH₃ | H | 4.6 | 435.2 |
| 1036 | OC(CH₃)₃ | 5-chloroquinolin-8-yl | CH₃ | H | 5.9 | 455.1/ 457.1 |
| 1037 | OC(CH₃)₃ | (methyl-dihydrobenzoxazine) | CH₃ | H | 4.9 | 441.2 |
| 1038 | OC(CH₃)₃ | (chlorochromanyl) | CH₃ | CH₃ | 5.4 | 474.1/ 476.1 |
| 1039 | OC(CH₃)₃ | (chlorochromanyl) | CH₃ | CH₃ | 5.4 | 474.1/ 476.1 |

TABLE 1-continued

| Cpd | R³ | R⁴ | R⁶ | R⁵ | $t_R$ (min) | MS $(M + H)^+$ |
|---|---|---|---|---|---|---|
| 1040 | OC(CH₃)₃ | chroman-5-methyl | CH₃ | CH₃ | 5.3 | 454.2 |
| 1041 | OC(CH₃)₃ | 4-amino-chroman-5-methyl | CH₃ | CH₃ | 4.7 | 455.2 |
| 1042 | OC(CH₃)₃ | 4-amino-chroman-5-methyl | CH₃ | H | 4.2 | 441.2 |
| 1043 | OC(CH₃)₃ | 4-chloro-chroman-5-methyl | CH₃ | H | 6.9 | 460.2/ 462.2 |
| 1044 | OC(CH₃)₃ | 4-chloro-chroman-5-methyl | CH₃ | H | 6.9 | 460.2/ 462.2 |
| 1045 | OC(CH₃)₃ | 4-amino-5-chloro-chroman-5-methyl | CH₃ | H | 4.9 | 461.1/ 463.1 |

TABLE 1-continued
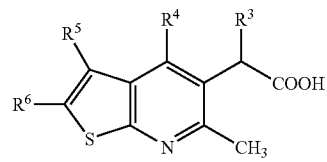
| Cpd | R³ | R⁴ | R⁶ | R⁵ | t_R (min) | MS (M + H)⁺ |
|---|---|---|---|---|---|---|
| 1046 | OC(CH₃)₃ | 5-Cl, 8-(2,3-dihydro-1,4-benzoxazin-4-yl) | CH₃ | H | 5.2 | 461.1/ 463.1 |
| 1047 | OC(CH₃)₃ | 1,2,3,4-tetrahydroquinolin-8-yl | CH₃ | H | 4.2 | 439.2 |
| 1048 | OC(CH₃)₃ | 1,2,3,4-tetrahydroquinolin-8-yl | CH₃ | H | 4.7 | 439.2 |
| 1049 | OC(CH₃)₃ | 5-Cl, 8-F-chroman-6-yl | CH₃ | H | 6.8 | 478.2/ 480.1 |
| 1050 | OC(CH₃)₃ | 5-Cl, 8-F-chroman-6-yl | CH₃ | H | 6.7 | 478.1/ 480.1 |
| 1051 | OC(CH₃)₃ | 5-Cl-2,3-dihydro-1,4-benzoxazin-6-yl | CH₃ | CH₃ | 6.1 | 475.3/ 477.3 |

TABLE 1-continued

| Cpd | R³ | R⁴ | R⁶ | R⁵ | t_R (min) | MS (M + H)⁺ |
|---|---|---|---|---|---|---|
| 1052 | O-C(CH₃)₂-CH₃ | chloro-dihydrobenzoxazine | CH₃ | CH₃ | 6.5 | 475.3/ 477.3 |
| 1053 | O-C(CH₃)₂-CH₃ | F, Cl, NH₂-phenyl | CH₃ | H | 4.8 | 437.2/ 439.2 |
| 1054 | O-C(CH₃)₂-CH₃ | F, Cl, NH₂-phenyl | CH₃ | H | 5.0 | 437.2/ 439.2 |
| 1055 | O-C(CH₃)₂-CH₃ | F, Cl, Br-phenyl | CH₃ | H | 6.4 | 500.1/ 602.1/ 504.1 |
| 1056 | O-C(CH₃)₂-CH₃ | F, Cl, Br-phenyl | CH₃ | H | 6.5 | 500.1/ 502.1/ 504.1 |
| 1057 | O-C(CH₃)₂-CH₃ | F, Cl, Cl-phenyl | CH₃ | H | 6.3 | 456.1/ 458.1/ 460.1 |
| 1058 | O-C(CH₃)₂-CH₃ | F, Cl, Cl-phenyl | CH₃ | H | 6.4 | 456.1/ 458.1/ 460.1 |

TABLE 1-continued

| Cpd | R³ | R⁴ | R⁶ | R⁵ | t_R (min) | MS (M + H)⁺ |
|---|---|---|---|---|---|---|
| 1059 | O-C(CH₃)₃ | (3,4-dihydro-2H-chromeno-fused pyridine) | CH₃ | H | 4.0 | 463.3 |
| 1060 | O-C(CH₃)₃ | (3,4-dihydro-2H-chromeno-fused pyridine, isomer) | CH₃ | H | 4.1 | 463.3 |
| 1061 | O-C(CH₃)₃ | 3-Cl-2-CH₃-6-OCH₃-phenyl | CH₃ | H | 7.3 | 448.1/450.1 |
| 1062 | O-C(CH₃)₃ | 3-Cl-2-CH₃-6-OCH₃-phenyl | CH₃ | H | 7.0 | 448.1/450.1 |
| 1063 | O-C(CH₃)₃ | Cl-naphthyl | CH₃ | H | 7.5 | 454.1/456.1 |
| 1064 | O-C(CH₃)₃ | Cl-naphthyl | CH₃ | H | 7.6 | 454.1/456.1 |

TABLE 2

[Structure: thieno[3,2-b]pyridine core with R⁴ and R³-CH-COOH at one position, R⁶, R⁷ substituents, and CH₃ group]

| Cpd | R³ | R⁴ | R⁶ | R⁷ | $t_R$ (min) | MS $(M+H)^+$ |
|---|---|---|---|---|---|---|
| 2001 | O-C(CH₃)₃ | 6-chromanyl | H | H | 4.8 | 412.1 |
| 2002 | O-C(CH₃)₃ | 4-Cl-phenyl | H | H | 5.0 | 390.0/ 392.0 |
| 2003 | O-C(CH₃)₃ | 4-Cl-2-F-phenyl | H | H | 5.0 | 408.0/ 410.0 |
| 2004 | O-C(CH₃)₃ | 4-Cl-3-F-phenyl | H | H | 5.2 | 408.0/ 410.0 |
| 2005 | O-C(CH₃)₃ | (2S,3R)-7-F-chroman-6-yl | CH₃ | H | 5.0 | 444.1 |
| 2006 | O-C(CH₃)₃ | (2R,3S)-7-F-chroman-6-yl | CH₃ | H | 5.3 | 444.1 |

TABLE 2-continued

| Cpd | R³ | R⁴ | R⁶ | R⁷ | t_R (min) | MS (M + H)⁺ |
|---|---|---|---|---|---|---|
| 2007 | OC(CH₃)₃ | 5-Cl-chroman-6-yl | CH₃ | H | 5.2 | 460.0/462.0 |
| 2008 | OC(CH₃)₃ | 5-Cl-chroman-6-yl | CH₃ | H | 5.4 | 460.0/462.0 |
| 2009 | OC(CH₃)₃ | 8-Cl-benzodioxepin-7-yl | CH₃ | H | 5.3 | 474.1/476.1 |
| 2010 | OC(CH₃)₃ | 8-Cl-chroman-6-yl | CH₃ | H | 5.6 | 474.1/476.1 |
| 2011 | OC(CH₃)₃ | chroman-6-yl | CH₃ | H | 5.2 | 440.2 |
| 2012 | OC(CH₃)₃ | 4-Cl-phenyl | CH₃ | H | 5.1 | 404.1/406.1 |

TABLE 2-continued

| Cpd | R³ | R⁴ | R⁶ | R⁷ | t_R (min) | MS (M + H)⁺ |
|---|---|---|---|---|---|---|
| 2013 | OC(CH₃)₃ | 4-Cl-C₆H₄-CH₂- | H | CH(CH₃)- | 5.1 | 404.1/ 406.1 |
| 2014 | OC(CH₃)₃ | chroman-6-ylmethyl | CH₃ | H | 4.9 | 426.2 |
| 2015 | OC(CH₃)₃ | chroman-6-ylmethyl | H | CH₃ | 4.9 | 426.2 |
| 2016 | OC(CH₃)₃ | 4-chloro-indan-5-ylmethyl | CH₃ | H | 5.5 | 444.3/ 446.3 |
| 2017 | OC(CH₃)₃ | 4-chloro-indan-5-ylmethyl | CH₃ | H | 5.8 | 444.3/ 446.3 |
| 2018 | OC(CH₃)₃ | 5-methyl-quinolin-8-ylmethyl | CH₃ | H | 4.0 | 435.2 |

TABLE 2-continued

| Cpd | R³ | R⁴ | R⁶ | R⁷ | t_R (min) | MS (M + H)⁺ |
|---|---|---|---|---|---|---|
| 2019 | OC(CH₃)₃ | 5-chloroquinolin-8-yl | CH₃ | H | 4.5 | 455.1/ 457.1 |
| 2020 | OC(CH₃)₃ | (3,4-dihydro-2H-benzo[b][1,4]oxazin-5-yl) | CH₃ | H | 3.9 | 441.2 |
| 2021 | OC(CH₃)₃ | (3,4-dihydro-2H-benzo[b][1,4]oxazin-5-yl) | CH₃ | H | 4.5 | 441.2 |
| 2022 | OC(CH₃)₃ | 5-methylquinolin-8-yl | CH₃ | H | 4.1 | 435.2 |
| 2023 | OC(CH₃)₃ | 5-chloroquinolin-8-yl | CH₃ | H | 4.5 | 455.1/ 457.1 |
| 2024 | OC(CH₃)₃ | (5-chloro-3,4-dihydro-2H-benzo[b][1,4]oxazin-8-yl) | CH₃ | H | 4.2 | 461.2/ 463.2 |

TABLE 2-continued

| Cpd | R³ | R⁴ | R⁶ | R⁷ | t_R (min) | MS (M + H)⁺ |
|---|---|---|---|---|---|---|
| 2025 | OC(CH₃)₃ | 5-Cl-3,4-dihydro-2H-benzo[b][1,4]oxazin-6-yl | CH₃ | H | 4.4 | 461.2/ 463.2 |
| 2026 | OC(CH₃)₃ | 8-Cl-chroman-6-yl | CH₃ | H | 4.4 | 460.2/ 462.2 |
| 2027 | OC(CH₃)₃ | 8-Cl-chroman-6-yl | CH₃ | H | 4.6 | 460.2/ 462.2 |
| 2028 | OC(CH₃)₃ | chroman-6-yl | CH₃ | benzyl | 5.6 | 516.3 |
| 2029 | OC(CH₃)₃ | 4-Br-3-Cl-2-F-phenyl | CH₃ | H | 5.3 | 500.0/ 502.0/ 504.0 |
| 2030 | OC(CH₃)₃ | 4-Br-3-Cl-2-F-phenyl | CH₃ | H | 5.1 | 500.0/ 502.0/ 504.0 |

TABLE 2-continued

[Structure: thieno[3,2-b]pyridine core with R⁴, R³, R⁶, R⁷ substituents, CH₃ group, and CH(R³)COOH side chain]

| Cpd | R³ | R⁴ | R⁶ | R⁷ | $t_R$ (min) | MS $(M+H)^+$ |
|---|---|---|---|---|---|---|
| 2031 | OC(CH₃)₃ | 5,6-dichloro-4-fluorophenyl (trans) | CH₃ | H | 5.1 | 456.1/ 458.0/ 460.0 |
| 2032 | OC(CH₃)₃ | 5,6-dichloro-4-fluorophenyl (cis) | CH₃ | H | 5.3 | 456.1/ 458.1/ 460.1 |
| 2033 | OC(CH₃)₃ | chroman-6-yl | H | allyloxymethyl | 5.4 | 482.2 |
| 2034 | OC(CH₃)₃ | chroman-6-yl | phenyl | H | 5.7 | 488.2 |
| 2035 | OC(CH₃)₃ | pyrano-quinoline | CH₃ | H | 3.83 | 463.3 |
| 2036 | OC(CH₃)₃ | pyrano-isoquinoline | CH₃ | H | 3.23 | 463.3 |

TABLE 2-continued

| Cpd | R³ | R⁴ | R⁶ | R⁷ | t_R (min) | MS (M + H)⁺ |
|---|---|---|---|---|---|---|
| 2037 | O-C(CH₃)₃ | benzofuran-5-yl | CH₃ | H | 3.23 | 410.2 |
| 2038 | O-C(CH₃)₃ | benzothiazol-6-yl | CH₃ | H | 2.97 | 427.2 |
| 2039 | O-C(CH₃)₃ | 3-chloro-4-methoxy-5-methylphenyl | CH₃ | H | 5.53 | 448.1/ 450.1 |
| 2040 | O-C(CH₃)₃ | 3-chloro-4-methoxy-5-methylphenyl | CH₃ | H | 5.64 | 448.1/ 450.1 |
| 2041 | O-C(CH₃)₃ | 4-ethyl-5-methyl-3,4-dihydro-2H-benzo[1,4]oxazin-6-yl | CH₃ | H | 3.35 | 469.2 |
| 2042 | O-C(CH₃)₃ | 3-chloro-6-methoxy-5-methylphenyl | CH₃ | H | 5.56 | 448.1/ 450.1 |

TABLE 2-continued

| Cpd | R³ | R⁴ | R⁶ | R⁷ | t_R (min) | MS (M + H)⁺ |
|---|---|---|---|---|---|---|
| 2043 | -O-C(CH₃)₃ | 3-methyl-2-chloro-6-methoxyphenyl | CH₃ | H | 5.90 | 448.1/450.1 |
| 2044 | -O-C(CH₃)₃ | 1-chloronaphth-2-yl | CH₃ | H | 5.76 | 454.1/456.1 |
| 2045 | -O-C(CH₃)₃ | 1-chloronaphth-2-yl | CH₃ | H | 5.96 | 454.1/456.1 |
| 2046 | -O-C(CH₃)₃ | benzothiazol-6-yl | CH₃ | H | 4.20 | 427.1 |
| 2047 | -O-C(CH₃)₃ | 3,4-dihydro-2H-benzo[1,4]oxazin-6-yl | CH₃ | H | 4.55 | 427.2 |

TABLE 3

| Cpd | R⁴ | R⁵ | R⁶ | R² |
|---|---|---|---|---|
| 3001 | 8-chloro-chroman-6-yl | H | 1H-pyrazol-4-yl | CH₃ |
| 3002 | 8-chloro-chroman-6-yl | H | H | CH₃ |
| 3003 | 8-chloro-chroman-6-yl | H | H | 2-methoxyethyl |
| 3004 | 5-methyl-chroman-6-yl | H | 1H-pyrazol-4-yl | CH₃ |
| 3005 | 5-methyl-chroman-6-yl | H | H | CH₃ |
| 3006 | 3-bromo-2-fluoro-4-chloro-phenyl | H | 1H-pyrazol-4-yl | CH₃ |

TABLE 3-continued

| Cpd | R⁴ | R⁵ | R⁶ | R² |
|---|---|---|---|---|
| 3007 | 5-methyl-chroman-6-yl | H | H | 2-methoxyethyl |

TABLE 4

| Cpd | R⁴ | R⁶ | R⁷ | R² |
|---|---|---|---|---|
| 4001 | 8-chloro-chroman-6-yl | H | H | CH₃ |
| 4002 | 8-chloro-chroman-6-yl | H | 1H-pyrazol-4-yl | CH₃ |
| 4003 | 8-chloro-chroman-6-yl | H | H | 2-methoxyethyl |

TABLE 4-continued

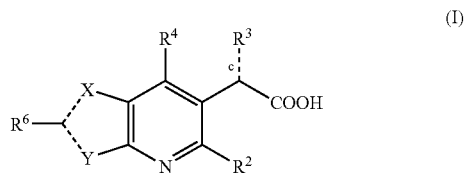

| Cpd | R⁴ | R⁶ | R⁷ | R² |
|---|---|---|---|---|
| 4004 | (chroman with H₃C) | H | H | CH₃ |
| 4005 | (chroman with H₃C) | H | H | (pyrazole) |
| 4006 | (F, Br, Cl phenyl) | H | H | CH₃ |
| 4007 | (chroman with H₃C) | H | H | (CH₂OCH₃ group) |

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of the formula (I)

(I)

wherein
------ represents either a single or double bond;
X is S or $CR^5$;
Y is S or $CR^7$;
wherein one of X or Y is S;
$R^2$, $R^5$, $R^6$ and $R^7$ are each independently selected from:
a) halo;
b) $R^8$, —C(=O)—$R^8$, —C(=O)—O—$R^8$, —O—$R^8$, —S—$R^8$, SO—$R^8$, —SO₂—$R^8$, —(C$_{1-6}$)alkylene-$R^8$, —(C$_{1-6}$)alkylene-C(=O)—$R^8$, —(C$_{1-6}$)alkylene-C(=O)—O—$R^8$, —(C$_{1-6}$)alkylene-SO—$R^8$ or —(C$_{1-6}$)alkylene-SO₂—$R^8$, —(C$_{1-6}$)alkylene-O—$R^8$ or —(C$_{1-6}$)alkylene-S—$R^8$;
wherein $R^8$ is in each instance independently selected from H, (C$_{1-6}$)alkyl, (C$_{2-6}$)alkenyl, (C$_{2-6}$)alkynyl, (C$_{1-6}$)haloalkyl, (C$_{3-7}$)cycloalkyl, aryl and Het; and
wherein each of the aryl and Het is optionally substituted with 1 to 3 substituents each independently selected from:
i) halo, oxo, thioxo, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —O(C$_{1-6}$)haloalkyl, —SH, —S(C$_{1-6}$)alkyl, —SO(C$_{1-6}$)alkyl, —SO₂(C$_{1-6}$)alkyl, —NH₂, —NH(C$_{1-6}$)alkyl and —N((C$_{1-6}$)alkyl)₂;
ii) (C$_{1-6}$)alkyl optionally substituted with —OH, —O—(C$_{1-6}$)haloalkyl, or —O—(C$_{1-6}$)alkyl; and
iii) aryl or Het, wherein each of the aryl and Het is optionally substituted with halo or (C$_{1-6}$)alkyl; and
c) —N($R^9$)$R^{10}$, —C(=O)—N($R^9$)$R^{10}$, —O—C(=O)—N($R^9$)$R^{10}$, —SO₂—N($R^9$)$R^{10}$, —(C$_{1-6}$)alkylene-N($R^9$)$R^{10}$, —(C$_{1-6}$)alkylene-C(=O)—N($R^9$)$R^{10}$, —(C$_{1-6}$)alkylene-O—C(=O)—N($R^9$)$R^{10}$, or —(C$_{1-6}$)alkylene-SO₂—N($R^9$)$R^{10}$ wherein
$R^9$ is in each instance independently selected from H, (C$_{1-6}$)alkyl and (C$_{3-7}$)cycloalkyl; and
$R^{10}$ is in each instance independently selected from $R^8$, —(C$_{1-6}$)alkylene-$R^8$, —SO₂—$R^8$, —C(=O)—$R^8$, —C(=O)O$R^8$ and —C(=O)N($R^9$)$R^8$; wherein $R^8$ and $R^9$ are as defined above;

$R^3$ is (C$_{1-6}$)alkyl, (C$_{1-6}$)haloalkyl, (C$_{2-6}$)alkenyl, (C$_{2-6}$)alkynyl, (C$_{3-7}$)cycloalkyl-(C$_{1-6}$)alkyl-, aryl-(C$_{1-6}$)alkyl-, Het-(C$_{1-6}$)alkyl- or —W—$R^{31}$, and bond c is a single bond; or
$R^3$ is (C$_{1-6}$)alkylidene and bond c is a double bond;
wherein W is O or S and $R^{31}$ is (C$_{1-6}$)alkyl, (C$_{1-6}$)haloalkyl, (C$_{2-6}$)alkenyl, (C$_{2-6}$)alkynyl, (C$_{3-7}$)cycloalkyl, aryl, (C$_{3-7}$)cycloalkyl-(C$_{1-6}$)alkyl-, aryl-(C$_{1-6}$)alkyl- or Het-(C$_{1-6}$)alkyl-;
wherein each of the (C$_{1-6}$)alkylidene, (C$_{1-6}$)alkyl, (C$_{1-6}$)haloalkyl, (C$_{2-6}$)alkenyl, (C$_{2-6}$)alkynyl, (C$_{3-7}$)cycloalkyl-(C$_{1-6}$)alkyl-, aryl-(C$_{1-6}$)alkyl-, Het-(C$_{1-6}$)alkyl- and —W—$R^{31}$ is optionally substituted with 1 to 3 substituents each independently selected from $(C_{1-6})$alkyl, halo, cyano, oxo and —$O(C_{1-6})$alkyl;

$R^4$ is aryl or Het, wherein each of the aryl and Het is optionally substituted with 1 to 5 substituents each independently selected from halo, $(C_{1-6})$alkyl, $(C_{2-6})$alkenyl, $(C_{1-6})$haloalkyl, $(C_{3-7})$cycloalkyl, $(C_{3-7})$cycloalkyl-$(C_{1-6})$alkyl-, —OH, —$O(C_{1-6})$alkyl, —SH, —$S(C_{1-6})$alkyl, —$NH_2$, —$NH(C_{1-6})$alkyl and —$N((C_{1-6})alkyl)_2$; wherein the $(C_{1-6})$alkyl is optionally substituted with hydroxy, —$O(C_{1-6})$alkyl, cyano or oxo; and wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$;

or a salt thereof.

2. A compound according to claim 1 of the formula (Ie), or a pharmaceutically acceptable salt thereof:

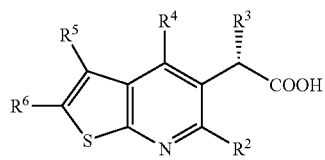

wherein $R^2$, $R^3$, $R^4$, $R^5$ and $R^6$ are as defined in claim 1.

3. A compound according to claim 1 of the formula (Ih), or a pharmaceutically acceptable salt thereof:

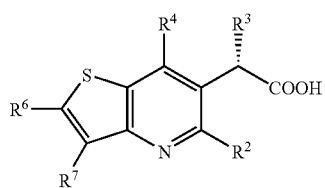

wherein $R^2$, $R^3$, $R^4$, $R^6$ and $R^7$ are as defined in claim 1.

4. A compound according to any one of claims 1 to 3, or a pharmaceutically acceptable salt thereof, wherein $R^2$ is $(C_{1-6})$alkyl or —$O(C_{1-6})$alkyl.

5. A compound according to any one of claims 1 to 3, or a pharmaceutically acceptable salt thereof, wherein $R^3$ is —$O(C_{1-4})$alkyl; wherein the —$O(C_{1-4})$alkyl is optionally substituted with 1 to 2 substituents each independently selected from cyano, oxo and —$O(C_{1-6})$alkyl; and bond c is a single bond.

6. A compound according to any one of claims 1 to 3, or a pharmaceutically acceptable salt thereof, wherein $R^4$ is phenyl optionally substituted with 1 to 3 substituents each independently selected from F, Cl, Br, $NH_2$, —$CH_3$, —$CH_2CH_3$, —$CH_2CH_2CH_3$, $CH_2F$, $CF_3$ and —$CH_2CH_2F$.

7. A compound according to any one of claims 1 to 3, or a pharmaceutically acceptable salt thereof, wherein $R^4$ is Het optionally substituted with 1 or 2 substituents each independently selected from halo, $(C_{1-6})$alkyl and —$O(C_{1-6})$alkyl;

wherein the Het is a 5- or 6-membered heterocycle having 1 to 3 heteroatoms each independently selected from N, O and S; or the Het is a 9- or 10-membered heteropolycycle having 1 to 3 heteroatoms each independently selected from N, O and S.

8. A compound according to any one of claims 1 to 3, or a pharmaceutically acceptable salt thereof, wherein $R^4$ is aryl or Het optionally substituted with 1 to 3 substituents each independently selected from halo, $(C_{1-6})$alkyl, $(C_{1-6})$haloalkyl, $NH_2$ and —$O(C_{1-6})$alkyl;

wherein the aryl is selected from:

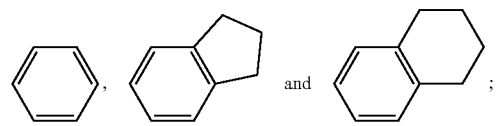

and wherein the Het is selected from:

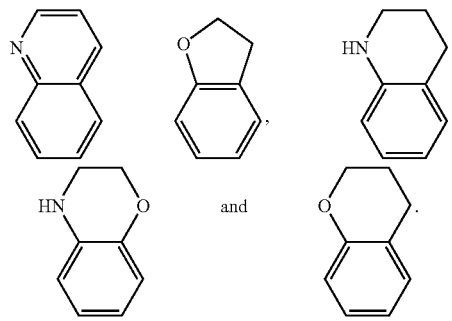

9. A compound according to claim 1 or 2, or a pharmaceutically acceptable salt thereof, wherein $R^5$ is H or $(C_{1-4})$alkyl.

10. A compound according to any one of claims 1 to 3, or a pharmaceutically acceptable salt thereof, wherein $R^6$ is H or $(C_{1-4})$alkyl.

11. A compound according to claim 1 or 3, or a pharmaceutically acceptable salt thereof, wherein $R^7$ is H or $(C_{1-4})$alkyl.

12. A pharmaceutical composition comprising a compound according to any one of claims 1 to 3, or a pharmaceutically acceptable salt thereof; and a pharmaceutically acceptable carrier.

13. A method for treating HIV infection in a host infected by HIV which method comprises administering to said host a therapeutically effective amount of a compound according to any one of claims 1 to 3, or a pharmaceutically acceptable salt thereof.

* * * * *